US008492109B2

(12) United States Patent
Oyler et al.

(10) Patent No.: US 8,492,109 B2
(45) Date of Patent: Jul. 23, 2013

(54) METHODS FOR THE DELIVERY OF TOXINS OR ENZYMATICALLY ACTIVE PORTIONS THEREOF

(75) Inventors: George A. Oyler, Baltimore, MD (US); Charles B. Shoemaker, North Grafton, MA (US); Chuehling Kuo, Framingham, MA (US)

(73) Assignee: Trustees of Tufts College, Medford, MA (US)

( * ) Notice: Subject to any disclaimer, the term of this patent is extended or adjusted under 35 U.S.C. 154(b) by 303 days.

(21) Appl. No.: 12/690,427

(22) Filed: Jan. 20, 2010

(65) Prior Publication Data
US 2010/0209955 A1    Aug. 19, 2010

Related U.S. Application Data

(60) Provisional application No. 61/145,820, filed on Jan. 20, 2009.

(51) Int. Cl.
*C12Q 1/37* (2006.01)
*C12Q 1/02* (2006.01)
*C12N 5/07* (2010.01)
*C12N 15/00* (2006.01)

(52) U.S. Cl.
USPC .......................................................... 435/24

(58) Field of Classification Search
USPC .............. 424/239.1, 236.1; 435/24, 375, 440, 435/29; 530/350
See application file for complete search history.

(56) References Cited

U.S. PATENT DOCUMENTS

| | | | |
|---|---|---|---|
| 6,203,794 B1 | 3/2001 | Dolly et al. | |
| 7,608,275 B2 | 10/2009 | Deem et al. | |
| 7,815,917 B2 | 10/2010 | Steward et al. | |
| 2004/0072270 A1 | 4/2004 | Fernandez-Salas et al. | |
| 2004/0219619 A1* | 11/2004 | Fernandez-Salas et al. . | 435/7.32 |
| 2006/0233836 A1 | 10/2006 | Kincaid et al. | |
| 2010/0015116 A1 | 1/2010 | Oyler et al. | |
| 2010/0278826 A1 | 11/2010 | Oyler et al. | |

OTHER PUBLICATIONS

Mahrhold, S., et al., "The Synaptic Vesicle Protein 2C Mediates the Uptake of Botulinum Neurotoxin A Into Phrenic Nerves," *FEBS Letters*, 580(8):2011-2014 (2006).
Simpson, L., et al., "Inhibition of Vacuolar Adenosine Triphosphatase Antagonizes the Effects of Clostridial Neurotoxins but Not Phospholipase A2 Neurotoxins," *J. Pharmacol. Exp. Ther.*, 269(1):256-262 (1994).
Boyd, R., et al., "The Effect of Botulinum Neurotoxins in the Release of Insulin from the Insulinoma Cell Lines HIT-15 and RINm5F," *J. Biol. Chem.*, 270(31):18216-18228 (1995).
Bartels, F., et al., "Restoration of Exocytosis Occurs After Inactivation of Intracellular Tetanus Toxin," *Infect. Immun.*, 60(1):302-307 (1992).
Simpson, L., "Kinetic Studies on the Interaction Between Botulinum Toxin Type A and the Cholinergic Neuromuscular Junction," *J. Pharmacol. Exp. Ther.*, 212(1):16-21 (1980).
Humeau, Y., et al., "How Botulinum and Tetanus Neurotoxins Block Neurotransmitter Release," *Biochimie*, 82(5):427-446 (2000).
Simpson, L., "The Origin, Structure, and Pharmacological Activity of Botulinum Toxin," *Pharmacol. Rev.*, 33(3):155-188 (1981).
DasGupta, B. R., et al., "A Common Subunit Structure in Clostridium Botulinum Type A, B and E Toxins," *Biochem. Biophys. Res. Commun.*, 48(1):108-112 (1972).
Schiavo, G., et al., "Neurotoxins Affecting Neuroexocytosis," *Physiol. Rev.*, 80(2):717-766 (2000).
Kozaki, S., et al., "Immunological Characterization of Papain-Induced Fragments of *Clostridium botulinum* Type A Neurotoxin and Interaction of the Fragments with Brain Synaptosomes," *Infect. Immun.*, 57(9):2634-2639 (1989).
Lalli, G., et al., "Functional Characterisation of Tetanus and Botulinum Neurotoxins Binding Domains," *J. Cell Sci.*, 112(16):2715-2724 (1999).
Montecucco, C., et al., "Tetanus and Botulism Neurotoxins: A New Group of Zinc Proteases," *Trends Biochem. Sci.*, 18(9):324-327 (1993).
Montecucco, C., "How do Tetanus and Botulinum Toxins Bind to Neuronal Membranes?" *Trends. Biochem. Sci.*, 11:315-317 (1986).
Kitamura, M., et al., "Interaction Between *Clostridium botulinum* Neurotoxin and Gangliosides," *Biochim. Biophys. Acta*, 628(3):328-335 ( 1980).
Hoch, D., et al., "Channels Formed by Botulinum, Tetanus, and Diphtheria Toxins in Planar Lipid Bilayers: Relevance to Translocation of Proteins Across Membranes," *Proc. Natl. Acad. Sci. USA*, 82(6):1692-1696 (1985).
Lacy. B., et al., "Crystal Structure of Botulinum Neurotoxin Type A and Implications for Toxicity," *Nat. Struct. Biol.*, 5(10):898-902 (1998).
Nishiki, T., et al., "The High-Affinity Binding of *Clostridium botulinum* Type B Neurotoxin to Synaptotagmin II Associated with Gangliosides $G_{T1b}/G_{D1a}$," *FEBS Letters*, 378(3):253-257 (1996).
Nishiki, T., et al., "Identification of Protein Receptor for *Clostridium botulinum* Type B Neurotoxin in Rat Brain Synaptosomes," *J. Biol. Chem.*, 269(14):10498-10503 (1994).
Schmid, M., et al., "Direct Visualization of Botulinum Neurotoxin-Induced Channels in Phospholipid Vesicles," *Nature*, 364(6440):827-830 (1993). (From *PubMed*, Abstract No. 7689178).
Foran, P., et al., "Botulinum Neurotoxin C1 Cleaves Both Syntaxin and SNAP-25 in Intact and Permeabilized Chromaffin Cells: Correlation With its Blockade of Catecholamine Release," *Biochemistry*, 35(8):2630-2636 (1996). (From *PubMed*, Abstract No. 8611567).

(Continued)

*Primary Examiner* — Chin-Min Kam
(74) *Attorney, Agent, or Firm* — Antoinette G. Giugliano, PC; AGG Intellectual Property Law

(57) ABSTRACT

The present invention relates to methods, systems, and kits for intoxicating cells, neuronal and non-neuronal cells, with a toxin or fragment thereof. This is done by subjecting toxin substrate and a lipid or polymeric carrier (e.g., DNA uptake facilitating agent) to one or more cells for use in cell based assays. In an aspect, the methods of the present invention allow for high throughput assays and, as such, for the evaluation of drug candidates.

13 Claims, 19 Drawing Sheets

OTHER PUBLICATIONS de Paiva, Anton et al., "Light Chain of Botulinum Nuerotoxin is Active in Mammalian Motor Nerve Terminals When Delivered Via Liposomes." *FEBS Letters*, 277(1-2):171-174 (1990).

van der Wijk, Thea et al., "Increased Vesicle Recycling in Response to Osmotic Cell Swelling." *The Journal of Biological Chemistry*, 278(41):40020-40025 (2003).

Lang, Jochen et al., "Transient Expression of Botulinum Nuerotoxin C1 Light Chain Differentially Inhibits Calcium and Glucose Induced Insulin Secretion in Clonal β-cells" *FEBS Letters*, 419(4-13-17 (1997).

Poma, Anna et al., "Nuclear Damaged Induced by Liposomes Containing FITC-Labeled Saporin on Human Melanoma Cells in Vitro" *Journal of Liposome Research*, 11(1):91-102 (2001).

Lavignac, Nathalie et al., Synthesis and Endosomolytic Properties of Poly (amidoamine) Block Copolymers, *Macromolecular Bioscience*, 4(1):922-929 (2004).

Kuo, Cheung-Ling et al., "Lipid and Cationic Polymer Based Transduction of Botulinum Holotoxin, or Toxin Protease Alone, Extends the Target Cell Range and Improves the Efficiency of Intoxication", *Toxicon*, 55(2-3):619-629 (2010).

Sells, Mary Aim et al., "Delivery of Protein into Cells Using Polycationic Liposomes", *PubMed*, 19(1): 72-76, 78 (1995).

Futami, Junichiro et al., "Intracellular Delivery of Proteins into Mammalian Living Cells by Polyethylenimine-Cationization", *Journal of Bioscience and Bioengineering*, 99(2):95-103 (2005).

Roberts, Josh, "Buyers Guide to Protein Transduction Regents", *The Scientist*, 18(14-1-27 (2004).

Caccin, Paola, et al., *FEBS Letters* 542: 132-136 (2003).

Rummel, A., et al., "Synaptotagmins I and II Act as Nerve Cell receptors for Botulinum Neurotoxin G," *J. Biol. Chem.*, 279(29):30865-30870 (2004).

Bowman, E., et al.,"Bafilomycins: A Class of Inhibitors of Membrane ATPases from Microorganisms, Animal Cells, and Plant Cells," *Proc. Nati Acad. Sci. USA*, 85(21):7972-7976 (1988).

Werner, G., et al., "Metabolic Products of Microorganisms. 224 Bafilomycins, A New Group of Macrolide Antibiotics Production, Isolation, Chemical Structure and Biological Activity," *J. Antibiot.*, 37(2):110-117 (1984).

Montecucco, G., et al., "Bacterial Protein Toxins Penetrate Cells Via a Four-Step Mechanism," *FEBS Letters*, 346(1):92-98 (1994).

Shone, C., et al., "A 50-kDa Fragment From the $NH_2$-Terminus of the Heavy Subunit of *Clostridium botulinum* Type A Neurotoxin Forms Channels in Lipid Vesicles," *Eur. J. Biochem.*, 167(1):175-180 (1987).

Schiavo, G., et al., "Tetanus and Botulinum-B Neurotoxins Block Neurotransmitter Release by Proteolytic Cleavage of Synaptobrevin," *Nature*, 359(6398): 832-835 (1992).

Schiavo, G., et al., "Botulinum G Neurotoxin Cleaves VAMP/Synaptobrevin at a Single Ala-Ala Peptide Bond," *J. Biol. Chem.*, 269(32):20213-20216 (1994).

Schiavo, G., et al., "Identification of the Nerve Terminal Targets of Botulinum Neurotoxin Serotypes A, D, and E," *J. Biol. Chem.*, 268(32):23784-23787 (1993).

Schiavo, G., et al., "Botulinum Neurotoxin Serotype F Is a Zinc Endopeptidase Specific for VAMP/Synaptobrevin," *J. Biol. Chem.*, 268(16):11516-11519 (1993).

Schiavo, G., et al., "Botulinum Neurotoxin Type C Cleaves a Single Lys-Ala Bond Within the Carboxyl-Terminal Region of Syntaxins," *J. Biol. Chem.*, 270(18):10566-10570 (1995).

Li, L., et al., "Isolation of Synaptotagmin as a Receptor for Types A and E Botulinum Neurotoxin and Analysis of Their Comparative Binding Using a New Microtiter Plate Assay," *J. Nat. Toxins*, 7(3):215-226 (1998). (From *PubMed*, Abstract No. 9783260).

\* cited by examiner

Figure 3

| BoNT/A concentration (nM) | 10 | 1 | 0.1 | 10 | 1 | 0.1 |
| --- | --- | --- | --- | --- | --- | --- |
| Transfection reagent | + | + | + | - | - | - |

SNAP25
Cleaved SNAP25

|  | 4 h incubation | 24 h incubation | |
|---|---|---|---|
|  | BoNT/A1 | BoNT/A1 | Lc438 |
| Bafilomycin | + - + - | + - + - | + - + - |
| Fugene | + + - - | + + - - | + + - - |

RGCN

M17

Neuro2a

HEK293

HIT-T15

A

C

B

D

BoNT/A1 LC

```
  1 mpfvnkqfny kdpvngvdia yikipnvgqm qpvkafkihn kiwviperdt ftnpeegdln
 61 pppeakqvpv syydstylst dnekdnylkg vtklferiys tdlgrmllts ivrgipfwgg
121 stidtelkvi dtnciqviqp dgsyrseeln lviigpsadi iqfecksfgh evlnltrngy
181 gstqyirfsp dftfgfeesl evdtnpllga gkfatdpavt lahelihagh rlygiainpn
241 rvfkvntnay yemsglevsf eelrtfgghd akfidslqen efrlyyynkf kdiastlnka
301 ksivgttasl qymknvfkek yllsedtsgk fsvdklkfdk lykmltciyt cdnfvkffkv
361 lnrktylnfd kavfkinivp kvnytiydgf nlrntnlaan fngqnteirn mnftklknft
421 glfefykllc vrgiitsktk (SEQ ID NO: 2)
```

```
atgccgtttgtgaacaaacagtttaactataaagatccggtgaacggcgtggatattgcg
tatattaaaattccgaacgtgggccagatgcagccggtgaaagcgtttaaaattcataac
aaaatttgggtgattccggaacgcgatacctttaccaacccggaagaaggcgatctgaac
ccgccgccggaagcgaaacaggtgccggtgagctattatgatagcacctatctgagcacc
gataacgaaaagataactatctgaaaggcgtgaccaaactgtttgaacgcatttatagc
accgatctgggccgcatgctgctgaccagcattgtgcgcggcattccgttttgggcggc
agcaccattgataccgaactgaaagtgattgataccaactgcattaacgtgattcagccg
gatggcagctatcgcagcgaagaactgaacctggtgattattggcccgagcgcggatatt
attcagtttgaatgcaaaagctttggccatgaagtgctgaacctgacccgcaacggctat
ggcagcacccagtatattcgctttagcccggattttacctttggctttgaagaaagcctg
gaagtggataccaacccgctgctgggcgcgggcaaatttgcgaccgatccggcggtgacc
ctggcgcatgaactgattcatgcgggccatcgcctgtatggcattgcgattaacccgaac
cgcgtgtttaaagtgaacaccaacgcgtattatgaaatgagcggcctggaagtgagcttt
gaagaactgcgcacctttggcggccatgatgcgaaatttattgatagcctgcaggaaaac
gaatttcgcctgtattattataacaaatttaaagatattgcgagcaccctgaacaaagcg
aaaagcattgtgggcaccaccgcgagcctgcagtatatgaaaaacgtgtttaaagaaaaa
tatctgctgagcgaagataccagcggcaaatttagcgtggataaactgaaatttgataaa
ctgtataaaatgctgaccgaaatttataccgaagataactttgtgaaattttttaaagtg
ctgaaccgcaaaacctatctgaactttgataaagcggtgtttaaaattaacattgtgccg
aaagtgaactataccatttatgatggctttaacctgcgcaacaccaacctggcggcgaac
tttaacggccagaacaccgaaattaacaacatgaactttaccaaactgaaaaactttacc
ggcctgtttgaattttataaactgctgtgcgtgcgcggcattattaccagcaaaaccaaatag (SEQ ID NO: 1)
```

Figure 9A

BoNT/A2 LC

MPFVNKQFNYKDPVNGVDIAYIKIPNAGQMQPVKAFKIHNKIWVIPERDTFTNPEEGDLNPPPEAKQVPVSYYDSTYLSTDNEKDNYLKGVTKLFER
IYSTDLGRMLLTSIVRGIPFWGGSTIDTELKVIDTNCINVIQPDGSYRSEELNLVIIGPSADIIQFECKSFGHDVLNLTRNGYGSTQYIRFSPDFTF
GFEESLEVDTNPLLGAGKFATDPAVTLAHELIHAEHRLYGIAINPNRVFKVNTNAYYEMSGLEVSFEELRTFGGHDAKFIDSLQENEFRLYYYNKFK
DVASTLNKAKSIIGTTASLQYMKNVFKEKYLLSEDTSGKFSVDKLKFDKLYKMLTEIYTEDNFVNFFKVINRKTYLNFDKAVFRINIVPDENYTIKD
GFNLKGANLSTNFNGQNTEINSRNFTRLKNFTGLFEFYKLLCVRGIIPFKTKSLDEGYNK (SEQ ID NO: 4)

atgccgtttgtgaacaaacagtttaactataaagatccggtcaacggcgtggatattgcg tatattaaaattccgaacgcggccagatgcagccggtgaaagcgtttaaaattcataac aaaatttgggtgattccggaacgcgataccttaccaaccccgaagaagcgatctgaac ccgccgccggaagcgaaacagtgccggtgagctattatgatagcacctatctgagcacc gataacgaaaagataactatctgaaaggcgtgaccaaactgtttgaacgcatttatagc accgatctggcgcatgctgctgaccagcattgtgcgcggcattccgttttggggcggc agcaccattgataccgaactgaaagtgattgataccaactgcattaacgtgattcagccg gatggcagctatcgcagcgaagaactgaacctggtgattattggcccgagcgcggatatt attcagtttgaatgcaaaagctttggccatgatgtgctgaacctgaccgcaacggctat ggcagcacccagtatattcgctttagcccggattttacctttggctttgaagaaagcctg gaagtggataccaacccgctgctgggcgcgggcaaatttgcgaccgatccggcggtgacc ctggcgcatgaactgattcatgcggaacatcgcctgtatggcattgcgattaacccgaac ccgtgtttaaagtgaacaccaacgcgtattatgaaatgagcggcctggaagtgagctt gaagaactgcgcacctttggcggccatgatgcgaaatttattgatagcctgcaggaaaac gaatttcgcctgtattattataacaaatttaaagatgtggcgagcaccctgaacaaagcg aaaagcattattggcaccaccgcgagcctgcagtatatgaaaaacgtgtttaaagaaaaa tatctgctgagcgaagataccagcggcaaatttagcgtggataaactgaaatttgataaa ctgtataaaatgctgaccgaaattataccgaagataactttgtgaacttttttaaagtg attaaccgcaaaacctatctgaactttgataaagcggtgtttcgcattaacattgtgccg gatgaaaactataccattaaagatggctttaacctgaaaggcgcgaacctgagcaccaac tttaacggccagaacaccgaaattaacagccgcaacttacccgcctgaaaaactttacc ggcctgtttgaattttataaaactgctgtgcgtgcgcggcattattccgtttaaaaccaaa agcctggatgaaggctataacaaatag (SEQ ID NO: 3)

Figure 9B

BoNT/A3 LC

MPFVNKPFNYRDPGNGVDIAYIKIPNAGQMQPVKAFKIHEGVWVIPERDTFTNPEEGDLNPPPEAKQVPVSYYDSTYLSTDNEKDNYLKGVIKLFDR
IYSTGLGRMLLSFIVKGIPFWGGSTIDTELKVIDTNCINVIEPGGSYRSEELNLVITGPSADIIQFECKSFGHDVFNLTRNGYGSTQYIRFSPDFTF
GFEESLEVDTNPLLGAGTFATDPAVTLAHELIHAAHRLYGIAINPNRVLKVKTNAYYEMSGLEVSFEELRTFGGNDTNFIDSLWQKKFSRDAYDNLQ
NIARILNEAKTIVGTTTPLQYMKNIFIRKYFLSEDASGKISVNKAAFKEFYRVLTRGFTELEFVNPFKVINRKTYLNFDKAVFRINIVPDENYTINE
GFNLEGANSNGQNTEINSRNFTRLKNFTGLFEFYKLLCVRGIIPFKTKSLDEGYNK (SEQ ID NO: 6)

atgccgtttgtgaacaaaccgtttaactatcgcgatccgggcaacggcgtggatattgcg tatattaaaattccgaacgcgggccagatgcagccggtgaaagcgtttaaaattcatgaa ggcgtgtgggtgattccggaacgcgatacctttaccaacccggaagaaggcgatctgaac ccgccgccggaagcgaaacaggtgccggtgagctattatgatagcacctatctgagcacc gataacgaaaaagataactatctgaaaggcgtgattaaactgtttgatcgcatttatagc accggcctgggccgcatgctgctgagctttattgtgaaaggcattccgttttggggcggc agcaccattgataccgaactgaaagtgattgataccaactgcattaacgtgattgaaccg ggcggcagctatcgcagcgaagaactgaacctggtgattaccggcccgagcgcggatatt attcagtttgaatgcaaaagctttggccatgatgtgtttaacctgacccgcaacggctat ggcagcacccagtatattcgctttagcccggattttacctttggctttgaagaaagcctg gaagtggataccaacccgctgctgggcgcgggcacctttgcgaccgatccggcggtgacc ctggcgcatgaactgattcatgcggcgcatcgcctgtatggcattgcgattaacccgaac cgcgtgctgaaagtgaaaaccaacgcgtattatgaaatgagcggcctggaagtgagcttt gaagaactgcgcacctttggcggcaacgataccaactttattgatagcctgtggcagaaa aaatttagccgcgatgcgtatgataacctgcagaacattgcgcgcattctgaacgaagcg aaaaccattgtgggcaccaccaccccgctgcagtatatgaaaaacatttttattcgcaaa tatttttctgagcgaagatgcgagcggcaaaattagcgtgaacaaagcggcgtttaaagaa ttttatcgcgtgctgacccgcggctttaccgaactggaatttgtgaacccgtttaaagtg attaaccgcaaaacctatctgaactttgataaagcggtgtttcgcattaacattgtgccg gatgaaaactataccattaacgaaggctttaacctggaaggcgcgaacagcaacggccag aacaccgaaattaacagccgcaactttacccgcctgaaaaactttaccggcctgtttgaa ttttataaactgctgtgcgtgcgcggcattattccgtttaaaaccaaaagcctggatgaa ggctataacaaatag (SEQ ID NO: 5)

Figure 9C

Botulinum B1 Okra P10844.

```
  1 mpvtinnfny ndpidnrnii mmeppfargt gryykafkit driwiipery tfgykpedfn
 61 kssgifnrdv ceyydpdyln tndkkniflq tmiklfnrik skplgeklle miingipylg
121 drrvpleefn tniasvtvnk lisnpgever kkgifarlii fgpgpvlnen etidigiqnh
181 fasregfggi mqmkfcpeyv svfnnvqenk gasifnrrgy fsdpalilmh elihvlhgly
241 gikvddlpiv pnekkffmqs tdaiqaeely tfggqdpsii tpstdksiyd kvlqnfrgiv
301 drlnkvlvci sdpninniy knkfkdkykf vedsegkysi dvesfdklyk slmfgftetn
361 iaenykiktr asyfsdslpp vkiknlldne iytieegfni sdkdmekeyr gqnkainkqa
421 yeeiskehla vykiqmcksv k  (SEQ ID NO: 8)
```

```
atgccggtgaccattaacaactttaactataacgatccgattgataacaacaacattatt
atgatggaaccgccgtttgcgcgcggcaccggccgctattataaagcgtttaaaattacc
gatcgcatttggattattccggaacgctatacctttggctataaaccggaagatttaac
aaaagcagcggcatttttaaccgcgatgtgtgcgaatattatgatccggattatctgaac
accaacgataaaaaaaacatttttctgcagaccatgattaaactgtttaaccgcattaaa
agcaaaccgctgggcgaaaaactgctgaaatgattattaacggcattccgtatctgggc
gatcgccgcgtgccgctggaagaatttaacaccaacattgcgagcgtgaccgtgaacaaa
ctgattagcaacccgggcgaagtggaacgcaaaaaaggcatttttgcgaacctgattatt
tttggcccgggcccggtgctgaacgaaaacgaaaccattgatattggcattcagaaccat
tttgcgagccgcgaaggctttggcggcattatgcagatgaaattttgcccggaatatgtg
agcgtgtttaacaacgtgcaggaaaacaaaggcgcgagcatttttaaccgccgcggctat
tttagcgatccggcgctgattctgatgcatgaactgattcatgtgctgcatggcctgtat
ggcattaaagtggatgatctgccgattgtgccgaacgaaaaaaattttttatgcagagc
accgatgcgattcaggcggaagaactgtataccttggcggccaggatccgagcattatt
accccgagcaccgataaaagcatttatgataaagtgctgcagaactttcgcggcattgtg
gatcgcctgaacaaagtgctggtgtgcattagcgatccgaacattaacattaacatttat
aaaaacaaatttaaagataaatataaatttgtggaagatagcgaaggcaaatatagcatt
gatgtggaaagctttgataaactgtataaaagcctgatgtttggctttaccgaaaccaac
attgcggaaaactataaaattaaaacccgcgcgagctattttagcgatagcctgccgccg
gtgaaaattaaaaacctgctggataacgaaatttataccattgaagaaggctttaacatt
agcgataaagatatggaaaaagaatatcgcggccagaacaaagcgattaacaaacaggcg
tatgaagaaattagcaaagaacatctggcggtgtataaaattcagatgtgcaaaagcgtg
aaatag  (SEQ ID NO: 7)
```

Figure 9D

Botulinum B2 Eklund 17B

```
  1 mpvtinnfny ndpidndnii mmeppfargt gryykafkit driwiipery tfgykpedfn
 61 kssgifnrdv ceyydpdyln tndkkniflq tmiklfnrik skplgeklle miingipylg
121 drrvpeefn tniasvtvnk lisnpgeveq kkgifanlii fgpgpvlnen etidigiqrh
181 fasregfggi mqmkfcpeyv svfnnvqenk gasifnrrgy fsdpalilmh elihvlhgly
241 gikvddlpiv pnekkffmqs tdtiqaeely tfgcqdpsii spstdksiyd kvlqnfrgiv
301 drlnkvlvci sdpninniy knkfkdkykf vedsegkysi dvesfnklyk slmfgftein
361 iacnykiktr asyfsdslpp vkiknlldnc iyticcgfni sdknmgkcyr gqnkainkqa
421 yeeiskehla vykiqmcksv  (SEQ ID NO: 10)
```

```
atgccggtgaccattaacaactttaactataacgatccgattgataacgataacattatt
atgatggaaccgccgtttgcgcgcggcaccggccgctattataaagcgtttaaaattacc
gatcgcatttggattattccggaaccgctataccctttggctataaaccggaagattttaac
aaaagcagcggcatttttaaccgcgatgtgtgcgaatattatgatccggattatctgaac
accaacgataaaaaaaacatttttctgcagaccatgattaaactgtttaaccgcattaaa
agcaaaccgctgggcgaaaaactgctggaaatgattattaacggcattccgtatctgggc
gatcgccgcgtgccgctggaagaatttaacaccaacattgcgagcgtgaccgtgaacaaa
ctgattagcaacccgggcgaagtggaacagaaaaaaggcatttttgcgaacctgattatt
tttggcccgggcccggtgctgaacgaaaacgaaaccattgatattggcattcagaaccat
tttgcgagccgcgaaggctttggcggcattatgcagatgaaattttgcccggaatatgtg
agcgtgtttaacaacgtgcaggaaaacaaaggcgcgagcatttttaaccgccgcggctat
tttagcgatccggcgctgattctgatgcatgaactgattcatgtgctgcatggcctgtat
ggcattaaagtggatgatctgccgattgtgccgaacgaaaaaaaatttttttatgcagagc
accgataccattcaggcggaagaactgtatacctttggccgccaggatccgagcattatt
agcccgagcaccgataaaagcatttatgataaagtgctgcagaactttcgcggcattgtg
gatcgcctgaacaaagtgctggtgtgcattagcgatccgaacattaacattaacatttat
aaaaacaaatttaaagataaatataaatttgtggaagatagcgaaggcaaatatagcatt
gatgtcgaaagctttaacaaactgtataaaagcctgatgtttggctttaccgaaattaac
attgccgaaaactataaaattaaaacccgcgccagctattttagcgatagcctgccgccg
gtgaaaattaaaaacctgctggataacgaaatttataccattgaagaaggctttaacatt
agcgataaaaacatgggcaaagaatatcgcggccagaacaaagcgattaacaaacaggcg
tatgaagaaattagcaaagaacatctggcggtgtataaaattcagatgtgcaaaagcgtgtag  (SEQ ID NO: 9)
```

Figure 9E

Neurotoxin type C1 Clostridium botulinum

BoNT/C1 LC

MPITINNFNYSDPVDNKNILYLDTHLNTLANEPEKAFRITGNIWVIPDRFSRNSNPNLNKPPRVTSPKSGYYDPNYLSTDSDKDPFLKEIIKLFKRI
NSREIGEELIYRLSTDIPFPGNNNTPINTFDFDVDFNSVDVKTRQGNNWVKTGSINPSVIITGPRENIIDPETSTFKLTNNTFAAQEGFGALSIISI
SPRFMLTYSNATNDVGEGRFSKSEFCMDPILILMHELNHAMHNLYGIAIPNDQTISSVTSNIFYSQYNVKLEYAEIYAFGGPTIDLIPKSARKYFEE
KALDYYRSIAKRLNSITTANPSSFNKYIGEYKQKLIRKYRFVVESSGEVTVNRNKFVELYNELTQIFTEFNYAKIYNVQNRKIYLSNVYTPVTANIL
DDNVYDIQNGFNIPKSNLNVLFMGQNLSRNPALRKVNPENMLYLFTKFCHKAIDGRSLYNK (SEQ ID NO: 12)

atgccgattaccattaacaactttaactatagcgatccggtggataacaaaaacattctg tatctggataccatctgaacaccctggcgaacgaacccgaaaaagcgtttcgcattacc ggcaacatttgggtgattccggatcgctttagccgcaacagcaacccgaacctgaacaaa ccgccgcgcgtgaccagcccgaaaagcggctattatgatccgaactatctgagcaccgat agcgataaagatccgtttctgaaagaaattattaaactgtttaaacgcattaacagccgc gaaattggcgaagaactgatttatcgcctgagcaccgatattccgtttccgggcaacaac aacaccccgattaacacctttgattttgatgtggattttaacagcgtggatgtgaaaacc cgccagggcaacaactggtgaaaaccggcagcattaacccgagcgtgattattaccggc ccgcgcgaaaacattattgatccggaaaccagcaccttaaactgaccaacaacacctttt gcggcgcaggaaggctttggcgcgctgagcattattagcattagcccgcgctttatgctg acctatagcaacgcgaccaacgatgtgggcgaaggccgctttagcaaaagcgaatttttgc atggatccgattctgattctgatgcatgaactgaaccatgcgatgcataacctgtatggc attgcgattccgaacgatcagaccattagcagcgtgaccagcaacattttttatagccag tataacgtgaaactggaatatgcggaaatttatgcgtttggcggcccgaccattgatctg attccgaaaagcgcgcgcaaatattttgaagaaaaagcgctggattattatcgcagcatt gcgaaacgcctgaacagcattaccaccgcgaacccgagcagctttaacaaatatattggc gaatataaacagaaactgattcgcaaatatcgctttgtggtggaaagcagcggcgaagtg accgtgaaccgcaacaaatttgtggaactgtataacgaactgacccagatttttaccgaa tttaactatgcgaaaatttataacgtgcagaaccgcaaaatttatctgagcaacgtgtat accccggtgaccgcgaacattctggatgataacgtgtatgatattcagaacggctttaac attccgaaaagcaacctgaacgtgctgtttatgggccagaacctgagccgcaacccggcg ctgcgcaaagtgaacccggaaaacatgctgtatctgtttaccaaattttgccataaagcg attgatggccgcagcctgtataacaaatag (SEQ ID NO: 11)

Figure 9F

Neurotoxin type D Clostridium botulinum

BoNT/D LC

```
  1 mtwpvkdfny sdpvndndil ylripqnkli ttpvkafmit qniwviperf ssdtnpslsk
 61 pprptskyqs yydpsylstd eqkdtflkgi iklfkrirer digkklinyl vvgspfmgds
121 stpedtfdft rhttniavek fengswkvtn iitpsvlifg plpnildyta sltlqgqqsn
181 psfegfgtls ilkvapefll tfsdvtsnqs savlgksifc mdpvialmhe lthslhqlyg
241 inipsdkrir pqvsegffsq dgpnvqfeel ytfcgldvei ipqiersqlr ekalghykdi
301 akrlnninkt ipsswisnid kykkifseky nfdkdntcnf vvnidkfnsl ysdltnvmse
361 vvyssqynvk nrthyfsrhy lpvfanildd niytirdgfn ltnkgfnicn sgqnicrnpa
421 lqklssesvv dlftkvclrl tk   (SEQ ID NO: 14)
``` atgacctggccggtgaaagattttaactatagcgatccggtgaacgataacgatattctg
tatctccgcattccgcagaacaaactgattaccacccggtgaaagcgtttatgattacc
cagaacatttgggtgattccggaacgctttagcagcgataccaacccgagcctgagcaaa
ccgccgcgcccgaccagcaaatatcagagctattatgatccgagctatctgagcaccgat
gaacagaaagatacctttctgaaaggcattattaaactgtttaaacgcattaacgaacgc
gatattggcaaaaaactgattaactatctggtggtgggcagcccgtttatggcgatagc
agcaccccgcaagatacctttgattttacccgccataccaccaacattgccgtgcaaaaa
tttgaaaacggcagctggaaagtgaccaacattattaccccgagcgtgctgatttttggc
ccgctgccgaacattctcgattataccgcgagcctgaccctgcagggccagcagagcaac
ccgagctttgaaggctttggcaccctgagcattctgaaagtggcgccggaatttctgctg
acctttagcgatgtgaccagcaaccagagcagcgcggtgctgggcaaaagcatttttttgc
atggatccggtgattgcgctgatgcatgaactgacccatagcctgcatcagctgtatggc
attaacattccgagcgataaacgcattcgcccgcaggtgagcgaagccttttttagccag
gatggcccgaacgtgcagtttgaagaactgtatacctttggcggcctggatgtggaaatt
attccgcagattgaacgcagccagctgcgcgaaaaagcgctgggccattataaagatatt
gcgaaacgcctgaacaacattaacaaaaccattccgagcagctggattagcaacattgat
aaatataaaaaattttttagcgaaaaatataactttgataaagataacaccggcaactttt
gtggtcaacattgataaatttaacagcctgtatagcgatctgaccaacgtcatgagcgaa
gtggtgtatagcagccagtataacgtgaaaaaccgcacccattattttagccgccattat
ctgccggtgtttgcgaacattctggatgataacatttataccattcgcgatggctttaac
ctgaccaacaaaggctttaacattgaaaacagcggccagaacattgaacgcaacccggcg
ctgcagaaactgagcagcgaaagcgtggtggatctgtttaccaaagtgtgcctgcgcctg
accaaatag (SEQ ID NO: 13)

Figure 9G

Neurotoxin type E Clostridium botulinum

BoNT/E LC
MPKINSFNYNDPVNDRTILYIKPGGCQEFYKSFNIMKNIWIIPERNVIGTTFQDFHPPTSLKNGDSSYYDPNYLCSDEEKDRFLKIVTKIFNRINNN
LSGGILLEELSKANPYLGNDNTPDNQFHIGDASAVEIKFSNGSQDILLPNVIIMGAEPDLFETNSSNISLRNNYMPSNHRFGSIAIVTFSPEYSFRF
NDNCMNEFIQDPALTLMHELIHSLHGLYGAKGITTKYTITQKQNPLITNIRGTNIEEFLTFGGTDLNIITSAQSNDIYTNLLADYKKIASKLSKVQV
SNPLLNPYKDVFEAKYGLDKDASCIYSVNINKFNDIFKKLYSFTEFDLATKFQVKCRQTYIGQYKYFKLSNLLNDSIYNISECYNINNLKVNFRGQN
ANLNPRIITPITGRGLVKKIIRFCKNIVSVKGIR   (SEQ ID NO: 16)

atgccgaaaattaacagctttaactataacgatccggtgaacgatcgcaccattctgtat attaaaccgggcggctgccagcaattttataaaagctttaacattatgaaaaacattgg attattccggaacgcaacgtgattggcaccacccgcaggattttcatccgccgaccagc ctgaaaaacggcgatagcagctattatgatccgaactatctgcagagcgatgaagaaaaa gatcgctttctgaaaattgtgaccaaaatttttaaccgcattaacaacaaccgagcggc ggcattctgctcgaagaactgagcaaagcgaacccgtatctgggcaacgataacacccg gataaccagtttcatattggcgatgcgagcgcggtggaaattaaatttagcaacggcagc caggatattctgctgccgaacgtgattattatggcgcgcgaaccgatctgtttgaaacc aacagcagcaacattagcctgcgcaacaactatatgccgagcaaccatcgctttggcagc attgcgattgtgacctttagcccggaatatagctttcgctttaacgataactgcatgaac gaatttattcaggatccggcgctgaccctgatgcatgaactgattcatagcctgcatggc ctgtatggcgccaaagcattaccaccaaatataccattaccacaaacagaacccgctg attaccaacattcgcggcaccaacattgaagaatttctgacctttggcggcaccgatctg aacattattaccagcgcgcagagcaacgatatttataccaacctgctggcggattataaa aaaattgcgagcaaactgagcaaagtgcaggtgagcaacccgctgctgaacccgtataaa gatgtgtttgaagcgaaatatcggcctggataaagatgcgagcggcatttatagcgtgaac attaacaaatttaacgatatttttaaaaaactgtatagctttaccgaatttgatctggcg accaaatttcaggtgaaatgccgccagacctatattggccagtataaatattttaaactg agcaacctgctgaacgatagcatttataacattagcgaaggctataacattaacaacctg aaagtgaactttcgcggccagaacgcgaacctgaaccgcgcattattaccccgattacc ggccgcggcctcgtgaaaaaaattattcgcttttgcaaaaacattgtgagcgtgaaaggc attcgctag (SEQ ID NO: 15)

Figure 9H

Neurotoxin type F Clostridium botulinum

>BoNT/F1 LC.
MPVAINSFNYNDPVNDDTILYMQIPYEEKSKKYYKAFEIMRNVWIIPERNTIGTNPSDFDPPASLKNGSSAYYDPNYLTTDAEKDRYLKTTIKLFKR
INSNPAGKVLLQEISYAKPYLGNDHTPIDEFSPVTRTTSVNIKLSTNVESSMLLNLLVLGAGPDIFESCCYPVRKLIDPDVVYDPSNYGFGSINIVT
FSPEYEYTFNDISGGHNSTESFIADPAISLAHELIHALHGLYGARGVTYEETIEVKQAPLMIAEKPIRLEEFLTFGGQDLNIITSAMKEKIYNNLL
ANYEKIATRLSEVNSAPPEYDINEYKDYFQWKYGLDKNADGSYTVNENKFNEIYKKLYSFTESDLANKFKVKCRNTYFIKYEFLKVPNLDDDIYTV
SEGFNIGNLAVNNRGQSTKLNPKTIDSTPDKGLVEKIVKFCKSVTPRK    (SEQ ID NO: 18)

atgccgtggcgattaacagctttaactataacgatccggtgaacgatgataccattctg tatatgcagattccgtatgaagaaaaagcaaaaatatattaaaagcgtttgaaattatg cgcaacgtgtggattattccggaacgcaacaccattggcaccaacccgagcgattttgat ccgccgccgcagcctgaaaaacggcagcagcgcgtattatgatccgaactatctgaccacc gatgccgaaaaagatcgctatctgaaaaccaccattaaactgtttaaacgcattaacagc aacccgccggcaaagtgctgctgcaggaaattagctatgcgaaaccgtatctgggcaac gatcataccccgattgatgaatttagcccggtgaccccgcaccaccagcctgaacattaaa ctgagcaccaacgtggaaagcagcatgctgctgaacctgctgctgctgggcgcgggcccg gatatttttgaaagctgctgctatccggtgcgcaaactgattgatccggatgtggtgtat gatccgagcaactatggctttggcagcattaacattgtgacctttagcccggaatatgaa tatacctttaacgatattagcggcggccataacagcagcaccgaaagctttattgcggat ccggcgattagcctggcgcatgaactgattcatgcgctgcatggcctgtatggcgcgcgc ggcgtgacctatgaagaaaccattgaagtgaaacaggcgccgctgatgattgcggaaaaa ccgattcgcctggaagaatttctgacctttggcggccaggatctgaacattattaccagc gcgatgaaagaaaaaatttataacaacctgctggcgaactataaaaaattgcgacccgc ctgagcgaagtgaacagcgcgccgccggaatatgatattaaccaatataaagattatttt cagtgcaaatatggcctggataaaaacgcggatggcagctataccgtgaaccaaaacaaa tttaacgaaatttataaaaaactgtatagctttaccgaaagcgatctggcgaacaaattt aaagtgaaatgccgcaacacctatttttattaaatatgaatttctgaaagtgccgaacctg ctggatgatgatatttataccgtgagcgaaggctttaacattggcaacctggcggtgaac aaccgcggccagagcattaaactgaacccgaaaattattgatagcattccggataaaggc ctggtggaaaaaattgtgaaattttgcaaaagcgtgattccgcgcaaatag (SEQ ID NO: 17)

Figure 9I

Neurotoxin type F Clostridium baratii

BoNT/F2

```
  1 mpvninnfny ndpinnttil ymkmpyyeds rkyykafeim dnvwiipern iigkkpsdfy
 61 ppisldsgss ayydpnylrt daekdrflkt viklfnrins npagqvllee ikngkpylgn
121 dhtavnefca nnrstsveik esngttdsml lnlvilgpgp nilecstfpv rifpnniayd
181 psekgfgsiq lmsfsteyey afndntdlfi adpaislahe lihvlhglyg akgvtnkkvi
241 evdqgalmaa ekdikieefi tfgqqdlnii tnstnqkiyv illsnytaia srlsqvnrnn
301 salnttyykn ffqwkygldq dsngnytvni skfnaiykkl fsftecdlaq kfqvknrsny
361 lfhfkpfrll dllddhiysi segfnigslr vnnngqninl nsrivgpipd nglverfvgl
421 cksivskkgt knslcik     (SEQ ID NO: 20)
``` atgccggtcaacattaacaactttaactataacgatccgattaacaacaccaccattctg tatatgaaaatgccgtattatgaagatagcaacaaatattataaagcgtttgaaattatg gataacgtctggattattccggaacgcaacattattggcaaaaaaccgagcgatttttat ccgccgattagcctggatagcggcagcagcgcgtattatgatccgaactatctgaccacc gatgcggaaaaagatcgctttctgaaaaccgtgattaaactgtttaaccgcattaacagc aacccggcgggccaggtgctgctggaagaaattaaaaacggcaaaccgtatctgggcaac gatcataccgcggtgaacgaattttgcgcgaacaaccgcagcaccagcgtggaaattaaa gaaagcaacggcaccaccgatagcatgctgctgaacctggtgattctgggcccgggcccg aacattctggaatgcagcacctttccggtgcgcatttttccgaacaacattgcgtatgat ccgagcgaaaaaggctttggcagcattcagctgatgagctttagcaccgaatatgaatat gcgtttaacgataacaccgatctgtttattgcggatccggcgattagcctggcgcatgaa ctgattcatgtgctgcatggcctgtatggcgcgaaaggcgtgaccaacaaaaaagtgatt gaagtggatcagggcgcgctgatggcggcggaaaaagatattaaaattgaagaatttatt acctttggcggccaggatctgaacattattaccaacagcaccaaccagaaaatttatgtg attctgctgagcaactataccgcgattgcgagccgcctgagccaggtgaaccgcaacaac agcgcgctgaacaccacctattataaaaactttttttcagtggaaatatggcctggatcag gatagcaacggcaactataccgtgaacattagcaaatttaacgcgatttataaaaaactg tttagctttaccgaatgcgatctggcgcagaaatttcaggtgaaaaaccgcagcaactat ctgtttcattttaaaccgtttcgcctgctggatctgctggatgataacatttatagcatt agcgaaggctttaacattggcagcctgcgcgtgaacaacaacggccagaacattaacctg aacagccgcattgtgggcccgattccggataacggcctggtggaacgctttgtgggcctg tgcaaaagcattgtgagcaaaaaaggcaccaaaaacagcctgtgcattaaatag (SEQ ID NO: 19)

Figure 9J

```
Neurotoxin type G Clostridium botulinum

BoNT/G 1 mpvnikxfny ndpinnddii mmepfndpgp gtyykafrii driwivperf tygfqpdqfn
   61 astcvfskdv yeyydptylk tdaekdkflk tmiklfnrin skpsgqrlld mivdaipylg
  121 nastppdkfa anvanvsink kiiqpgaedq ikglmtnlii fgpgpvlsdr ftdsmimngh
  181 spisegfgar mnirfcpscl nvfnnvqenk dtsifsrray fadpaltlmh elihvlhgly
  241 gikisnlpit pntkeffmqh sdpvqaeely tfgghdpsvi spstdmniyn kalqnfqdia
  301 nrlnivssaq gsgidislyk qiyknkydfv edpngkysvd kdkfdklyka lmfgftetnl
  361 ageygiktry syfseylppi kteklldnti ytqnegfnia sknlktefng qnkavnkeay
  421 eeislehlvi yriamck  (SEQ ID NO: 22)
```

```
atgccggtgaacattaaatttaactataacgatccgattaacaacgatgatattattatg
atggaaccgtttaacgatccgggcccgggcacctattataaagcgtttcgcattattgat
cgcatttggattgtgccggaacgctttacctatggctttcagccggatcagtttaacgcg
agcaccggcgtgtttagcaaagatgtgtatgaatattatgatccgacctatctgaaaacc
gatgcggaaaaagataaatttctgaaaaccatgattaaactgtttaaccgcattaacagc
aaaccgagcggccagcgcctgctggatatgattgtggatgcgattccgtatctgggcaac
gcgagcacccgccggataaatttgcggcgaacgtggccaacgtgagcattaacaaaaaa
attattcagccgggcgcggaagatcagattaaaggcctgatgaccaacctgattatttttt
ggcccgggcccggtgctgagcgataactttaccgatagcatgattatgaacggccatagc
ccgattagcgaaggctttggcgcgcgcatgatgattcgcttttgcccgagctgcctgaac
gtgtttaacaacgtgcaggaaaacaaagataccagcatttttagccgccgcgcgtatttt
gcggatccggcgctgaccctgatgcatgaactgattcatgtgctgcatggcctgtatggc
attaaaattagcaacctgccgattaccccgaacaccaaagaatttttatgcagcatagc
gatccggtgcaggcggaagaactgtataccttggcggccatgatccgagcgtgattagc
ccgagcaccgatatgaacatttataacaaagcgctgcagaactttcaggatattgcgaac
cgcctgaacattgtgagcagcgcgcagggcagcggcattgatattagcctgtataaacag
atttataaaacaaatatgatttgtgtggaagatccgaacggcaaatatagcgtggataaa
gataaatttgataaactgtataaagcgctgatgtttggctttaccgaaaccaacctggcg
ggcgaatatggcattaaaacccgctatagctattttagcgaatatctgccgccgattaaa
accgaaaaactgctggataacaccatttatacccagaacgaaggctttaacattgcgagc
aaaaacctgaaaaccgaatttaacggccagaacaaagcggtgaacaaagaagcgtatgaa
gaaattagcctggaacatctcgtgatttatcgcattgccatgtgcaaatag  (SEQ ID NO: 21)
```

Figure 9K

METHODS FOR THE DELIVERY OF TOXINS OR ENZYMATICALLY ACTIVE PORTIONS THEREOF

RELATED APPLICATION

This application claims the benefit of U.S. Provisional Application No. 61/145,820, filed Jan. 20, 2009, entitled "Methods For The Delivery Of Toxins Or Enzymatically Active Portions Thereof" by Oyler, George A. et al.

The entire teachings of the above applications are incorporated herein by reference.

GOVERNMENT SUPPORT

This invention was supported, in whole or in part, by a grant AI30050 awarded by the National Institutes of Health. The government has certain rights in the invention.

BACKGROUND OF THE INVENTION

Prior to the present invention, cell-based assays for toxins such as *Botulinum* neurotoxins (BoNT) are limited to cells that contain the appropriate surface receptors used by the specific toxin to gain entry into cells. The efficiency of toxin entry into immortalized cell lines is often much poorer than that obtained with primary cultures, requiring the use of high concentrations of toxin and acceptance that a low percentage of the immortalized cells will become intoxicated. The use of holotoxin, the native toxin, in screening adds a substantial complication due to additional regulatory, safety and waste disposal issues.

Also, cell-based assays for toxins can be important in the development of therapeutic antitoxins and pharmacological antidotes, and in some aspects of diagnostic test development. Such assays are generally limited by several features. First, many cell lines are insensitive to a toxin, probably because they lack one or more surface receptors necessary for the toxin to enter the cell. Second, even when immortalized cell lines, such as neuroblastoma lines, are susceptible to intoxication, they are generally much less sensitive than primary neuronal cells. Thirdly, most cell lines that are sensitive to intoxication by one toxin are insensitive to most other toxins, limiting their broad utility. Finally, the use of holotoxin in the assays, that requires substantial safety and regulatory issues, severely complicate their use in high-throughput screening assays, e.g., it is difficult to get enough toxin to perform the assays.

Hence, a need exists for efficient ways to intoxicate one or more cells without having to use high concentrations of a holotoxin. A further need exists to intoxicate cells that are traditionally considered to be insensitive or refractory to toxins, and to intoxicate more than one cell type with the same toxin. Yet a further need exists to be able to intoxicate cells without using the entire toxin, but rather the enzymatically active portion thereof to avoid regulatory, safety and waste disposal issues.

SUMMARY OF THE INVENTION

The methods of the present invention relate to intoxicating a cell in vitro with a toxin or an enzymatically active domain or fragment thereof. As used herein, the term "toxin" refers to the holotoxin, enzymatically active domains of a toxin, an enzymatically active fragment of a toxin, and recombinant forms thereof. The steps include preparing a mixture of a (e.g., one or more) toxin or toxin fragment, and lipid or polymeric carrier, then exposing the cell (e.g., one or more cells or cell types) with the mixture to cause cell intoxication. In an embodiment, the toxin includes or can be derived from (e.g., having mutations, deletions, substitutions, truncations, and the like) any one or more of the following toxins: *botulinum* neurotoxin, tetanospasmin, tetrodotoxin, *Clostridium difficile* toxin Tcd A, Tcd B, *Clostridium* Lethal Toxin, Anthrax Lethal Factor and edema factor, Ricin, Exotoxin A, *Diphtheria, Cholera*, Tetanus toxins, Shiga toxin, latrotoxin and a combination thereof. Enzymatically active portions of these toxins can be used, as further described herein, and include, e.g., light chain or chain A of a toxin. The light chain or chain A, in an aspect, can have one or more mutations or deletions. In an embodiment, the *botulinum* neurotoxin (e.g., serotypes A-G including any isoforms) or light chain portion is used with the methods of the present invention. The lipid or polymeric carrier, in one aspect, includes one or more DNA transfection reagents (e.g., polyethylenimine (PEI), FuGene, Lipofectamine, or any combination thereof). In one embodiment, the cells are subjected to or come into contact with about 0.1 pM and about 1 µM of toxin or toxin fragment (e.g., about 1 nM and about 10 nM) for a length of time between about 5 minutes and about 72 hours (e.g., about 1 hour and about 6 hours).

The methods of the present invention relate to delivering a *botulinum* neurotoxin (e.g., one or more of the serotypes A-G and/or isoforms thereof) or an enzymatically active fragment thereof to the inside of a cell in vitro. The methods encompass contacting the toxin or enzymatically active fragment (e.g., toxin light chain protease) with a lipid or polymeric carrier prior to contacting the cell with the toxin or toxin fragment. These steps result in the cell being intoxicated with the *botulinum* neurotoxin or enzymatically active fragment thereof (e.g., light chain portion thereof). Steps of an embodiment of the invention further include assessing the level of cleavage of one or more of the following to determine the level of cell intoxication: a SNARE protein, synaptobrevin 2, syntaxin and SNAP 25.

Yet another aspect of the present invention includes methods of assessing an effect of a molecule, compound, drug, or condition, in vitro, on a cell intoxicated with a toxin or fragment thereof. The methods involve intoxicating one or more cells, as described herein, and subjecting the intoxicated cells to the molecule, compound, drug, or condition to be assessed, and assessing the effect on the intoxicated cells of said molecule, compound, drug, or condition. The test agent might be added before, during or after cell intoxication. Assessing the effect of the molecule, compound, drug or condition can be done using various methods of assessing toxin effects including, e.g., Fluorescence Resonance Energy Transfer (FRET) assays or release assays. The molecule, compound, drug or condition can be an antagonist or an agonist of the toxin. In one aspect, the effect is assessed by determining the percent cleavage of the toxin substrate such as SNAP25, or assessing the level of one or more substrate proteins, such as synaptobrevin (e.g., 1 and 2), and syntaxin 1a.

In the case of a FRET assay, the steps include labeling the toxin substrate with a donor fluorophore, to thereby obtain a treated toxin substrate, exciting the donor fluorophore; and determining resonance energy transfer of the treated toxin substrate to a control substrate, wherein a difference in resonance energy transfer of the treated toxin substrate as compared to the control substrate is indicative of toxin protease activity.

In the case of using a release assay, the methods of the present invention include utilizing an insulinoma cell line, which is subjected to the toxin and a lipid or polymeric carrier, as described herein, to obtain a mixture. The mixture is subjected to glucose under conditions that allow for insulin secretion to occur. The release of the toxin substrate is assessed by assessing the level of insulin secretion. An increase of insulin is indicative of an increase in toxin release, and a decrease of insulin is indicative of a decrease in toxin release.

The present invention further embodies systems or kits for delivering a toxin or toxin fragment to the inside of a cell in vitro. The systems or kits include one or more toxins, and one or more lipid or polymeric carriers (e.g., DNA transfection reagents). In an embodiment, the system or kit includes one or more cell lines, e.g., intoxicated with the toxin.

There are several advantages of the invention. The present invention dramatically increases the number of cell lines available for toxin assays and substantially broadens the range of toxins that can be assayed within these different cell lines. It will also increase the sensitivity of these cell lines to a toxin or toxin fragment which will improve their utility and ability to detect lower doses of the toxin. Furthermore, it allows rapid testing of enzymatically active mutants (LC active mutants of toxins) at physiologically relevant levels in the context of the mammalian cellular environment. More importantly, it should remove the need to use holotoxin (e.g., the entire toxin) to achieve intoxication, thereby eliminating the safety and regulatory issues that otherwise substantially complicate holotoxin use in a high-throughput screen.

BRIEF DESCRIPTION OF THE DRAWINGS

FIG. 3 is a photograph of a western blot showing DNA transfection reagent that mediated BoNT/A intoxication by Neuro2a cells is toxin concentration dependent. Neuro2a cells were exposed to 10 nM, 1 nM and 0.1 nM of BoNT/A toxin for 24 hrs with (+) or without (−) pre-incubation with FuGene-HD transfection reagent. Cell extracts were prepared and the extent of BoNT/A intoxication was measured by Western blotting to monitor SNAP25 cleavage.

FIG. 7 is a photograph of a western blot showing that Bafilomycin inhibits DNA transfection reagent-mediated enhancement of BoNT/A holotoxin and Lc internalization into cells. Primary cells RCGN, neuronal cell lines Neuro2a, M17 and non-neuronal cell lines 293HEK, HIT-T15 were treated with Bafilomycin for 2 hrs and washed with DPBS before exposed to 10 nM of BoNT/A toxin for 4 or 24 hrs or 30 nM of Lc438 for 24 hrs + or − the FuGene transfection reagent. Control cells were incubated with 10 nM of BoNT/A toxin or 30 nM of Lc438 + or − the FuGene transfection reagent without pre-exposure cells with Bafilomycin. Cell extracts were prepared after BoNT/A or Lc438 exposure and subjected to SDS-PAGE. Bafilomycin effect on BoNT/A or Lc438 internalization was detected by comparing the presence of 24 KDa SNAP25 by Western blotting.

FIGS. 9A-K is a schematic of nucleic acid and amino acid sequences of BoNT/A1 LC (SEQ ID NO: 1 and 2), BoNT/A2 LC (SEQ ID NO: 3 and 4), BoNT/A3 LC (SEQ ID NO: 5 and 6), *Botulinum* B1 Okra P10844 (SEQ ID NO: 7 and 8), *Botulinum* B2 Eklund 17B (SEQ ID NO: 9 and 10), Neurotoxin type C1 *Clostridium botulinum* (BoNT/C1) LC (SEQ ID NO: 11 and 12), Neurotoxin type D *Clostridium botulinum* (BoNT/D) LC (SEQ ID NO: 13 and 14), Neurotoxin type E *Clostridium botulinum* (BoNT/E) LC (SEQ ID NO: 15 and 16), Neurotoxin type F *Clostridium botulinum* (BoNT/F1) LC (SEQ ID NO: 17 and 18), Neurotoxin type F *Clostridium baratii* (BoNT/F2) (SEQ ID NO: 19 and 20), Neurotoxin type G *Clostridium botulinum* (BoNT/G) (SEQ ID NO: 21 and 22).

DETAILED DESCRIPTION OF THE INVENTION

Figure 1:
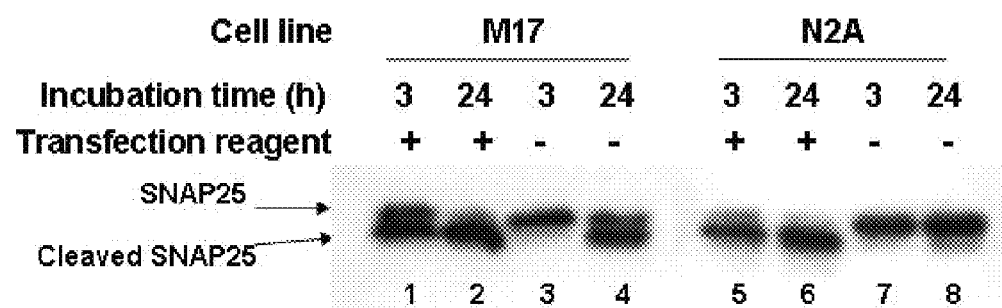
FIG. 1 is a photograph of a western blot showing pre-incubation of BoNT/A with a DNA transfection reagent that enhances BoNT/A intoxication of two neuroblastoma cell lines. Neuroblastoma cells M17 or Neuro2a (N2a) were incubated with 10 nM BoNT/A for 3 or 24 hrs with (+) or without (−) pre-incubation of toxin with FuGene-HD transfection reagent. Cells were washed and cultured a further 24 hours, then protein was extracted, resolved by SDS-PAGE and a Western blot was performed to detect SNAP25. The extent of BoNT intoxication is measured by the extent of SNAP25 cleavage by BoNT/A protease. The native 25 kDa SNAP25 and the 24 kD cleavage product of BoNT/A are indicated by arrows.
Figure 2:
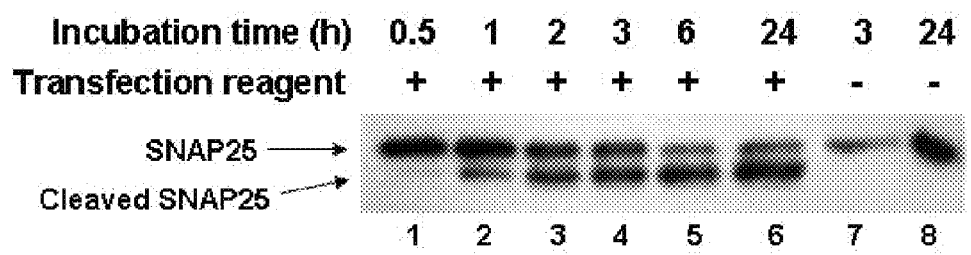
FIG. 2 is a photograph of a western blot showing a DNA transfection reagent that facilitates rapid BoNT/A internalization by Neuro2a cells. Neuro2a cells were exposed to 10 nM BoNT/A toxin for 0.5, 1, 2, 3, 6 or 24 hrs with (+) or without (−) pre-incubation of toxin with FuGene-HD transfection reagent. After the indicated toxin exposure time, cells were harvested and cell extracts were prepared. Proteins were resolved by SDS-PAGE and SNAP25 cleavage was detected by Western blotting.

A description of preferred embodiments of the invention follows.

The present invention relates to methods for intoxicating a cell with a toxin, or an enzymatically active fragment thereof. The methods of the present invention allow one to easily and to a greater extent intoxicate cells with toxin or toxin fragment. In an embodiment, the methods of the present invention allow for the intoxication of cells with only enzymatically active fragments of the toxin, rather than the entire toxin. Utilizing only the functional or enzymatically active portion of the toxin rather than the entire toxin is advantageous because the enzymatically active portion is easier to obtain and safer to work with. Furthermore, the methods and systems of the present invention allow one to intoxicate toxin insensitive cells, cells that could not otherwise be intoxicated.

Accordingly, the methods of the present invention involve intoxicating a cell with a toxin, the enzymatically active fragment of the toxin, or a recombinant SNARE endoprotease. Intoxicating a cell refers to getting the toxin or an enzymatically active fragment thereof inside the cell. In particular, intoxicating a cell refers to bringing the toxin or an enzymatically active portion thereof past the cellular membrane and to its site of action within the cell. In an embodiment, the toxin is carried from the cell membrane into the cell with an endosome via endocytosis. With respect to the present invention, endocytosis is a process where cells engulf the toxin or fragment thereof at the cell membrane. Once inside the cell, the endosome releases the toxin enzyme active domain into the cytosol, the internal fluid of the cell. After release, the toxin enzyme active domain is free to cleave SNARE proteins, or undergo other cleavages or mechanisms of action. As further described herein, the cell based assays measure the release of the toxin enzyme active domain into the cytosol, as well as measure cleavage of various proteins. These measurements are performed to determine the toxin or its fragment's ability to intoxicate the cell, and/or assess the effect of one or more compounds, molecules, drugs, or conditions on the toxin or fragment thereof.

Toxin, Enzymatically Active Portion Thereof, and the Recombinant Snare Endoprotease The toxin that is used in the present invention refers to the native toxin or the enzymatically active portion of the toxin. The toxin used for preparing cells for a cell-based assay can be any toxin known or later discovered or developed. A toxin is a molecule, generally produced by a living cell or organism, that gets into the cell and causes disease or injury. Certain toxins come from animals such as spiders, snakes, pufferfish, scorpions, jellyfish, and bees. Types of toxins include, e.g., neurotoxins (e.g., *Botulinum* neurotoxin), and other toxins which effect other cell types in addition to neurons such as cholera toxin, clostridial difficile toxin (Tcd), anthrax lethal factor and edema factor. A neurotoxin is a toxin that affects neurons. Several toxins generally interact with membrane proteins such as ion channels (e.g., sodium, potassium, or calcium channels). A common effect is paralysis, which often sets in very rapidly. Examples of neurotoxins include *botulinum* neurotoxin (BoNT), tetanospasmin, tetrodotoxin,. Other toxins implicated by the invention are, *Clostridium difficile* toxin Tcd A, Tcd B, *Clostridium* Lethal Toxin, Anthrax Lethal Factor and edema factor, Ricin, Exotoxin A, *Diphtheria*, *Cholera*, Tetanus toxins, Shiga toxin, latrotoxin and a combination thereof.

In an embodiment, BoNT or an enzymatically active portion thereof is used. BoNT is a neurotoxin protein produced by the bacterium *Clostridium botulinum* . There are at least seven different BoNT serotypes (A to G), and some of the serotypes have various isotypes (e.g., three isotypes of serotype A have been described). Generally, the BoNT has two chains, a heavy chain (e.g., about 100-kDa) and a light chain (e.g., about 50-kDa) joined by a disulfide bond. The heavy chain is a cell binding/translocation domain that allows for the toxin to bind to and enter the cell.

The light chain is an enzyme (e.g., a protease) that cleaves a fusion protein (e.g., SNAP-25, syntaxin or synaptobrevin) at a neuromuscular junction, preventing vesicles from anchoring to the membrane to release acetylcholine. By inhibiting acetylcholine release, the toxin interferes with nerve impulses and causes paralysis of muscles, seen in botulism.

The term "toxin" or "fragment" for use with the present invention includes derivatives of a toxin's enzymatically active portion. A "derivative" refers to a molecule with toxin enzymatic activity but contains one or more chemical or functional alterations thereof, as compared to the native enzymatic portion. For instance, the *botulinum* toxin light chain protease can be modified so that one or more of its amino acid residues is deleted, modified, replaced, or truncated. For instance, the *botulinum* toxin light chain protease can be modified in a way such that, for instance, the modification enhances its properties or decreases undesirable side effects, but that still retains the desired *botulinum* toxin activity. The *botulinum* toxin can be derived from any of the *botulinum* toxin serotypes and/or isoforms produced by the bacterium. Alternatively, the *botulinum* toxin can be a toxin prepared using recombinant or synthetic chemical techniques (e.g., a recombinant peptide, a fusion protein, or a hybrid neurotoxin, as prepared from subunits or domains of different *botulinum* toxin serotypes). Additionally, the *botulinum* toxin can be in the form of a *botulinum* toxin precursor, which can itself be non-toxic, for instance a non-toxic zinc protease that becomes toxic on proteolytic cleavage.

"Enzymatically active" portion or fragment of the toxin refers to the portion or domain of the toxin that normally gets into the inside of the cell (e.g., in the endosome or cytosol) and is active. Toxins are often made up of at least two parts, a cell-binding/translocation domain, and an enzymatically active domain. In the BoNT, the enzymatically active domain is often referred to as the "light chain." However, the enzymatically active domain for other toxins can have other names. For example, with the ricin toxin, the enzymatically active domain is the "A" Chain. The cell-binding/translocation domain facilitates binding of the toxin to the cell membrane and transporting the toxin across the cellular membrane. For certain toxins like the BoNT, this domain is referred to as the heavy chain. For other toxins, such as ricin, this is referred to as the B Chain.

In an embodiment, enzymatically active refers to a protein that causes the cleavage of one or more proteins in the cell, which in turn causes toxic effects. In the case of certain toxins, the enzymatically active domain cleaves a SNARE ("Soluble NSF Attachment REceptor") protein. SNARE proteins are a large protein superfamily consisting of several members. The primary role of SNARE proteins is to mediate fusion of cellular transport vesicles with the cell membrane. The core SNARE complex is formed by four α-helices contributed by synaptobrevin, syntaxin and SNAP-25. Different toxins, serotypes of a certain toxin, or cell types will involve cleavage of different SNARE proteins. Tetanospasmin, e.g., is the neurotoxin produced by the vegetative spore of *Clostridium tetani* and causes tetanus. BoNT A, C, and E cleave SNAP-25, in addition BoNT C cleaves syntaxin 1. BoNT B, D, F, G and tetanus toxin cleave VAMP 1 and 2 isoforms.

*Botulinum* toxin is generally considered to be a zinc-dependent protease. As described herein, enzymatic activity resides generally in the light chain of the molecules. These enzymes cleave SNARE proteins, synaptobrevin 1 and 2, syntaxin and SNAP 25, which form the core of a complex involved in the fusion of transmitter-containing vesicles with the plasma membrane. Prior to fusion, the SNARE proteins in the vesicle and plasma membrane interact forming a complex which contracts with an increase in the intracellular calcium concentration, pulling the vesicle close to the plasma membrane. Interaction between lipids in the two membranes allows the vesicle and nerve terminal active zone to fuse. During this fusion, the contents of the vesicles, mainly neurotransmitters, are released, and the inner surface of the vesicles is exposed to the synaptic cleft. If one of the SNARE proteins is cleaved by a neurotoxin, complex formation cannot occur and fusion is interrupted.

The present invention further involves using a toxin substrate of a recombinant SNARE protein. Any one of the SNARE proteins can be made using DNA recombinant technology. With respect to the BoNT serotypes, the light chain for each serotype has an amino acid sequence, or is encoded by a nucleic acid sequence as shown in FIGS. 9A-C. The present invention specifically relates to intoxicating cells with the light chain of any of the BoNT serotypes, as well as any recombinant, mutated, truncated or deleted portions thereof. As such, the toxin or fragment thereof can be the recombinant form of any toxin, the enzymatically active portion thereof (e.g., the light chain of a BoNT serotype), or a SNARE protein. The toxin substrate can be made from recombinant DNA which transcribes the desired amino acid sequence of the toxin or fragment thereof. The recombinant nucleic acid sequence can be a nucleotide "variant" of any toxin or fragment thereof (e.g., toxin, enzymatically active portion thereof, or SNARE protein). A variant is a sequence that differs from the known nucleotide sequence for that molecule in having a truncation, and/or one or more nucleotide deletions, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

Cells Intoxicated with the Toxin or Fragment Thereof

An aspect of the invention are the cells that are intoxicated with the toxin or enzymatically active fragment thereof. The toxin or toxin enzyme active fragment and the lipid or polymeric carrier come into contact with one or more cells which allows the toxin to enter the cells. When a cell is intoxicated with the toxin, in an aspect, the cell is prepared for a cell based assay, e.g., to evaluate a drug candidate. "Preparing" a cell refers to intoxicating one or more cells or cell types with a toxin or fragment so that the cell is ready for a cell based assay.

Various cell types can be used with the methods of the present invention. In an embodiment, cell types include those that are sensitive to intoxication by a toxin as well as those that are insensitive. Any cell type known or later discovered or developed can be used with the present invention so long as the cell comes into contact with the toxin or fragment thereof. Cells that are normally insensitive include all non-neuroendocrine immortalized cell lines, many neuroblastoma, and neuronal cell lines and a variety of stem cells.

Aspects of the present invention provide, in part, a cell that can be intoxicated by a toxin using a lipid or polymeric carrier. As used herein, the term "cell," means any eukaryotic cell that can be intoxicated with a toxin using a lipid or polymeric carrier, as described herein. The term cell encompasses cells from a variety of organisms, such as, e.g., murine, rat, porcine, bovine, equine, primate and human cells; from a variety of cell types such as, e.g., neural and non-neural; and can be isolated from or part of a heterogeneous cell population, tissue or organism. Cells useful in aspects of the present invention can include, e.g., primary cells; cultured cells; established cells; normal cells; transformed cells; tumor cells; infected cells; proliferating and terminally differentiated cells; and stably or transiently transfected cells, including stably and transiently transfected cells.

A cell that is intoxicated by a toxin or toxin enzyme active fragment is a cell that has internalized the toxin enzyme active domain in a manner such that the natural substrate of the enzyme within the cell can be acted on by the enzyme. Cells utilized in the methods of the present invention include any cell containing the substrate of a toxin enzyme active domain, both neuronal and non-neuronal cells.

Neuronal cells useful in aspects of the invention include, without limitation, primary neuronal cells; immortalized or established neuronal cells; transformed neuronal cells; neuronal tumor cells; stably and transiently transfected neuronal cells and further include, yet are not limited to, mammalian, murine, rat, primate and human neuronal cells. Examples of neuronal cells useful in aspects of the invention include, e.g., peripheral neuronal cells, such as, e.g., motor neurons and sensory neurons; and CNS neuronal cells, such as, e.g., spinal cord neurons like embryonic spinal cord neurons, dorsal root ganglia (DRG) neurons, cerebral cortex neurons, cerebellar neurons, hippocampal neurons and motor neurons. Neuronal cells useful in the invention can be, for example, central nervous system (CNS) neurons; neuroblastoma cells; motor neurons, hippocampal neurons or cerebellar neurons and further can be, without limitation, Neuro-2A, SH-SY5Y, NG108-15, N1E-115 or SK-N-DZ cells. These and additional primary and established neurons can be useful in carrying out the methods of the present invention.

Neurons useful in aspects of the invention include, without limitation, primary cultures such as primary cultures of embryonic dorsal root ganglion (DRG) neurons. As one example, primary cultures of embryonic rat DRG neurons are described in Mary J. Welch et al., Sensitivity of embryonic rat dorsal root ganglia neurons to *Clostridium botulinum* neurotoxins, 38(2) Toxicon 245 258 (2000); and primary cultures of fetal spinal cord neurons, for example, primary cultures of murine fetal spinal cord neurons are described in Elaine A. Neale et al., *Botulinum* neurotoxin A blocks synaptic vesicle exocytosis but not endocytosis at the nerve terminal, 147(6) J. Cell Biol. 1249-1260 (1999), and John A. Chaddock et al., Inhibition of vesicular secretion in both neuronal and non-neuronal cells by a retargeted endopeptidase derivative of *Clostridium botulinum* neurotoxin type A, 68(5) Infect. Immun. 2587-2593 (2000).

Neuronal cell lines useful in carrying out the methods of the present invention include, without limitation, neuroblastoma cell lines, neuronal hybrid cell lines, spinal cord cell lines, central nervous system cell lines, cerebral cortex cell lines, dorsal root ganglion cell lines, hippocampal cell lines and pheochromocytoma cell lines.

Neuroblastoma cell lines, such as, e.g., murine, rat, primate or human neuroblastoma cell lines can be useful in aspects of the invention. Neuroblastoma cell lines useful in aspects of the invention include, without limitation, BE(2)-C (ATCC CRL-2268; ECACC 95011817), BE(2)-M17 (ATCC CRL-2267; ECACC 95011816), C1300 (ECACC 93120817), CHP-212 (ATCC CRL-2273), CHP-126 (DSMZ ACC 304), IMR 32 (ATCC CRL-127; ECACC 86041809; DSMZ ACC 165), KELLY (ECACC 92110411; DSMZ ACC 355), LA-N-2, see, e.g., Robert C. Seeger et al., Morphology, growth, chromosomal pattern and fibrinolytic activity of two new human neuroblastoma cell lines, 37(5) Cancer Res. 1364-1371 (1977); and G. J. West et al., Adrenergic, cholinergic, and inactive human neuroblastoma cell lines with the action-potential Na+ ionophore, 37(5) Cancer Res. 1372-1376 (1977), MC-IXC (ATCC CRL-2270), MHH-NB-11 (DSMZ ACC 157), N18Tg2 (DSMZ ACC 103), N1E-115 (ATCC CCL-2263; ECACC 88112303), N4TG3 (DSMZ ACC 101), Neuro-2A (ATCC CCL-131; ECACC 89121404; DSMZ ACC 148), NB41A3 (ATCC CCL-147; ECACC 89121405), NS20Y (DSMZ ACC 94), SH-SY5Y (ATCC CRL-2266; ECACC 94030304; DSMZ ACC 209), SIMA (DSMZ ACC 164), SK-N-DZ (ATCC CRL-2149; ECACC 94092305), SK-N-F1 (ATCC CRL-2142, ECACC 94092304), SK-N-MC (ATCC HTB-10, DSMZ ACC 203) and SK-N-SH (ATCC HTB-11, ECACC 86012802).

Neuronal hybrid cell lines, such as, e.g., murine, rat, primate and human hybrid neuronal cell lines can be useful in aspects of the invention. Such hybrid cell lines include neuroblastoma/glioma hybrids, such as, e.g., N18 (ECACC 88112301), NG108-15 (ATCC HB-12317, ECACC 88112302) and NG115-401L (ECACC 87032003); neuroblastoma/motor neuron hybrids, such as, e.g., NSC-19 and NSC-34, which express motor neuron characteristics, display a multipolar neuron-like phenotype, express high levels of choline acetyltransferase (CHAT), generate action potentials, express neurofilament triplet proteins and synthesize, store and release acetylcholine., see, e.g., N. R. Cashman et al., Neuroblastoma.times.spinal cord (NSC) hybrid cell lines resemble developing motor neurons, 194(3) Dev. Dyn. 209-221 (1992); and Christopher J. Eggett et al., Development and characterisation of a glutamate-sensitive motor neuronal cell line, 74(5) J. Neurochem. 1895-1902 (2000); neuroblastoma/root ganglion neuron hybrids, such as, e.g., F11, see, e.g., Doros Platika et al., Neuronal traits of clonal cell lines derived by fusion of dorsal root ganglia neurons with neuroblastoma cells, 82(10) Proc. Natl. Acad. Sci. U.S.A. 3499-3503 (1985), ND-E (ECACC 92090915), ND-U1 (ECACC 92090916), ND7/23 (ECACC 92090903), ND8/34 (ECACC 92090904) and ND27 (ECACC 92090912); neuroblastoma/hippocampal neuron hybrids, such as, e.g., HN-33, see, e.g., Henry J. Lee et al., Neuronal properties and trophic activities of immortalized hippocampal cells from embryonic and young adult mice. 10(6) J. Neurosci. 1779-1787 (1990). In further aspects of this embodiment, a neuroblastoma/motor neuron hybrid can be, e.g., NSC-19 and NSC-32. In further aspects of this embodiment, a neuroblastoma/root ganglion neuron hybrid can be, e.g., F11, ND-E, ND-U1, ND7/23, ND8/34 and ND27. In further aspects of this embodiment, a neuroblastoma/hippocampal neuron hybrid can be, e.g., HN-33.

Spinal cord cell lines, such as, e.g., murine, rat, primate or human spinal cord cell lines can be useful in aspects of the invention and include, without limitation, TE 189.T (ATCC CRL-7947) and M4b, see, e.g., Ana M. Cardenas et al., Establishment and characterization of immortalized neuronal cell lines derived from the spinal cord of normal and trisomy 16 fetal mice, an animal model of Down syndrome, 68(1) J. Neurosci. Res. 46-58 (2002). As an example, a human spinal cord cell line can be generated from precursors of human embryonic spinal cord cells (first trimester embryos) that are immortalized with a tetracycline repressible v-myc oncogene as described in Ronghao Li et al., Motoneuron differentiation of immortalized human spinal cord cell lines, 59(3) J. Neurosci. Res. 342-352 (2000). Such cells can be expanded indefinitely in proliferative growth conditions before rapid differentiation (4-7 days) into functional neurons that express neuronal phenotypic markers such as choline acetyltransferase. As another example, a murine spinal cord cell line can be prepared by immortalizing an embryonic spinal cord culture using transforming media. Such a spinal cord cell line can be, for example, the murine M4b line and can express neuronal markers such as NSE, synaptophysin, MAP 2 and choline acetyltransferase, and can release acetylcholine upon appropriate stimulation, see, e.g., Cardenas et al., supra, (2002).

Central nervous system (CNS) cell lines, such as, e.g., murine, rat, primate and human CNS cell lines, can be useful in aspects of the invention. A useful CNS cell line can be, for example, a human CNS cell line immortalized with a tetracycline repressible v-myc oncogene as described in Dinah W. Sah et al., Bipotent progenitor cell lines from the human CNS, 15(6) Nat. Biotechnol. 574-580 (1997). Upon repression of the oncogene, the cells differentiate into neurons.

Cerebral cortex cell lines, such as, e.g., murine, rat, primate and human cerebral cortex cell lines, can be useful in aspects of the invention and include, without limitation, CNh, see, e.g., Ana M. Cardenas et al., Calcium signals in cell lines derived from the cerebral cortex of normal and trisomy 16 mice, 10(2) Neuroreport 363-369 (1999), HCN-1a (ATCC CRL-10442) and HCN-2 (ATCC CRL-10742). As an example, murine cortex primary cultures from 12-16 days embryos can be immortalized by culturing the cells in conditioned media from a rat thyroid cell line that induces transformation in vitro. The immortalized cells can be differentiated into neurons expressing neuronal markers using the appropriate media; these differentiated cells express choline acetyltransferase and secrete acetylcholine and glutamate in response to depolarization and nicotine stimulation, see, e.g., David D. Allen et al., Impaired cholinergic function in cell lines derived from the cerebral cortex of normal and trisomy 16 mice, 12(9) Eur. J. Neurosci. 3259-3264 (2000).

Dorsal root ganglia cell lines, such as, e.g., murine, rat, primate and human dorsal root ganglia cell lines, can be useful in aspects of the invention and include, without limitation, G4b, see, e.g., David D. Allen et al., A dorsal root ganglia cell line derived from trisomy 16 fetal mice, a model for Down syndrome, 13(4) Neuroreport 491-496 (2002). Embryonic dorsal root ganglia primary cultures can be immortalized with transforming conditioned media as described above. Upon differentiation, the cell line exhibits neuronal traits and lacks glial markers by immunohistochemistry. Release of neurotransmitters such as acetylcholine can be induced in response to potassium and nicotine, see, e.g., Allen et al., supra, (2002).

Hippocampal cell lines, such as, e.g., murine, rat, primate and human hippocampal lines can be useful in aspects of the invention and include, without limitation, HT-4, see, e.g., K.

Frederiksen et al., Immortalization of precursor cells from the mammalian CNS, 1(6) Neuron 439-448 (1988) and HT-22, see, e.g., John B. Davis and Pamela Maher, Protein kinase C activation inhibits glutamate-induced cytotoxicity in a neuronal cell line, 652(1) Brain Res. 169-173 (1994). As an example, the murine hippocampal cell line HT-22 can be useful in the invention. As a further non-limiting example, the immortalized HN33 hippocampal cell line can be useful in the invention. This hippocampal cell line was derived from the fusion of primary neurons from the hippocampus of postnatal day 21 mice with the N18TG2 neuroblastoma cell line, and, when differentiated, shares membrane properties with adult hippocampal neurons in primary culture, see, e.g., Henry J. Lee et al., Neuronal Properties and Trophic Activities of Immortalized Hippocampal Cells from Embryonic and Young Adult Mice, 19(6) J. Neurosci. 1779-1787 (1990); and Henry J. Lee et al., Immortalized young adult neurons from the septal region: generation and characterization, 52(1-2) Brain Res. Dev Brain Res. 219-228 (1990).

A variety of non-neuronal cells are used to carry out the steps of the present invention. Non-neuronal cells useful in aspects of the invention include, e.g., primary non-neuronal cells; immortalized or established non-neuronal cells; transformed non-neuronal cells; non-neuronal tumor cells; stably and transiently transfected non-neuronal cells and further include, yet are not limited to, mammalian, murine, rat, primate and human non-neuronal cells. Non-neuronal cells useful in aspects of the invention further include, for example, any of the following primary or established cells: anterior pituitary cells; adrenal cells, such as, e.g., chromaffin cells of the adrenal medulla; pancreatic cells, such as. e.g., pancreatic acinar cells, pancreatic islet cells and insulinoma HIT or INS-1 cells; ovarian cells, such as, e.g., steroid-producing ovarian cells; kidney cells, such as. e.g., inner medullary collecting duct (IMCD) cells; stomach cells, such as, e.g., enterochromaffin cells; blood cells, such as. e.g., eurythrocytes, leucocytes, platelets, neutrophils, eosinophils, mast cells; epithelial cells, such as. e.g., those of the apical plasma membrane; fibroblasts; thyroid cells; chondrocytes; muscle cells; hepatocytes; glandular cells such as, e.g., pituitary cells, adrenal cells, chromaffin cells; and cells involved in glucose transporter (GLUT4) translocation. See e.g., US Publication No.: 20080003240.

Accordingly, an aspect of the present invention relates to intoxicating cells that are insensitive to or refractory to the toxin or fragment thereof without the presence of a lipid or polymeric carrier. Insensitive cells are cells that do not become intoxicated or become intoxicated at low levels, with holotoxin or fragment thereof in conditions that occur generally in nature, or absent a lipid or polymeric carrier. Refractory cells, as used herein, are cells that do not become intoxicated or resist intoxication under the same conditions.

Lipid or Polymeric Carrier

The present invention utilizes one or more lipid carriers, polymeric carriers, or a combination thereof to intoxicate the cell with the toxin or fragment thereof. A "lipid carrier" or "polymeric carrier” refers to a carrier that allows the toxin or fragment thereof to pass through the cellular membrane. Lipofection is generally used to inject genetic material into a cell by means of liposomes have a phospholipid bilayer which merge with the cell membrane. However, the methods of present invention unexpectedly allow for the delivery of a toxin polypeptide, rather than nucleic acid molecules. The carrier of the present invention, in an aspect, can be cationic, anionic or neutrally charged. Examples of lipid carriers include Lipofectamine (Invitrogen Corporation, Carlsbad, Calif.), cardiolipins, or other cationic, anionic or neutrally charged polymers.

A polymeric carrier is a carrier that has a repeating backbone, which can be linear or branched. In an embodiment, the linear backbone can have a primarily hydrocarbon backbone, interspersed by heteroatoms such nitrogen, oxygen, sulfur, silicon and phosphorus. Additionally, the backbone can also be a polymer of other repeating units such as amino acids, poly(ethyleneoxy), poly(propyleneamine), polyalkyleneimine, and a combination thereof. The polymeric carrier can be configured to include chemical groups to be positively charged, negatively charged, or have no overall charge. In another embodiment, the backbone has attached a plurality of side-chain moieties (e.g., ammonium groups, pyridinium groups, phosphonium groups, sulfonium groups, guanidinium groups, or amidinium groups) or are otherwise branched. See WO/2006/094263 for positively charged carriers.

In another embodiment, the carrier is a polylysine with positively charged branching groups attached to the lysine side-chain amino groups. The polylysine is commercially available e.g., from Sigma Chemical Company, St. Louis, Mo. In another embodiment, the carrier can have a polyethyleneimine (PEI) backbone. For example; polylysine or polyethyleneimine (PEI) backbone, which may be linear or branched, can be used and have a molecular weight ranging from 0.5 kD to 250 kD. Other polycationic polymer carriers could also be used. Another example of a polymeric carrier includes Fugene (Hoffmann LaRoche, Ltd.).

DNA uptake facilitating agent is a reagent that allows nucleic acid to be transfected into a cell. It is generally used to get recombinant DNA into the cell. The present invention surprisingly found the DNA uptake facilitating agent assists in getting a totally different type of molecule, a toxin or fragment thereof, into the cell. See Exemplification. Any DNA uptake facilitating agent can be used, including those known in the art and those later developed or discovered. Many DNA uptake facilitating agents are carriers that cause DNA to get into a cell e.g., via endocytosis, and, in an embodiment, are generally lipid carriers or polymeric carriers. Examples of DNA uptake facilitating agents includes transfection reagents such as Lipofectamine, Dojindo Hilymax, Fugene, jetPEI, Effectene or DreamFect. As such, the present invention involves contacting a cell/toxin mixture with a DNA uptake facilitating agent, a lipid carrier, a polymeric carrier and/or any combination thereof.

The present invention involves subjecting the toxin to contact with the lipid or polymeric carrier prior to exposure to the cell or cells. “Subjecting” or “exposing” the mixture to the carrier refers to preparing the mixture for a sufficient time and in an amount that allows for the intoxication of the cell with the toxin or fragment thereof.

In an embodiment, the amount of toxin substrate will depend in part on the type of cell based assay is being performed, the compound being assayed. The amount of the toxin or fragment thereof used, in an embodiment, ranges between about 0.1 pM and about 1 μM., and preferably between about 1 nM and about 10 nM.

The amount of the carrier used depends on various factors such as the amount of the length of time the mixture will be exposed to the carrier, the potency or effectiveness of the carrier, the recommended dosage of DNA transfection for use in nucleic acid transfection, the type of medium, amount of toxin or fragment thereof, and temperature. The amount of the carrier used, in an embodiment, ranges between about 0.1 pM and about 1 μM., and preferably between about 1 nM and about 10 nM.

The amount of time the mixture is subjected to the carrier for the present invention relates to the amount of time sufficient to allow the cell to be intoxicated with the toxin substrate. In an embodiment, the amount of time for subjecting the carrier to the mixture ranges from about 5 minutes and about 72 hours, and preferably from about 1 hour and about 6 hours.

Cell Based Assays:

The methods of the present invention can be used with any type of cell based assay where toxin intoxication of a cell is desirable. Cell based assays can be used to assess the effect of a molecule, drug, compound or condition on a cell intoxicated with the toxin or fragment thereof. Varying concentrations of molecules or drugs can be used to determine their effect on a cell intoxicated with the toxin. The molecule or drug being assessed includes those that are antagonists and agonists. An antagonist is a molecule that inhibits the toxin enzymatic activity (e.g., cleavage of a SNARE protein) or prevents release of the toxin substrate from the endosome to its site of action. An agonist is a molecule that increases these effects. In an embodiment, cell based assays are those that can measure the extent of intoxication of the toxin, its ability to enzymatically act on its substrate, and/or extent of release of the toxin substrate by the endosome.

Aspects of the present invention provide, in part, detecting the presence of enzymatic activity of contacted cell relative to a control cell, where a difference in the activity of the contacted cell as compared to the control cell is indicative of enzymatic activity. As used herein, the term "control cell" means a cell of the same or similar type as the contacted cell and grown under the same conditions but which is not contacted with any sample or is contacted with a defined negative sample or a defined positive sample. A variety of control cells are useful in the methods described herein and a control cell can be a positive control cell or a negative control cell. A control cell can be, for example, a negative control cell e.g., that lacks the toxin or toxin fragment. A control cell also can be, for example, a positive control cell that is fully intoxicated with the toxin.

A wide variety of assays can be used to determine the presence of toxin activity, including direct and indirect assays for toxin uptake. Assays that determine toxin binding or uptake properties can be used to assess activity. Such assays include, e.g., cross-linking assays using labeled toxin. Other assays include immunocytochemical assays that detect toxin binding using labeled or unlabeled antibodies, see, e.g., Atsushi Nishikawa et al., The receptor and transporter for internalization of *Clostridium botulinum* type C progenitor toxin into HT-29 cells, 319(2) Biochem. Biophys. Res. Commun. 327-333 (2004) and immunoprecipitation assays, see, e.g., Yukako Fujinaga et al., Molecular characterization of binding subcomponents of *Clostridium botulinum* type C progenitor toxin for intestinal epithelial cells and erythrocytes, 150(Pt 5) Microbiology 1529-1538 (2004). Antibodies useful for these assays include antibodies can be made for the toxin enzyme domain modified substrate, such as a cleaved SNARE protein, and its existence and level can be determined. If the antibody is labeled, the binding of the molecule can be detected by various means, including Western blotting, direct microscopic observation of the cellular location of the antibody, measurement of cell or substrate-bound antibody following a wash step, or electrophoresis, employing techniques known to those of skill in the art. If the antibody is unlabeled, one can employ a labeled secondary antibody for indirect detection of the bound molecule, and detection can proceed as for a labeled antibody. These and similar assays that determine cleavage of a SNARE protein or other proteins normally cleaved by the toxin can be used to determine intoxication of the toxin.

Assays that monitor the release of a molecule after exposure to toxin or toxin thereof can also be used to assess for the presence of toxin activity. For example, an insulin release assay disclosed herein can monitor the release of a molecule after exposure to some toxins, and thereby be useful in assessing whether intoxication has occurred. Other assays include methods that measure inhibition of radio-labeled catecholamine release from neurons, such as, e.g., $^3$H noradrenaline or $^3$H dopamine release, see e.g., A Fassio et al., Evidence for calcium-dependent vesicular transmitter release insensitive to tetanus toxin and *botulinum* toxin type F, 90(3) Neuroscience 893-902 (1999); and Sara Stigliani et al., The sensitivity of catecholamine release to *botulinum* toxin C1 and E suggests selective targeting of vesicles set into the readily releasable pool, 85(2) J. Neurochem. 409-421 (2003), or measures catecholamine release using a fluorometric procedure, see, e.g., Anton de Paiva et al., A role for the interchain disulfide or its participating thiols in the internalization of *botulinum* neurotoxin A revealed by a toxin derivative that binds to ecto-acceptors and inhibits transmitter release intracellularly, 268(28) J. Biol. Chem. 20838-20844 (1993); Gary W. Lawrence et al., Distinct exocytotic responses of intact and permeabilised chromaffin cells after cleavage of the 25-kDa synaptosomal-associated protein (SNAP-25) or synaptobrevin by *botulinum* toxin A or B, 236(3) Eur. J. Biochem. 877-886 (1996); and Patrick Foran et al., *Botulinum* neurotoxin C1 cleaves both syntaxin and SNAP-25 in intact and permeabilized chromaffin cells: correlation with its blockade of catecholamine release, 35(8) Biochemistry 2630-2636 (1996); and methods that measure inhibition of hormone release from endocrine cells, such as, e.g., anterior pituitary cells or ovarian cells. Assays for determining toxin substrate cleavage or assessing release that are known in the art or later developed can be used with the methods of the present invention.

In a particular embodiment, after intoxicating the cell with the toxin or toxin fragment, an inhibition of insulin release assay can be used to determine the presence of toxin activity in cells that can secrete insulin; an inhibition of noradrenaline release assay can be used to determine toxin activity in cells that secrete noradrenaline; and an inhibition of estrogen release assay can be used to determine toxin activity in cells that secrete estrogen.

Assays that detect the cleavage of a toxin substrate can also be used to assess for the presence of toxin activity. In these assays, generation of a toxin cleavage-product is detected after toxin treatment. As an example, a SNAP-25 cleavage assay can detect the cleavage of a toxin substrate and thereby be useful in assessing toxin activity (see Exemplification). Other methods useful to detect the cleavage of a toxin substrate are described in, e.g., Lance E. Steward et al., FRET Protease Assays for *Botulinum* Serotype A/E Toxins, U.S. Patent Publication No. 2003/0143650 (Jul. 31, 2003); and Ester Fernandez-Salas et al., Cell-based Fluorescence Resonance Energy Transfer (FRET) Assays for Clostridial Toxins, U.S. Patent Publication 2004/0072270 (Apr. 15, 2004). These and similar assays for toxin substrate cleavage can be useful in assessing toxin activity.

Western blot analysis using an antibody that recognizes toxin SNAP-25-cleaved product can be used to determine the presence of toxin activity. Examples of anti-SNAP-25 antibodies useful for these assays include, e.g., rabbit polyclonal anti-SNAP25$_{197}$, antiserum pAb anti-SNAP25$_{197}$ #1 (Allergan, Inc., Irvine, Calif.), mouse monoclonal anti-SNAP-25 antibody SMI-81 (Sternberger Monoclonals, Lutherville, Md.), mouse monoclonal anti-SNAP-25 antibody CI 71.1 (Synaptic Systems, Goettingen, Germany), mouse monoclonal anti-SNAP-25 antibody CI 71.2 (Synaptic Systems, Goettingen, Germany), mouse monoclonal anti-SNAP-25 antibody SP12 (Abcam, Cambridge, Mass.), rabbit polyclonal anti-SNAP-25 antiserum (Synaptic Systems, Goettingen, Germany), and rabbit polyclonal anti-SNAP-25 antiserum (Abcam, Cambridge, Mass.).

Some toxins lead to cell death following intoxication and the toxin enzyme active domain acting on its substrate. Cell death might be the readout in such assays.

It is envisioned that a wide variety of processing formats can be used in conjunction with the methods of the present invention, including, for example, manual processing, partial automated-processing, semi-automated-processing, full automated-processing, high throughput processing, high content processing, and any combination thereof. High throughput processing is one preferred embodiment. See US Patent Publication No. 20080003240.

Fluorescence Resonance Energy Transfer (FRET)

The amount of intoxication by the toxin or fragment thereof can be determined, in an embodiment, using Fluorescence Resonance Energy Transfer (FRET). FRET is a distance-dependent interaction between the electronic excited states of two molecules in which excitation is transferred from a donor fluorophore to an acceptor without emission of a photon. The process of energy transfer results in a reduction (quenching) of fluorescence intensity and excited state lifetime of the donor fluorophore and, where the acceptor is a fluorophore, can produce an increase in the emission intensity of the acceptor. Upon cleavage of the toxin substrate of the invention, resonance energy transfer is reduced and can be detected, for example, by increased donor fluorescence emission, decreased acceptor fluorescence emission, or by a shift in the emission maxima from near the acceptor emission maxima to near the donor emission maxima. If desired, the amount of toxin substrate in a sample can be calculated as a function of the difference in the degree of FRET using the appropriate standards.

The toxin of the present invention can be formulated to contain a donor fluorophore; an acceptor having an absorbance spectrum overlapping the emission spectrum of the donor fluorophore; and a toxin recognition sequence that includes a cleavage site (e.g., a SNARE protein), wherein the cleavage site intervenes between the donor fluorophore and the acceptor and wherein, under the appropriate conditions, resonance energy transfer is exhibited between the donor fluorophore and the acceptor. Since, in an embodiment, the enzymatically active toxin fragment or SNARE recombinant protein contains the cleavage site.

A variety of donor fluorophores and acceptors, including fluorescent and non-fluorescent acceptors, are useful preparing the toxin substrates for carrying out the FRET assay. Donor fluorophores useful in the invention include, but are not limited to, fluorescein, ALEXA FLUOR® 488, DABCYL, and BODIPY®. Acceptors useful in the invention include, but are not limited to, tetramethylrhodamine, EDANS and QSY®. Exemplary donor fluorophoreacceptor pairs useful for inclusion in the toxin substrate of the present invention include, without limitation, fluorescein-tetramethylrhodamine, ALEXA FLUOR® 488-tetramethylrhodamine, DABCYL-EDANS, fluorescein-QSY® 7, and ALEXA FLUOR® 488-QSY® 7.

As used herein, the term "donor fluorophore" means a molecule that, when irradiated with light of a certain wavelength, emits light, also denoted fluorescence, of a different wavelength. The term fluorophore is synonymous in the art with the term "fluorochrome."

The term "acceptor," as used herein, refers to a molecule that can absorb energy from, and upon excitation of, a donor fluorophore and is a term that encompasses fluorophores as well as non-fluorescent molecules. An acceptor useful in a toxin substrate has an absorbance spectrum which overlaps the emission spectrum of a donor fluorophore. An acceptor useful in the invention generally also has rather low absorption at a wavelength suitable for excitation of the donor fluorophore.

When carrying out a FRET assay using the toxin substrate of the present invention, in an embodiment the toxin substrate contains a cleavage site that "intervenes" between a donor fluorophore and an acceptor having an absorbance spectrum which overlaps the emission spectrum of the donor fluorophore. Thus, the cleavage site is positioned in between the fluorophore and acceptor such that cleavage at the site results in a first molecule containing the fluorophore and a second molecule containing the acceptor. All or only a portion of the toxin recognition sequence can intervene between the donor fluorophore and acceptor.

The present invention also provides methods of determining toxin protease activity. Such methods are valuable, in part, because they are amenable to rapid screening and do not require separation of cleaved products from uncleaved substrate. Furthermore, the methods of the present invention are used with cells that have transfected with the toxin substrate using the carrier described herein. Such cells can be assayed in the presence or absence of molecules, compounds, drugs, or conditions to be tested. The methods of the invention include the following steps: (a) contacting a sample having cells to be assayed with the toxin or fragment thereof, as described herein, and a lipid or polymeric carrier (e.g., a DNA uptake facilitating agent) under conditions suitable for toxin protease activity, wherein the toxin substrate that contains a donor fluorophore, an acceptor having an absorbance spectrum overlapping the emission spectrum of the donor fluorophore, and a toxin recognition sequence containing a cleavage site, wherein the cleavage site intervenes between the donor fluorophore and the acceptor and wherein, under the appropriate conditions, resonance energy transfer is exhibited between the donor fluorophore and the acceptor; (b) exciting the donor fluorophore; and (c) determining resonance energy transfer of the treated substrate relative to a control substrate, where a difference in resonance energy transfer of the treated substrate as compared to the control substrate is indicative of protease activity. An additional step in an embodiment of the present invention is to subject the sample to a drug, compound or molecule to be tested. The compound to be assayed can be at concentrations as desired by the user carrying out the assay. In an embodiment, the concentration of compound to be assayed is serial diluted. A method of the invention can be practiced with an acceptor which is a fluorophore, or with a non-fluorescent acceptor.

In a method of the invention, resonance energy transfer can be determined by a variety of means. In one embodiment, the step of determining resonance energy transfer includes detecting donor fluorescence intensity of the treated substrate, wherein increased donor fluorescence intensity of the treated substrate as compared to the control substrate is indicative of toxin protease activity. In another embodiment, the step of determining resonance energy transfer includes detecting acceptor fluorescence intensity of the treated substrate, wherein decreased acceptor fluorescence intensity of the treated substrate as compared to the control substrate is indicative of toxin protease activity. In a further embodiment, the step of determining resonance energy transfer includes detecting the acceptor emission maximum and the donor fluorophore emission maximum, wherein a shift in emission maxima from near an acceptor emission maximum to near a donor fluorophore emission maximum is indicative of toxin protease activity. In an additional embodiment, the step of determining resonance energy transfer includes detecting the ratio of fluorescence amplitudes near an acceptor emission maximum to fluorescence amplitudes near a donor fluorophore emission maximum, wherein a decreased ratio in the treated sample as compared to the control sample is indicative of toxin protease activity. In yet a further embodiment, the step of determining resonance energy transfer is practiced by detecting the excited state lifetime of the donor fluorophore in the treated substrate, wherein an increased donor fluorophore excited state lifetime in the treated substrate as compared to the control substrate is indicative of toxin protease activity.

As discussed further below, a variety of conditions suitable for toxin protease activity are useful in a method of the invention. For example, conditions suitable for toxin protease activity can be provided such that at least 10% of the substrate is cleaved. Similarly, conditions suitable for toxin protease activity can be provided such that at least 20%, 30%, 40%, 50%, 60%, 70%, 80%, 90% or 95% of the toxin substrate is cleaved, or such that 100% of the toxin substrate is cleaved. In one embodiment, the conditions suitable for toxin protease activity are selected such that the assay is linear.

As used herein, the term "sample" means any biological matter that contains the toxin or toxin fragment, as described herein. In an embodiment, the toxin includes light chain or proteolytically active fragment thereof. Thus, the term sample encompasses but is not limited to purified or partially purified toxins; recombinant single chain or dichain toxin with a naturally or non-naturally occurring sequence; chimeric toxin containing structural elements from multiple toxin species or subtypes; recombinant toxin light chain with a naturally occurring or non-naturally occurring sequence; bulk toxin; formulated product; cells or crude, fractionated or partially purified cell lysates, for example, engineered to include a recombinant nucleic acid encoding a toxin or light chain thereof, including bacterial, baculoviral and yeast lysates.

In the methods of the invention, a sample is treated with a toxin under conditions suitable for toxin protease activity. Exemplary conditions suitable for toxin protease activity are well known in the art, and further can be determined by routine methods. See, for example, Hallis et al., J. Clin. Microbiol. 34:1934-1938 (1996); Ekong et al., Microbiol. 143:3337-3347 (1997); Shone et al., WO 95/33850; Schmidt and Bostian, supra, 1995; Schmidt and Bostian, supra, 1997; Schmidt et al., supra, 1998; and Schmidt and Bostian, U.S. Pat. No. 5,965,699. It is understood that conditions suitable for toxin protease activity can depend, in part, on the specific toxin type or subtype being assayed and the purity of the toxin preparation. Conditions suitable for toxin protease activity generally include a buffer, such as HEPES, Tris or sodium phosphate, typically in the range of pH 5.5 to 9.5, for example, in the range of pH 6.0 to 9.0, pH 6.5 to 8.5 or pH 7.0 to 8.0. Conditions suitable for toxin protease activity also can include, if desired, dithiothreitol or mercaptoethanol or another reducing agent, for example, where a dichain toxin is being assayed (Ekong et al., supra, 1997). In one embodiment, the conditions include DTT in the range of 0.01 mM to 50 mM; in other embodiments, the conditions include DTT in the range of 0.1 mM to 20 mM, 1 to 20 mM, or 5 to 10 mM. If desired, the toxin or fragment or sample can be pre-incubated with a reducing agent, for example, with 10 mM dithiothreitol (DTT) for about 30 minutes prior to addition of toxin substrate. Toxins are zinc metalloproteases, and a source of zinc, such as zinc chloride or zinc acetate, typically in the range of about 1 to 500 µM, for example, about 5 to 10 µM can be included, if desired, as part of the conditions suitable for toxin protease activity. Zinc chelators such as EDTA generally are excluded from a buffer for assaying toxin protease activity.

Conditions suitable for toxin protease activity also can include, if desired, bovine serum albumin (BSA). When included, BSA typically is provided in the range of 0.1 mg/ml to 10 mg/ml. In one embodiment, BSA is included at a concentration of 1 mg/ml. See, for example, Schmidt and Bostian, supra, 1997.

The amount of toxin or fragment thereof can be varied in a method of the invention. Peptide substrate concentrations useful in a method of the invention include concentrations, for example, in the range of 5 µM to 3.0 mM. A peptide substrate can be supplied at a concentration, for example, of 5 µM to 500 µM, 5 µM to 50 µM, 50 µM to 3.0 mM, 0.5 mM to 3.0 mM, 0.5 mM to 2.0 mM, or 0.5 mM to 1.0 mM. The skilled artisan understands that the concentration of toxin substrate or the amount of sample can be limited, if desired, such that the assay is linear. At increasingly high concentrations of substrate or toxin, linearity of the assay is lost due to the "inner filter effect," which involves intermolecular energy transfer. Thus, in one embodiment, a method of the invention relies on a toxin substrate concentration which is limited such that intermolecular quenching does not occur. In another embodiment, a method of the invention relies on a toxin substrate concentration of less than 100 µM. In further embodiments, a method of the invention relies on a toxin substrate concentration of less than 50 µM or less than 25 µM. If desired, a linear assay also can be performed by mixing toxin substrate with corresponding, "unlabeled" substrate which lacks the donor fluorophore and acceptor of the toxin substrate. The appropriate dilution can be determined, for example, by preparing serial dilutions of toxin substrate in the corresponding unlabeled substrate.

The concentration of purified or partially purified toxin or fragment thereof assayed in a method of the invention generally is in the range of about 0.0001 to 5000 ng/ml toxin, for example, about 0.001 to 5000 ng/ml, 0.01 to 5000 ng/ml, 0.1 to 5000 ng/ml, 1 to 5000 ng/ml, or 10 to 5000 ng/ml toxin, which can be, for example, purified recombinant light chain or dichain toxin or formulated toxin product containing human serum albumin and excipients. Generally, the amount of purified toxin used in a method of the invention is in the range of 0.1 pg to 10 µg. Purified, partially purified or crude samples can be diluted to within a convenient range for assaying for toxin protease activity against a standard curve. Similarly, a sample can be diluted, if desired, such that the assay for toxin protease activity is linear.

Conditions suitable for toxin protease activity also generally include, for example, temperatures in the range of about 20° C. to about 45° C., for example, in the range of 25° C. to 40° C., or the range of 35° C. to 39° C. Assay volumes often are in the range of about 5 to about 200 µl, for example, in the range of about 10 µl to 100 µl or about 0.5 µl to 100 µl, although nanoliter reaction volumes also can be used with the methods of the invention. Assay volumes also can be, for example, in the range of 100 µl to 2.0 ml or in the range of 0.5 ml to 1.0 ml.

Assay times can be varied as appropriate by the skilled artisan and generally depend, in part, on the concentration, purity and activity of the toxin. In particular embodiments, at least 10%, 20%, 30%, 40%, 50%, 60%, 70%, 80%, 90%, 95% or 100% of the toxin substrate is cleaved. In further embodiments, the protease reaction is stopped before more than 5%, 10%, 15%, 20%, 25% or 50% of the toxin substrate is cleaved. Protease reactions can be terminated, for example, by addition of $H_2SO_4$ as, addition of about 0.5 to 1.0 sodium borate, pH 9.0 to 9.5, or addition of zinc chelators. One skilled in the art understands that protease reactions can be terminated prior to exciting the donor fluorophore or determining energy transfer.

Proteolysis of the toxin substrate, and hence toxin protease activity, can be detected by a variety of means, for example, by detecting an increased donor fluorescence intensity; a decreased acceptor fluorescence intensity; a shift in emission maxima from near the acceptor emission maximum to near the donor fluorophore emission maximum; a decreased ratio of fluorescence amplitudes near the acceptor emission maximum to the fluorescence amplitudes near the donor fluorophore emission maximum; or an increased donor fluorophore excited state lifetime. The relevant fluorescence intensities or excited state lifetimes are detected at the appropriate selected wavelength or range of wavelengths. For example, where donor fluorescence intensity is detected, the appropriate selected wavelength at or near the emission maxima of the donor fluorophore, or a range of wavelengths encompassing or near to the emission maxima of the donor fluorophore. See 20080038756 for a discussion of carrying out FRET assays for certain toxins.

Endosomal Release:

An insulin release assay can be performed to determine the extent intoxication. In response to glucose stimulation, an insulinoma cell line, e.g., HIT-T15 secretes insulin in an exocytic process that depends on the activity of SNAP-25 for vesicle docking and fusion. If insulinoma cells lack a toxin receptor, these cells would be unable to uptake toxin upon exposure to this toxin and insulin secretion could occur in the presence of high glucose in the media. However, if insulinoma cells contain a toxin receptor, insulin secretion would be inhibited after toxin treatment since the toxin could intoxicate the cell and cleave SNAP-25.

To conduct an inhibition assay for insulin release, a suitable density of cells such as HIT-T15 cells is plated and grown according to conditions known in the art for growing and maintaining cell lines. The toxin or fragment along with a polymeric or lipid carrier, as described herein, is then contacted with the cells under conditions suitable for intoxication of the cells with the toxin or fragment. The cells are subjected to glucose, in varying concentrations (e.g., ranging from 4.0 mM glucose (low) to about 30 mM glucose (high)). Incubating the cells at an appropriate temperature (e.g., about 37° C.) allows insulin secretion to occur in cells into which the toxin or fragment has entered and wherein binding of the substrate to a receptor occurs. Alternatively intoxication can be monitored by blockage of vesicle mediated secretion after depolization with 5 mM potassium solution. In the case in which a compound, drug, molecule or condition prevents such binding (e.g., an antagonist), insulin secretion is also inhibited. In the case in which the compound, drug, molecule or condition allows or is an agonist of such binding, insulin secretion occurs or is increased. The amount of insulin present in the condition media samples was determined can be determined using an insulin ELISA assay (Peninsula Laboratories, Inc., San Carlos, Calif.). With this particular assay, e.g., exocytosis is expressed as the amount of insulin secreted per $1.5 \times 10^5$ cell/hr. Any method known in the art for detecting insulin or glucose can be used. Another approach to using HIT-T15 cells is to transfect the cells with a secreted peptide reporter such as luciferase fused to proinsulin or human growth hormone and assaying for release of the peptide transmitter after depolarization with potassium or stimulation with high glucose containing media.

Systems and Kits

The present invention further relates to systems and kits. The system or kit includes, e.g., one or more cell lines, one or more lipid or polymeric carriers (e.g., a DNA uptake facilitating agent), and/or one or more toxins or fragments thereof, as defined herein. The cell line, in embodiments, can already be intoxicated with the toxin or fragment and is therefore ready for cell based assays, e.g., to be evaluated by a drug candidate.

Polypeptides, Nucleic Acid Sequences, Vectors, Host Cells of the Present Invention As used herein, the term "recombinant" refers to a molecule that is one that is genetically made using techniques described herein.

As used herein, the term "polypeptide" encompasses amino acid chains of the toxin having any length, partial or full length proteins, wherein the amino acid residues are linked by covalent peptide bonds. Thus, a polypeptide can comprise a portion of the toxin or domain thereof, such as heavy chains, light chains and combinations thereof.

The polypeptides of the present invention referred to herein as "isolated" are polypeptides that are separated away from other proteins and cellular material of their source of origin. The compositions and methods of the present invention also encompass variants of polypeptides and DNA molecules of the present invention. A polypeptide "variant," as used herein, is a polypeptide that differs from the recited polypeptide only in conservative substitutions and/or modifications, such that the ability of the toxin is retained.

The present invention also encompasses proteins and polypeptides, variants thereof, or those having amino acid sequences analogous to the amino acid sequences of binding agents described herein. Such polypeptides are defined herein as analogs (e.g., homologues), or mutants or derivatives. "Analogous" or "homologous" amino acid sequences refer to amino acid sequences with sufficient identity of any one of the amino acid sequences of the present invention so as to possess the biological activity (e.g., the ability to bind to the toxin). For example, an analog polypeptide can be produced with "silent" changes in the amino acid sequence wherein one, or more, amino acid residues differ from the amino acid residues of any one of the sequence, yet still possesses the function or biological activity of the polypeptide. In particular, the present invention relates to homologous polypeptide molecules having at least about 40% (e.g., 45%, 50%, 55%, 60%, 65%, 70%, 75%, 80%, 85%, 90% or 95%) identity or similarity with SEQ ID NO: 2, 4, 6, 8, 10, 12, 14, 16, 18, 20, and 22 or combination thereof. Percent "identity" refers to the amount of identical nucleotides or amino acids between two nucleotides or amino acid sequences, respectfully. As used herein, "percent similarity" refers to the amount of similar or conservative amino acids between two amino acid sequences.

Homologous polypeptides can be determined using methods known to those of skill in the art. Initial homology searches can be performed at NCBI against the GenBank, EMBL and SwissProt databases using, for example, the BLAST network service. Altschuler, S. F., et al., J. Mol. Biol., 215:403 (1990), Altschuler, S. F., Nucleic Acids Res., 25:3389-3402 (1998). Computer analysis of nucleotide sequences can be performed using the MOTIFS and the Find- Patterns subroutines of the Genetics Computing Group (GCG, version 8.0) software. Protein and/or nucleotide comparisons were performed according to Higgins and Sharp (Higgins, D. G. and Sharp, P. M., Gene, 73:237-244 (1988) e.g., using default parameters).

The present invention, in one embodiment, includes an isolated nucleic acid molecule having a sequence of SEQ ID NO: 1, 3, 5, 7, 9, 11, 13, 15, 17, 19, and 21 or combinations thereof. As used herein, the terms "DNA molecule" or "nucleic acid molecule" include both sense and anti-sense strands, cDNA, genomic DNA, recombinant DNA, RNA, and wholly or partially synthesized nucleic acid molecules. A nucleotide "variant" is a sequence that differs from the recited nucleotide sequence in having one or more nucleotide deletions, truncations, substitutions or additions. Such modifications can be readily introduced using standard mutagenesis techniques, such as oligonucleotide-directed site-specific mutagenesis as taught, for example, by Adelman et al. (DNA 2:183, 1983). Nucleotide variants can be naturally occurring allelic variants, or non-naturally occurring variants. Variant nucleotide sequences preferably exhibit at least about 70%, more preferably at least about 80% and most preferably at least about 90% homology to the recited sequence. Such variant nucleotide sequences will generally hybridize to the recited nucleotide sequence under stringent conditions. In one embodiment, "stringent conditions" refers to prewashing in a solution of 6×SSC, 0.2% SDS; hybridizing at 65° Celsius, 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The present invention also encompasses isolated nucleic acid sequences that encode the polypeptide and in particular, those which encode a polypeptide molecule having an amino acid sequence of SEQ ID NO: 2, 4, 6, 8, 10, 12, 14, 16, 18, 20, and 22 or combinations thereof.

As used herein, an "isolated" nucleotide sequence is a sequence that is not flanked by nucleotide sequences which normally (e.g., in nature) flank the gene or nucleotide sequence (e.g., as in genomic sequences) and/or has been completely or partially purified from other transcribed sequences (e.g., as in a cDNA or RNA library). Thus, an isolated gene or nucleotide sequence can include a gene or nucleotide sequence which is synthesized chemically or by recombinant means. Nucleic acid constructs contained in a vector are included in the definition of "isolated" as used herein. Also, isolated nucleotide sequences include recombinant nucleic acid molecules and heterologous host cells, as well as partially or substantially or purified nucleic acid molecules in solution. The nucleic acid sequences that encode the toxin of the present invention include homologous nucleic acid sequences. "Analogous" or "homologous" nucleic acid sequences refer to nucleic acid sequences with sufficient identity of any one of the nucleic acid sequences described herein, such that once encoded into polypeptides, they possess the biological activity of any one of the toxins herein. In particular, the present invention is directed to nucleic acid molecules having at least about 40% (e.g., 45%, 50%, 55%, 60%, 65%, 70%, 75%, 80%, 85%, 90% or 95%) identity with SEQ ID NO: 1, 3, 5, 7, 9, 11, 13, 15, 17, 19, and 21 or combinations thereof.

Also encompassed by the present invention are nucleic acid sequences, DNA or RNA, which are substantially complementary to the DNA sequences encoding the polypeptides of the present invention, and which specifically hybridize with their DNA sequences under conditions of stringency known to those of skill in the art. As defined herein, substantially complementary means that the nucleic acid need not reflect the exact sequence of the sequences, but must be sufficiently similar in sequence to permit hybridization with nucleic acid sequence under high stringency conditions. For example, non-complementary bases can be interspersed in a nucleotide sequence, or the sequences can be longer or shorter than the nucleic acid sequence, provided that the sequence has a sufficient number of bases complementary to the sequence to allow hybridization therewith. Conditions for stringency are described in e.g., Ausubel, F. M., et al., Current Protocols in Molecular Biology, (Current Protocol, 1994), and Brown, et al., Nature, 366:575 (1993); and further defined in conjunction with certain assays.

Stringency Conditions for Nucleic Acids:

Specific hybridization can be detected under high stringency conditions. "Stringency conditions" for hybridization is a term of art which refers to the conditions of temperature and buffer concentration which permit and maintain hybridization of a particular nucleic acid to a second nucleic acid; the first nucleic acid may be perfectly complementary to the second, or the first and second may share some degree of complementarity which is less than perfect. For example, certain high stringency conditions can be used which distinguish perfectly complementary nucleic acids from those of less complementarity. "High stringency conditions" for nucleic acid hybridizations and subsequent washes are explained, e.g., on pages 2.10.1-2.10.16 and pages 6.3.1-6 in Current Protocols in Molecular Biology (Ausubel, et al., In: Current Protocols in Molecular Biology, John Wiley & Sons, (1998)). The exact conditions which determine the stringency of hybridization depend not only on ionic strength, temperature and the concentration of destabilizing agents such as formamide, but also on factors such as the length of the nucleic acid sequence, base composition, percent mismatch between hybridizing sequences and the frequency of occurrence of subsets of that sequence within other non-identical sequences. Thus, high stringency conditions can be determined empirically.

By varying hybridization conditions from a level of stringency at which no hybridization occurs to a level at which hybridization is first observed, conditions which will allow a given sequence to hybridize (e.g., selectively) with the most similar sequences in the sample can be determined. Exemplary conditions are described in the art (Krause, M. H., et al., 1991, Methods Enzymol. 200:546-556). Also, low and moderate stringency conditions for washes are described (Ausubel, et al., In: Current Protocols in Molecular Biology, John Wiley & Sons, (1998)). Washing is the step in which conditions are usually set so as to determine a minimum level of complementarity of the hybrids. Generally, starting from the lowest temperature at which only homologous hybridization occurs, each ° C. by which the final wash temperature is reduced (holding SSC concentration constant) allows an increase by 1% in the maximum extent of mismatching among the sequences that hybridize. Generally, doubling the concentration of SSC results in an increase in Tm of about 17° C. Using these guidelines, the washing temperature can be determined empirically for high stringency, depending on the level of the mismatch sought. In some embodiments, high stringency conditions include those in which nucleic acid with less than a few mismatches does not bind. High stringency conditions, using these guidelines, lie in a temperature range between about 40° C. and about 60° C., an SSC concentration range between about 1× and about 10× (e.g., about 2×), and a reaction time range of between about 30 seconds and about 36 hours.

EXEMPLIFICATION

Example 1

Summary

The present invention improves the utility of cell-based toxin assays through the use of a novel toxin delivery system that easily and dramatically increases the functional entry of *botulinum* neurotoxin (BoNT), and probably other related toxins, into cells. It was discovered that the functional delivery of *botulinum* neurotoxin (BoNT), serotype A, to cultured neuronal cells can be substantially improved by combining it with DNA transfection reagents before application. Surprisingly, this toxin "transduction" approach is also successful for the delivery of BoNT to all non-neuronal cells tested, cells which normally are completely refractory to intoxication. Finally, intoxication efficiencies were achieved approaching those of holotoxin in these cell lines by transducing only the BoNT catalytic domain into the cells using the DNA transfection reagents, obviating the need to use holotoxin to intoxicate cultured cells and avoiding the consequent safety and regulatory issues. This methodology improves functional cell delivery of other toxins, particularly those that normally intoxicate cells using cell entry mechanisms similar to BoNT. This invention also facilitates the testing of the functional consequences of mutations in BoNT LC as mutated versions of the Light Chain (LC) because recombinant proteins can be delivered to cells at physiologically relevant levels. This invention thus permits a broad expansion of the available cell and toxin options for the development of cell-based intoxication assays and improves the ability to screen for therapeutic agents that prevent or reverse toxin pathologies.

Example 2

Methods

Materials and Methods.
Cell culture and reagents:

M17 (ATCC #CRL-2267) cells were maintained in DMEM (Gibco, USA) containing 10% fetal bovine serum (FBS) (Gibco, USA). MEME (Gibco, USA) plus 10% FBS media were used for culturing Neuro2a (ATCC #CCL-131) and HEK293 (ATCC #CRL-1573) cells. HIT-T15 (ATCC #CRL-1777) cells were cultured in F12K (Gibco, USA) containing 10% horse and 5% FBS. $6 \times 10^4$ cells were seeded onto each well of 24-well plate and maintained at 37° C. After 72 hrs, culture medium was replaced with fresh medium before experimental treatments. Primary cultures of cerebellar granule cells were prepared from 7 day-old Sprague-Dawley rats essentially by the methods of Farkas. Briefly, after aseptically removing cerebella from the skulls, tissue was freed from meninges and incubated in 0.05% trypsin solution for 10 min at RT. After a brief centrifugation, cells were triturated in DMEM/F12 containing 10% FBS and filtered through a sterile cell strainer mesh with 40 um pore size (B D Falcon, USA). Cell number was determined by trypan blue exclusion, and cells were seeded onto poly-L-lysine (PLL) 1 g/cm2 laminin (Sigma, USA) coated 6 well plate with DMEM containing 10% FBS, 25 mM KCl, 2 mM Glutamax, and 100 g/mL gentamicin (Gibco, USA). The cultures were maintained at 37° C. in a humidified atmosphere of 6% CO2. After 24 hr of culturing cytosine arabinoside (Sigma, USA) was added to a final concentration of 20 µM to prevent astrocytic proliferation. The neurons were cultured for 7-8 days before use. FuGene-HD (Roche, USA), Lipofectamine 2000 (Invitrogen, USA) and PEI average molecular weights 0.6, 1.8, 10, 70 kDa (Alfa Aesar, USA) and 25 kDa (Sigma, USA)of various average molecular weights (Sigma-Aldrich) were used for transfection and transduction as recommended by the manufacturer except where indicated. Bafilomycin A1 was obtained from Tocris Cookson Inc (USA). BoNT/A (isotype 1), BoNT/B and BoNT/E were obtained from Metabiologics.

Resources: Recombinant BoNT/B light chain protease (amino acids 1-441) was expressed in pET14b with hexahistidine tags at the amino and carboxyl termini. The protein was expressed within *E. coli* in soluble form and purified to near homogeneity by standard nickel affinity chromatography. The recombinant BoNT/E LC was expressed in *E. coli* as a N-terminal fusion protein with glutathione-S-transferase. The protein was purified by standard glutathione affinity methods and provided as a gift by Dr. Randall Kincaid (Veritas Labs, USA). Antibodies: rabbit anti-SNAP25 antibody (Sigma); goat anti-rabbit HRP antiserum (Sigma); rabbit anti-VAMP2 antibody (Millipore); rabbit anti-CFP (gift from Dr. Randall Kincaid, Veritas Labs). Reagents for Western blotting including Wash Solution and LumiGLO Chemiluminescent Substrate were purchased from (KPL, USA).

BoNT/A Holotoxin Intoxication and Transduction:

Neuronal cell lines M17, Neuro2a and non-neuronal cell lines HEK293, HIT-T15 were tested in transfection reagent facilitated intoxication. 50 µl of serum free medium was used to prepare toxin dilution or toxin transfection mixture for each well of a 24-well plate. 0.75 µg BoNT/A was added with or without transfection reagent with a ratio of 1:3 (toxin [µg]: transfection reagent [µl]) and incubated at room temperature for more than 15 min. Apply the transfection mixture onto each wells. 3 hrs and/ or 24 hrs after transfection, cells were washed twice with 1 ml DPBS and incubated with fresh medium. Cell extracts were prepared 48 h post transfection. Cells were washed once with 1 ml DPBS, trypsinized, and washed once with 1 ml DPBS. 50 µl of sample buffer plus beta-mercaptoethanol was added to lyse cells and protein samples were boiled for 10 min. Toxin transduction efficiency was measured indirectly by monitoring the endogenous SNAP25 cleavage.

For testing toxin delivery efficacy through commercially available transfection reagents, Neuro2a cells were exposed to a toxin-transfection reagent mixture for various durations. Briefly, 50 µl serum free medium was used for each well of 24-well plate. BoNT/A was added with FuGene-HD using 3 µl per µg of toxin except where indicated. A well treated with toxin alone without FuGene-HD was included as a control. Apply the mixture onto each well. 0.5, 1, 2, 3, 6 and 24 hrs after transfection, cells were lysed with sample buffer plus beta-mercaptoethanol immediately or washed twice with 1 ml DPBS and incubated with fresh medium. Cell extracts were prepared 48 hrs post transduction with the procedures noted above. Toxin transduction efficiency was checked indirectly by monitoring the endogenous SNAP25 cleavage.

For testing the effective range of concentrations for transfection reagent-mediated cell intoxication, BoNT/A concentrations ranging from 0.1 to 10 nM were used in Neuro2a cells. Similar transduction procedures were taken with some modifications. 7.5 ng, 75 ng and 0.75 µg BoNT/A was diluted to 50 µl serum free medium followed by addition of transfection reagent with a ratio of 1:3 (toxin [µg]: transfection reagent [µl]) and incubated in room temperature for more than 15 min. FuGene-HD left out of toxin dilution was designated as control. 3 hrs and 24 hrs after transfection, cells were washed twice with 1 ml DPBS and incubated with fresh medium. Cell extracts were prepared 48 h post transduction.

Toxin transduction efficiency is checked indirectly by monitoring the endogenous SNAP25 cleavage.

BoNT/A Lc Protease Transduction:

The neuronal cell lines M17, Neuro2a and the non-neuronal cell lines HEK293, HIT-T15 were tested in transfection reagent facilitated Lc transduction. 50 μl serum free medium was used for preparing Lc dilution or Lc transduction mixture for each well of 24-well plate. 0.75 μg Lc438 or Lc424 was added with or without transfection reagent with a ratio of 1:3 (Lc [μg]: transfection reagent [μl]) and incubated in room temperature for more than 15 min. Apply the transfection mixture onto each wells. 24 hrs after transfection, cell extracts were prepared with the procedures noted above. Toxin transfection efficiency was checked indirectly by monitoring the endogenous SNAP25 cleavage.

BoNT/E Intoxication and Transduction

BoNT/E holotoxin was activated before cell intoxication. 1 mg/ml BoNT/E was nicked by incubating for 30 min at 37° C. with 0.3 mg/ml trypsin (type XI, bovine pancreas) in 30 mM HEPES, pH 6.75. Trypsin was subsequently inhibited by addition of 0.5 mg/ml trypsin inhibitor (type I-S, soybean) and incubation for 15 min at 20° C.

Toxins were aliquoted and stored at −20° C.; each experiment utilized a new aliquot of toxin to ensure uniform activity. Neuronal cell lines M17 and Neuro2a cell lines were tested in transfection reagent facilitated intoxication with procedures noted in 2.3.

Cell Viability Assay

MTT assays were performed to measure cell viability. M17 and Neuro2a cells were seeded onto 96 well plate for 24 hrs and cells were treated with recombinant Lc with or without preincubation with transfection reagents for another 24 hrs. Cell viability was measured 24 hrs after transduction and experimental procedures were followed according to manufacture instructions. Record absorbance at 570 nM with Synergy™ HT Multi-Mode Microplate Reader, and data were analyzed with KC4 software. Experiments were performed in triplicate.

Bafilomycin Blockage of BoNT/A Nature Intoxication:

The neuronal cell lines M17, Neuro2a and non-neuronal cell lines HEK293, HIT-T15 were treated with 1 μM of Bafilomycin A1 or DMSO for 2 hrs and washed with 1 ml DPBS twice before transduction. 0.75 μg BoNT/A or Lc438 was transduced to cell lines with the same preparation noted above. Due to the toxin insensitivity of neuroblastoma cell lines, primary cells were incorporated in this experiment as control to show the bafilomycin drug effect on BoNT intoxication in the absence of commercial DNA transfection reagent. For primary cells, 37.5 ng BoNT/A was added with or without transfection reagent. 4 hrs and 24 hrs after transfection, cell extracts were prepared as above. The inhibitory effect of Bafilomycin onto toxin/ Lc was measured indirectly by monitoring the endogenous SNAP25 cleavage.

Bafilomycin Effect on DNA Transfection:

0.5 μg CFP plasmid was transfected to M17, Neuro2a and HIT-T15 cells pre-treated with bafilomycin A1 for 2 hrs. 3 hrs or 24 hrs after transfection, cells were washed twice with 1 ml DPBS and incubated with fresh medium. 24 hrs post transfection fluorescence signals were recorded before cell extracts were prepared with the same procedures noted above. The inhibitory effect of bafilomycin onto DNA transfection was measured by monitoring the cell fluorescence signals through Olympus IX50 microscope and the CFP protein expression through Western Blotting.

Western Blotting:

Cell extract prepared from $4\times10^5$ cells was boiled for 5 min and loaded to 15% pre-casted protein gels (BioRad). Protein samples were separated and transferred to PVDF membrane with cool temperature. To eliminate non-specific binding blots were incubated with 5% skim milk/PBST 0.5% for at least 1 hr at room temperature. Blots were incubated with primary antibodies: Rabbit anti SNAP25 (1:5000), Rabbit anti XFP (1:5000), Rabbit anti VAMP2 (1:5000) at 4° C. overnight. Blots were then washed with PBST 0.5% buffer and then treated with goat anti rabbit antibody (1:5000) with HRP label was subsequently incubated with blots for 1 hr at room temperature before signal detection using LumiGLO Chemiluminescent Substrate (KPL). Signals were scanned by Kodak [instruments] and analyzed with the Kodak 1D 3.6 network.

Example 3

Results

Commercial Lipid-Based DNA Transfection Reagents Enhance *botulinum* Intoxication of Cultured Neuronal Cells.

It was observed that neuronal cells intoxicated with BoNT/A immediately after DNA transfection using the FuGene-HD reagent (Roche) appeared more efficiently intoxicated than control cells so the effect of FuGene-HD on BoNT intoxication was directly tested. The measure of BoNT serotype A intoxication used in these studies was the percentage of the cellular SNAP25 that had been cleaved. As shown in FIG. 1, virtually no SNAP25 was cleaved following 3 hrs intoxication and about 50% was cleaved with 24 hrs exposure to BoNT/A in M17. When the toxin was pre-incubated with FuGene-HD prior to addition to media, approximately 50% of SNAP25 became cleaved with 3 hrs of toxin exposure and 90% was cleaved in M17 after a 24 hrs exposure. The effect of the FuGene-HD DNA transfection reagent on intoxication efficiency was even more profound in the Neuro2a neuroblastoma cell line (FIG. 1). Under normal intoxication conditions, no cleavage of SNAP25 was detected following a 3 hrs exposure to toxin and about 10% cleavage occurred with a 24 hr toxin exposure. When intoxication was performed following preincubation with FuGene-HD, about 80% and 95% of cellular SNAP25 was cleaved with 3 hr and 24 hr toxin transfection respectively. Enhancement of intoxication also occurred when the toxin and FuGene-HD were separately added to neuronal cells, but the effect was smaller (not shown). Thus, the presence of FuGene-HD accelerated the efficiency of intoxication following short exposure and increased the level of intoxication following a long exposure. In the case of Neuro2a, the presence of FuGene-HD converted a cell line from one that was poorly intoxicated by BoNT/A to one that is very efficiently intoxicated. The amount of enhanced intoxication did not change significantly using several fold more or less FuGene-HD and the ratio of 1:3 was selected for routine use to minimize toxicity to the cells. Nevertheless, to exclude the possibility that transfection reagents increased cell death leading to release of SNAP25 and enhanced cleavage, MTT assays were performed and revealed no significant change in cell viability following exposure to FuGene-HD at 1:3 (data not shown).

To characterize the rate at which DNA transfection reagent-enhanced intoxication occurs, Neuro2a cells were exposed to BoNT/A in the presence of FuGene-HD for variable times and harvested immediately. As shown in FIG. 2, cleavage of SNAP25 could be observed in as little as 30 minutes and maximum cleavage of about 90% occurred within the first 6 hrs. In this experiment, the Neuro2a cells were not detectably intoxicated in the absence of FuGene-HD. When the medium was changed and the cells were cultured for an additional 2 days after short toxin exposures (1-3 hrs) but not longer exposures (6 or 24 hrs), a small amount of additional SNAP25 cleavage occurred but never reached the 90% cleavage observed after only 6 hours exposure to toxin (data not shown). This suggests that the BoNT protease rapidly reaches the cell cytosol and most SNAP25 cleavage is complete within only a few hours of the toxin entering the cell. These results also suggest that the uncleaved SNAP25 observed in these experiments is from cells that have not become intoxicated.

Typically neuroblastoma cells require BoNT concentrations of 10 nM or more to detect significant intoxication while primary neurons are often sensitive to BoNT concentrations as low as 100 pM. Experiments were performed to examine the sensitivity of DNA transfection reagent enhanced intoxication of neuroblastoma cells to toxin concentrations. Neuro2a cells were cultured for 24 hrs with BoNT/A concentrations ranging from 0.1 to 10 nM (FIG. 3) and harvested 48 hrs after toxin exposure. In the absence of FuGene-HD, the Neuro2a cells were not detectably intoxicated even at 10 nM. In the presence of FuGene-HD, some cleavage of SNAP25 was observed in Neuro2a cells exposed to as little as 100 pM BoNT/A. In a similar experiment with only 3 hrs BoNT/A exposure, 10% and 80% of SNAP25 cleavage was detected with toxin concentrations of 1 nM and 10 nM respectively (data not shown). Interestingly, the efficiency of intoxication of primary neurons was not enhanced with DNA transfection reagents (see below), suggesting that these cells are being intoxicated with maximal sensitivity under normal conditions. These data show that it is possible to achieve intoxication efficiencies in at least some neuroblastoma cells that approach those of primary neurons by including FuGene-HD with the toxin.

Commercial DNA Transfection Reagents Permit BoNT/A Intoxication of Non-Neuronal Cells.

Figure 4:
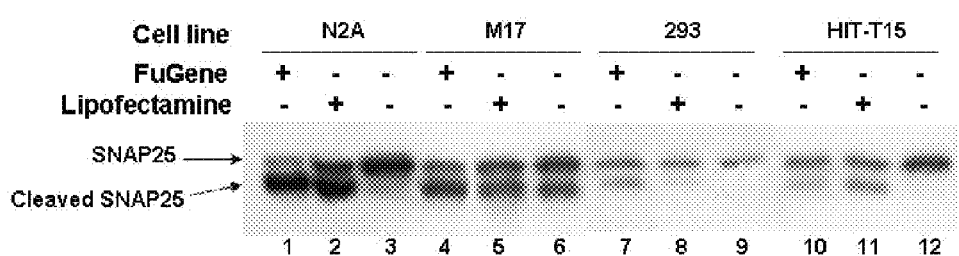
FIG. 4 is a photograph of a western blot showing DNA transfection reagent that facilitates BoNT/A internalization of non-neuronal cell lines. Neuronal cell lines Neuro2a (N2A), M17 and non-neuronal cell lines HEK293 (293), HIT-T15 were exposed to 10 nM BoNT/A for 24 hrs with (+) or without (−) pre-incubation with DNA transfection reagents, FuGene-HD or Lipofectamine 2000. Cell extracts were prepared and the extent of BoNT/A intoxication was measured by Western blotting to monitor SNAP25 cleavage.

Results from the previous section indicated that inclusion of commercial DNA transfection reagents during BoNT intoxication of cells substantially increased intoxication efficiency in two neuroblastoma cell lines. In normal intoxication, it has been shown that *botulinum* toxin is internalized through receptor-mediated endocytosis. BoNT/A uptake into cells normally requires the presence of both ganglioside and the SV2 protein receptors which leads to its specificity for neuronal cells. To determine whether the use of DNA transfection reagents might bypass the need for surface receptors, transfection reagent enhancement of intoxication was tested in two non-neuronal cell lines that express SNAP25 yet are not normally susceptible to BoNT/A intoxication. One cell line, HEK293, is an embryonic kidney line and the other cell line, HIT-T15 is a human insulinoma cell line. As expected, SNAP25 cleavage was not detected in HEK293 or HIT-T15 cells following incubation with 10 nM of BoNT/A (FIG. 4). In contrast, inclusion of FuGene-HD clearly facilitated the uptake of BoNT/A into these cells leading to significant SNAP25 cleavage.

A second DNA transfection reagent, Lipofectamine 2000 (Invitrogen), was compared to FuGene-HD for the ability to enhance BoNT/A intoxication of neuronal and non-neuronal cell lines (FIG. 4). In the case of the M17 and Neuro2a cells, both DNA transfection reagents significantly enhanced BoNT/A uptake into cells with FuGene-HD showing a slightly more pronounced effect. Interestingly, the Lipofectamine 2000 reagent proved to be the more effective reagent for enhancing BoNT uptake into HIT-T15 cells. The results demonstrate that both lipid-based commercial DNA transfection reagents facilitate the uptake of BoNT/A into both neuronal and non-neuronal cells and suggest that different transfection reagents are variably efficient in this ability when used during intoxication of different cell lines.

Commercial DNA Transfection Reagents Facilitate Transduction of the BoNT/A Light Chain Protease in the Absence of the BoNT/A Heavy Chain.

Figure 5:
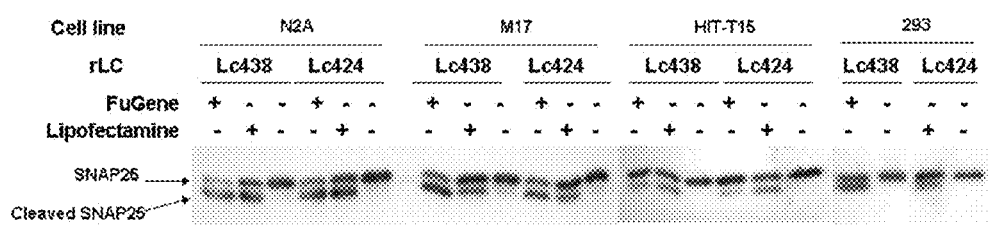
FIG. 5 is a photograph of a western blot of various DNA transfection reagents that promote cellular internalization of BoNT/A Lc protease in the absence of Hc. Neuronal cell lines Neuro2a (N2A), M17 and non-neuronal cell lines HIT-T15, HEK293 (293) were exposed for 24 hrs to 30 nM of recombinant BoNT/A LC protease, using either the full-length protease (Lc438) or the carboxyl-truncated form (Lc424). The protease was added to cell culture with (+) or without (−) pre-incubation with the DNA transfection reagents, FuGene-HD or Lipofectamine 2000. Cell extracts were prepared and the extent of BoNT/A intoxication was measured by Western blotting to monitor SNAP25 cleavage. Cell extracts were prepared and the extent of BoNT/A intoxication was measured by Western blotting to monitor SNAP25 cleavage.

It has been shown that the BoNT heavy chain (Hc) domain has been shown to play at least two critical roles during neuronal cell intoxication; binding to the neuronal cell receptors and chaperoning the translocation of the BoNT light chain (Lc) protease from the endosome to the cytosol Whether the BoNT Hc domain was necessary for BoNT uptake facilitated by commercial DNA transfection reagents was tested. For these experiments, two different forms of the BoNT/A Lc were employed. The Lc438 form contains the full size protease released following proteolytic cleavage from the Hc domain during natural processing by the *Clostridium botulinum* microbe. Lc424 is identical to Lc438 except that 16 amino acids are removed from the carboxyl end, a modification that does not significantly affect proteolytic activity but improves expression and solubility properties. The results shown in FIG. 5 show that the FuGene-HD and Lipofectamine 2000 DNA transfection reagents are efficiently able to promote the transduction of recombinant BoNT/A Lc into both neuronal and non-neuronal cells. Surprisingly, a very low concentration of BoNT/A Lc was sufficient to promote internalization and cleavage of cytosolic SNAP25, a concentration similar to that needed for intoxication by BoNT holotoxin. Both FuGene-HD and Lipofectamine 2000 were effective in all four cell types tested, although as with BoNT holotoxin, FuGene-HD was more effective for Neuro2a, M17 and HEK293 while Lipofectamine 2000 was more effective with HIT-T15 cells (FIG. 4). As expected, no SNAP25 cleavage occurred in cells when the Lc was added to the medium in the absence of DNA transfection reagents.

Polyethyleneimine Polymers Facilitate Transduction of BoNT/A Holotoxin and Recombinant BoNT/A Lc Protease.

The chemical nature of the commercial DNA transfection reagents, FuGene-HD and Lipofectamine 2000, is proprietary although both are described as lipid-based and Lipofectamine 2000 as a cationic lipid reagent (InVitrogGen). BoNT/A toxin transduction efficacy was tested using various polymer lengths of cationic polyethyleneimine as a DNA transfection reagent with defined chemical structure. The data shown in FIG. 6 demonstrate that PEI polymers also have the ability to promote BoNT holotoxin and Lc transduction into different cell types. The efficiency of transduction varied widely with the use of different size PEI polymers.

Lipid-Based Transduction of BoNT/A Lc Protease is Sensitive to Inhibitors of ER Acidification.

During normal neuronal cell intoxication, BoNT is internalized by receptor mediated endocytosis after which it becomes trapped inside an endosome. Following acidification of the endosome, the BoNT Lc protease undergoes a conformational change and is translocated to the cytosol through a channel created by the BoNT Hc domain. Bafilomycin is an inhibitor of vacuolar adenosine triphosphatase and prevents endosome acidification. Previous studies have shown that nerve cell intoxication by BoNT is inhibited by bafilomycin. To explore the role of endosome acidification in the DNA transfection reagent transduction of BoNT/A Lc, transduction was performed in the presence or absence of bafilomycin. In these experiments, cells were pre-treated with 1 μM of bafilomycin A1 or DMSO for 2 hrs before transfection or intoxication. Cytosolic internalization of the Lc was assessed by monitoring cleavage of SNAP25 within cells. Lc internalization was tested, in most cases, following either 4 or 24 hrs incubation with BoNT/A holotoxin or purified Lc, plus or minus bafilomycin.

Figure 6:
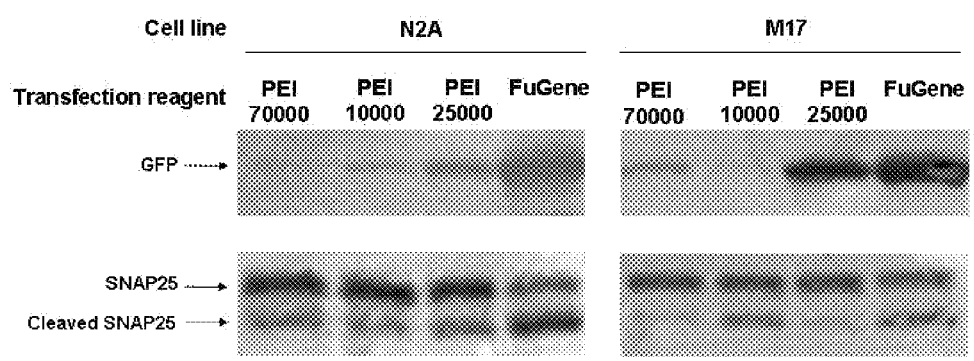
FIG. 6 is a photograph of a western blot of defined cationic lipid polymer reagents that promote BoNT intoxication. Neuronal cell lines Neuro2a and M17 were incubated for 24 hrs with 30 nM recombinant BoNT/A LC (Lc438) and a GFP expression plasmid with (+) or without (−) pre-incubation with FuGene-HD (FuGene) or PEI having average molecular weights of 10000, 25000 or 70000. Cell extracts were prepared and the extent of BoNT/A intoxication was measured by Western blotting to monitor SNAP25 cleavage. The efficiency of DNA transfection was assayed by Western blotting.

As a positive control for these experiments, pretreatment with bafilomycin was shown to completely inhibit 4 hr BoNT/A intoxication of primary rat granule cerebellar neurons (RGCN) whether DNA transfection reagents were included or not (FIG. 6). With 24 hr BoNT/A intoxication, a small amount of SNAP25 cleavage was observed in primary cells treated with bafilomycin. Some cytotoxicity due to bafilomycin treatment was visually apparent and so some SNAP25 cleavage may occur as BoNT/A in the media gains access to SNAP25 released following cell lysis. Alternatively, the effect of bafilomycin may be lost during the longer intoxication period to permit entry of some Lc protease into the cell cytosol. When bafilomycin was omitted, BoNT/A treatment led to nearly complete cleavage of SNAP25. DNA transfection reagents did not promote improved BoNT/A or BoNT/A Lc intoxication of primary neurons (FIG. 7). These neurons were also not susceptible to plasmid DNA transfection with these same reagents (data not shown).

Bafilomycin inhibited SNAP25 cleavage following 4 hrs or 24 hrs incubation of both M17 and Neuro2a neuroblastoma cells with BoNT/A holotoxin, whether intoxication was enhanced by DNA transfection reagents or not (FIG. 7). This suggests that the enhanced intoxication obtained with these reagents occurs through the natural intoxication pathway including translocation of Lc from the endosome to the cytosol. More surprising, bafilomycin also inhibited functional internalization of recombinant BoNT/A Lc into both neuroblastoma and non-neuronal cells in the absence of Hc, most obviously in Neuro2a and HIT-T15 cells (FIG. 7). As with RGCN above, these experiments are complicated by the bafilomycin cytotoxicity, which leads to increased background of SNAP25 cleavage following addition of BoNT/A Lc. This is most apparent in 293 cells which appear particularly susceptible to bafilomycin toxicity. Despite this background though, it is clear that bafilomycin blocks the enhanced cleavage of SNAP25 elicited by incubation of cells with BoNT/A Lc in the presence of DNA transfection reagents. Bafilomycin had no inhibitory effect on the efficiency of plasmid DNA transfection mediated by FuGene in Neuro2a, M17 or HIT-T15 cells as assessed by fluorescent protein expression from a transfected expression vector (data not shown). These results suggest that the DNA transfection reagent-mediated transduction of BoNT/A Lc requires endosome acidification, and thus occurs via a similar mechanism as occurs during holotoxin intoxication.

Commercial DNA Transfection Reagents Enhance Cellular Uptake of other BoNT Serotypes.

Figure 8:
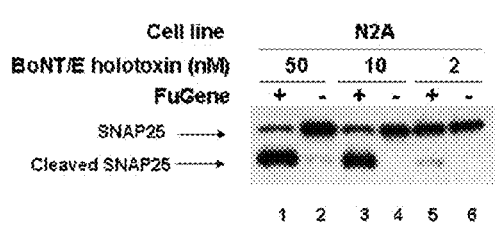
FIG. 8 is a photograph of a western blot showing that DNA transfection reagent enhances multiple toxin/Lc serotypes internalization in two neuroblastoma cell lines. M17 or Neuro2a cells were exposed to 50, 10 or 2 nM of BoNT/E toxin (A) or 30 or 6 nM of GST-Lc/E (B) or 50 or 10 nM of BoNT/B toxin (C) or 150 or 30 nM of recombinant Lc/B (D) +or − the FuGene-HD transfection reagent for 24 h. Cell extracts were prepared and revolved by SDS-PAGE. Toxin or Lc internalization was measured by detecting the 24KDa SNAP25 (type E) or the reduction of VAMP2 (type B) by Western blotting.
Figure 8:
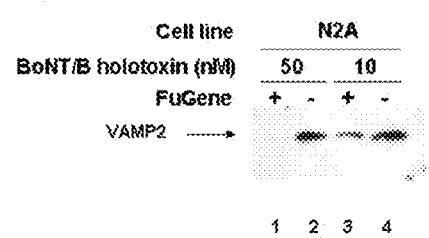
Figure 8:
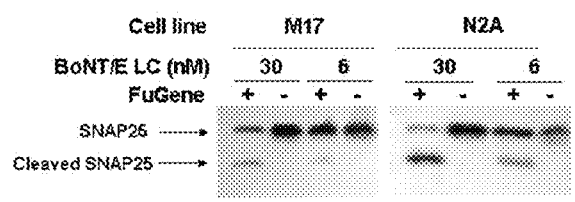
Figure 8:
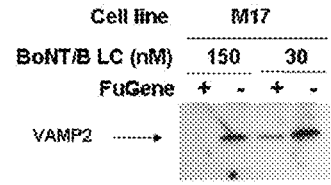

Previous experiments showed that commercial DNA transfection reagents facilitate BoNT toxin or Lc internalization into a variety of neuronal and non-neuronal cell lines. To test whether DNA transfection reagent-mediated intoxication might be unique to type A toxin, *botulinum* toxin type B and type E were also tested using this delivery system. Cleavage of SNAP25 was used as the indicator for BoNT/E toxin or Lc internalization while reduction of VAMP2 was used to monitor BoNT/B toxin or Lc internalization. As shown in FIG. 8, only trace amounts of the substrate proteins normally became cleaved following exposure of M17 or Neuro2a neuroblastoma cells to even high concentrations of the BoNT holotoxins or Lc protease. In contrast, inclusion of FuGene-HD promoted substantial cleavage of the appropriate BoNT substrates for both BoNT/B and BoNT/E. Similar results were obtained when the holotoxins were replaced by purified recombinant Lc proteases of both toxin serotypes. These results show that enhanced internalization of BoNT Lc proteases by DNA transfection reagents occurs for serotypes that naturally use different surface receptors to enter cells and may function for all serotypes.

Example 4

Discussion

Although BoNT intoxication is exquisitely efficient within animals and cultured primary neurons, it has not proved so efficient in established cell lines and this has inhibited research activities and cell-based drug screening efforts. Intoxication occurs following receptor-mediated internalization of BoNT and then transposition of the toxin light chain (Lc) protease from the endosome to the cytosol. The uptake and then chaperoning of the protease to the cytosol is mediated by the BoNT heavy chain (Hc). Because BoNT Hc binds to receptors found specifically on neuronal cells, non-neuronal cells have proven to be insensitive to the toxin. A variety of neuroblastoma cell lines are available and, while detectable BoNT intoxication will often take place (usually measured by SNARE protein cleavage), it is generally far less efficient than in primary neurons. Here it was shown that inclusion of commercial DNA transfection reagents during BoNT intoxication can significantly improve intoxication efficiencies and make possible efficient BoNT protease internalization into non-neuronal cells even in the absence of the BoNT heavy chain.

While it has been possible to experimentally deliver BoNT Lc to cell cytosol by DNA transfection methods or cell permeabilization, these methods result in cells that are often damaged with high and likely uneven levels of Lc protein that arrives in the cytosol by processes different than occur during intoxication. The reagents used here to deliver BoNT to cells are not considered particularly toxic to cells. These reagents are widely used for DNA transfection reagents and are either lipid-based (Lipofectamine 2000), polycationic polymers (PEI) or of undefined chemistry (FuGene). Lipid-mediated DNA transfection is reported to occur via endocytosis and release from endosomes and thus follows similar route into as *botulinum* toxin entry into neurons. While lipid-based reagents have been used to deliver proteins to cells in a process called transduction, the reagents used in this study are not generally used for this purpose. Some studies have identified other lipid-based reagents that are effective for protein transduction although they have not been studied for delivery of BoNT proteases and were not tested here. An early report of intoxication after liposomal delivery of BoNT Lc to motor neurons in animals was not apparently followed up in cultured cells.

BoNT holotoxin intoxication of at least some neuroblastoma cells can be substantially improved by the presence of certain DNA transfection reagents such as FuGene-HD, Lipofectamine 2000 and polyethylenimine (PEI). Furthermore, these reagents permit intoxication of some non-neuronal cell types that are not normally susceptible to BoNT intoxication. Finally, the DNA transfection reagents facilitate intoxication of neuronal and non-neuronal cells exposed only to isolated BoNT Lc proteases. Since the non-neuronal cells are thought to lack the protein receptors recognized by BoNT, and since the isolated BoNT Lcs lack the receptor binding domains, the results imply that the DNA transfection reagents are facilitating uptake of BoNT through a process independent of cell surface protein receptors. Lipid-based DNA transfection reagents, such as used in our studies, facilitate DNA endocytosis in a wide array of cell types in a process not shown to involve protein receptors. It is likely that these reagents perform a similar role in BoNT transduction. It is believed that the DNA transfection reagents facilitate the endocytosis of BoNT holotoxin or isolated BoNT Lc, even in the absence of BoNT cell surface receptors.

Primary neurons are the most sensitive cells to BoNT holotoxin intoxication, requiring as little as picomolar quantities of some serotypes to produce effects on the cells. Use of DNA transfection reagents did not improve the efficiency of BoNT/A intoxication of primary rat cerebellar granule neurons (not shown). Detectable DNA transfection in these cells were achieved with these reagents. It is not known whether the inability to improve intoxication efficiency was due to poor responsiveness to DNA transfection reagents in primary cerebellar neurons, or because receptor-mediated internalization is not limiting in these cells.

Typically neuroblastoma cells are sensitive to a more limited range of BoNT serotypes than primary neurons and require higher BoNT concentrations to achieve measurable intoxication. The neuroblastoma cells used in this study, Neuro2a and M17, required nanomolar amounts of BoNT serotypes A, B and E for detectable cleavage of their SNARE protein substrates. Neuro2a cells, which are the least sensitive of the two lines, were found to become several orders of magnitude more sensitive to these BoNT serotypes in the presence of DNA transfection reagents. The BoNT sensitivity of M17 cells was also improved substantially by these reagents. BoNT/A intoxication of a third neuroblastoma cell line, PC12, was only slightly improved by DNA transfection reagents (not shown). DNA transfection in this cell line with these reagents was also very poor and may explain the poor enhancement of intoxication. The results indicate that, for neuroblastoma cells susceptible to DNA transfection, it is possible to achieve BoNT intoxication with sensitivities close to those obtained in primary neurons.

To further characterize DNA transfection reagent enhanced intoxication, the time required to achieve intoxication in the presence or absence of these reagents in Neuro2a cells were compared. First it was shown that delivery of functional BoNT Lc to the cell cytosol was both time and dose dependent. Some SNARE protein cleavage could be detected as soon as 30 m following addition of 10 nM BoNT/A in the presence of FuGene-HD, while almost no cleavage could be detected after 24 hours in the absence of FuGene. In a separate study, Neuro2a cells were exposed to toxin for variable amounts of time with FuGene-HD, then washed and cultured an additional 24 hours before being tested for SNAP25 cleavage. These results showed that exposure to BoNT/A for more than 2 hours did not improve the level of SNAP25 cleavage detected a day later (data not shown). Extending the culture time beyond a day also did not improve the level of SNAP25 cleavage. These results suggest that virtually all of the Neuro2a cells that are susceptible to BoNT/A in FuGene-HD have endocytosed toxin by two hours and that the small amount of SNAP25 that remains intact in the population probably derives from a subset of cells that remain refractory and have not internalized BoNT/A.

Consistent with the hypothesis that the DNA transfection reagents facilitate receptor-independent uptake of BoNT, it was shown that these reagents make it possible to achieve BoNT intoxication of non-neuronal cells not normally susceptible to the toxin. The two cell lines studied, HEK293 and HIT-T15 are both commonly used cell lines for studies of protein secretion and both contain SNARE protein substrates for BoNT. In both cell lines, easily detected SNARE protein cleavage could be detected following incubation with 10 nM BoNT/A in the presence of FuGene-HD or Lipofectamine 2000. It is possible that the improved intoxication efficacy obtained with lipid-based DNA transfection reagents is aided by the enhanced SNARE protein cleavage activity that has been reported for some BoNT serotypes in the presence of charged lipid mixtures. This would require that the lipid components remain associated with the BoNT Lc following uptake and translocation and promote improved substrate cleavage in the cytosol. Whatever mechanisms are involved, the ability to achieve BoNT intoxication of various neuronal and non-neuronal secretory cell lines without the need to transfect or permeabilize the cells should have useful research applications.

It was tested whether enhanced BoNT holotoxin intoxication of cells required endosomal acidification as was previously shown to be necessary for natural intoxication. Bafilomycin inhibits endosome acidification and inhibits natural intoxication, presumably by altering the ability of the BoNT Hc to serve as a chaperone for transcytosis of BoNT Lc. In contrast, DNA transfection as mediated by lipid-based reagents does not require acidification for function transfection of cells. BoNT intoxication of both neuronal and non-neuronal cell lines, in the presence or absence of DNA transfection reagents, was clearly inhibited by bafilomycin. Thus, although the reagents appear to promote a receptor-independent endocytosis of BoNT, the subsequent step in the intoxication process, specifically translocation from the endosome to the cytosol, appears to take place by natural intoxication processes. This suggests that cells intoxicated by BoNT in the presence of DNA transfection reagents remain good models of naturally intoxicated cells.

Since the DNA transfection reagents obviate the need for cell surface receptors during BoNT intoxication, it is understandable that this could also obviate the need for the BoNT Hc receptor binding domain to achieve internalization of BoNT Lc. It is much more difficult to explain how the BoNT Lc is transferred to the cytosol following endocytosis in the absence of the Hc translocation domain, yet this clearly occurs. The results show that isolated BoNT Lc for serotypes A, B and E are each capable of efficient internalization to the cytosol and consequent SNARE protein cleavage when applied some neuronal and non-neuronal cells in the presence of DNA transfection reagents. The molar amount of BoNT Lc required to produce SNARE protein cleavage was similar to that required for holotoxin intoxication, indicating that the intoxication efficiency is not significantly reduced when BoNT Lc is delivered to cells with DNA transfection reagents in the absence of Hc. Surprisingly, this functional transduction of BoNT Lc was fully sensitive to bafilomycin indicating that endosome acidification is a critical component of the BoNT Lc transduction process. This result appears inconsistent with prior reports that BoNT Hc is required for Lc translocation from the endosome to the cytosol. It is believed that the DNA transfection reagents may remain associated with the BoNT Lc and provides the chaperone function normally performed by the Hc. Methods permitting BoNT Lc internalization through the endosome in the absence of Hc should permit experiments to further elucidate the pathways and mechanisms of BoNT Lc translocation and intracellular transport.

The ability to intoxicate cultured neuronal and non-neuronal cells by a process that mimics that of native BoNT without the need for holotoxin reduces risks to workers and simplifies the facility requirements. This could be particularly useful in the performance of high throughput screening for BoNT inhibitors using cell-based assays.

The teachings of U.S. patent application Ser. No. 12/481,889, filed Jun. 10, 2009, entitled "Designer Ubiquitin Ligases for Regulation of Intracellular Pathogenic Proteins" by Shoemaker, Charles, et al. are incorporated herein by reference in its entirety.

The teachings of PCT Application No., PCT/US10/21479, filed Jan. 20, 2010, entitled "Methods For The Delivery Of Toxins Or Enzymatically Active Portions Thereof" by George A. Oyler, et al. are incorporated herein by reference in its entirety.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of assessing in vitro an effect of a molecule or compound on a cell intoxicated with a toxin or an enzymatically active fragment thereof; the method comprises:
   a. contacting a *botulinum* neurotoxin or an enzymatically active fragment of the *botulinum* neurotoxin with a lipid or polymeric carrier to thereby obtain a mixture;
   b. exposing cells to the mixture in an amount to allow the *botulinum* neurotoxin or enzymatically active fragment thereof to enter the cell, to thereby obtain intoxicated cells;
   c. subjecting the intoxicated cells to the molecule or compound to be assessed; and
   d. assessing the effect of said molecule or compound on the intoxicated cell by assessing the percent cleavage of SNAP25, a level of one or more SNARE proteins, or a combination thereof.

2. The method of claim 1, wherein assessing the effect of the molecule or compound is assessing an amount of endoprotease activity or an amount of endosome release of the toxin.

3. The method of claim 2, wherein the molecule or compound being assessed is an antagonist or an agonist thereof.

4. The method of claim 2, wherein assessing the level of one or more SNARE proteins consists of assessing synaptobrevin 1, synaptobrevin 2, syntaxin, and a combination thereof.

5. The method of claim 2, wherein the cell is an insulinoma or neuroendocrine cell, the method further comprises:
   a. subjecting the intoxicated cell to glucose under conditions that allow for insulin secretion to occur; or subjecting the intoxicated cell to potassium solution mediated depolarization; and
   b. assessing release of the *botulinum* neurotoxin, the enzymatically active fragment thereof, or the cleavage of recombinant SNARE proteins by assessing a level of insulin secretion;
   wherein an increase of insulin secretion is indicative of an increased inhibition of the *botulinum* neurotoxin, the enzymatically active fragment thereof, or the cleavage of recombinant SNARE proteins; and a decrease of insulin secretion is indicative of a decreased inhibition thereof.

6. The method of claim 2, wherein the cell is an insulinoma or other neuroendocrine cell, the method further comprises:
   a. transfecting the cell with a plasmid encoding a neuropeptide reporter or vesicle fusion indicator;
   b. subjecting the mixture to glucose under conditions that allow for insulin secretion to occur; or subjecting the cell to potassium solution mediated depolarization;
   c. assessing protease activity of the *botulinum* neurotoxin, the enzymatically active fragment thereof, or the cleavage of recombinant SNARE proteins by assessing a level of insulin secretion; wherein an increase of insulin secretion is indicative of an increased inhibition of the *botulinum* neurotoxin, the enzymatically active fragment thereof, or the cleavage of recombinant SNARE proteins; and a decrease of insulin secretion is indicative of a decreased inhibition thereof.

7. The method of claim 1, further comprising:
   a. labeling a toxin substrate with a donor fluorophore and an accepter separated by a SNARE sequence containing the endoprotease cleavage site, wherein the toxin substrate is a recombinant SNARE protein, to thereby obtain a treated toxin substrate under the condition of the intoxicated cells subjecting to the molecule or compound,
   b. exciting said donor fluorophore; and
   c. determining resonance energy transfer in said treated toxin substrate to a control substrate with the absence of the molecule or compound, wherein a difference in resonance energy transfer in said treated toxin substrate as compared to said control substrate is indicative of toxin protease activity as the effect of the molecule or compound on the intoxicated cell.

8. The method of claim 1, wherein the lipid or polymeric carrier is one or more lipid or polymeric carrier type DNA transfection reagents.

9. The method of claim 8, wherein the DNA transfection reagent consist of: polylysine, polyethylenimine (PEI), a polymeric carrier, a cationic lipid reagent, polycationic polymers, and any combination thereof.

10. The method of claim 8, wherein the *botulinum* neurotoxin is contacted with the one or more lipid or polymeric carrier type DNA transfection reagents in an amount between about 0.1 pM and about 1 µM.

11. The method of claim 10, wherein the *botulinum* neurotoxin is contacted with the one or more lipid or polymeric carrier type DNA transfection reagents in an amount between about 1 nM and about 10 nM.

12. The method of claim 8, wherein the *botulinum* neurotoxin is contacted with the one or more lipid or polymeric carrier type DNA transfection reagents for a length of time between about 5 minutes and about 72 hours.

13. The method of claim 12, wherein the *botulinum* neurotoxin is contacted with the one or more lipid or polymeric carrier type DNA transfection reagents for a length of time between about 1 hour and about 6 hours.

* * * * *

SEQUENCE LISTING

<160> NUMBER OF SEQ ID NOS: 22

<210> SEQ ID NO 1
<211> LENGTH: 1323
<212> TYPE: DNA
<213> ORGANISM: Clostridium botulinum

<400> SEQUENCE: 1

```
atgccgtttg tgaacaaaca gtttaactat aaagatccgg tgaacggcgt ggatattgcg      60
tatattaaaa ttccgaacgt gggccagatg cagccggtga aagcgtttaa aattcataac     120
aaaatttggg tgattccgga acgcgatacc tttaccaacc cggaagaagg cgatctgaac     180
ccgccgccgg aagcgaaaca ggtgccggtg agctattatg atagcaccta tctgagcacc     240
gataacgaaa aagataacta tctgaaaggc gtgaccaaac tgtttgaacg catttatagc     300
accgatctgg gccgcatgct gctgaccagc attgtgcgcg gcattccgtt ttggggcggc     360
agcaccattg ataccgaact gaaagtgatt gataccaact gcattaacgt gattcagccg     420
gatggcagct atcgcagcga agaactgaac ctggtgatta ttggcccgag cgcggatatt     480
attcagtttg aatgcaaaag ctttggccat gaagtgctga acctgacccg caacggctat     540
ggcagcaccc agtatattcg ctttagcccg gatttacct ttggctttga agaaagcctg     600
gaagtggata ccaacccgct gctgggcgcg ggcaaatttg cgaccgatcc ggcggtgacc     660
ctggcgcatg aactgattca tgcgggccat cgcctgtatg gcattgcgat taacccgaac     720
cgcgtgttta aagtgaacac caacgcgtat tatgaaatga gcggcctgga agtgagcttt     780
gaagaactgc gcacctttgg cggccatgat gcgaaattta ttgatagcct gcaggaaaac     840
gaatttcgcc tgtattatta taacaaattt aaagatattg cgagcaccct gaacaaagcg     900
aaaagcattg tgggcaccac cgcgagcctg cagtatatga aaaacgtgtt taaagaaaaa     960
tatctgctga gcgaagatac cagcggcaaa tttagcgtgg ataaactgaa atttgataaa    1020
ctgtataaaa tgctgaccga aatttatacc gaagataact tgtgaaatt tttaaagtg    1080 ctgaaccgca aaacctatct gaactttgat aaagcggtgt ttaaaattaa cattgtgccg    1140
aaagtgaact ataccattta tgatggcttt aacctgcgca acaccaacct ggcggcgaac    1200
tttaacggcc agaacaccga aattaacaac atgaacttta ccaaactgaa aaactttacc    1260
ggcctgtttg aattttataa actgctgtgc gtgcgcggca ttattaccag caaaaccaaa    1320
tag                                                                   1323
```

<210> SEQ ID NO 2
<211> LENGTH: 440
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Val Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
    370                 375                 380

Thr Ile Tyr Asp Gly Phe Asn Leu Arg Asn Thr Asn Leu Ala Ala Asn
```

```
                385             390             395             400
Phe Asn Gly Gln Asn Thr Glu Ile Asn Asn Met Asn Phe Thr Lys Leu
                    405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys
                435                 440

<210> SEQ ID NO 3
<211> LENGTH: 1347
<212> TYPE: DNA
<213> ORGANISM: Clostridium botulinum

<400> SEQUENCE: 3
atgccgtttg tgaacaaaca gtttaactat aaagatccgg tgaacggcgt ggatattgcg      60
tatattaaaa ttccgaacgc gggccagatg cagccggtga aagcgtttaa aattcataac     120
aaaatttggg tgattccgga acgcgatacc tttaccaacc cggaagaagg cgatctgaac     180
ccgccgccgg aagcgaaaca ggtgccggtg agctattatg atagcaccta tctgagcacc     240
gataacgaaa aagataacta tctgaaaggc gtgaccaaac tgtttgaacg catttatagc     300
accgatctgg ccgcatgct gctgaccagc attgtgcgcg cattccgtt tggggcggc       360 agcaccattg taccgaact gaaagtgatt gataccaact gcattaacgt gattcagccg     420
gatggcagct atcgcagcga agaactgaac ctggtgatta ttggcccgag cgcggatatt     480
attcagtttg aatgcaaaag ctttggccat gatgtgctga acctgacccg caacggctat     540
ggcagcaccc agtatattcg ctttagcccg gattttacct ttggctttga gaaaagcctg     600
gaagtggata ccaaccccgct gctgggcgcg ggcaaatttg cgaccgatcc ggcggtgacc     660
ctggcgcatg aactgattca tgcggaacat cgcctgtatg gcattgcgat taacccgaac     720
cgcgtgttta agtgaacac caacgcgtat tatgaaatga cggcctgga agtgagcttt     780 gaagaactgc gcacctttgg cggccatgat gcgaaattta ttgatagcct gcaggaaaac     840
gaatttcgcc tgtattatta taacaaattt aaagatgtgg cgagcaccct gaacaaagcg     900
aaaagcatta ttggcaccac cgcgagcctg cagtatatga aaaacgtgtt taagaaaaaa     960
tatctgctga gcgaagatac cagcggcaaa tttagcgtgg ataaactgaa atttgataaa    1020
ctgtataaaa tgctgaccga atttatacc gaagataact tgtgaacttt ttaaagtg       1080 attaaccgca aaacctatct gaactttgat aaagcggtgt tcgcattaa cattgtgccg    1140 gatgaaaact ataccattaa agatggcttt aacctgaaag cgcgaacct gagcaccaac    1200 tttaacggcc agaacaccga attaacagc cgcaacttta cccgcctgaa aaactttacc    1260
ggcctgtttg aattttataa actgctgtgc gtgcgcggca ttattccgtt taaaaccaaa    1320
agcctggatg aaggctataa caaatag                                        1347

<210> SEQ ID NO 4
<211> LENGTH: 448
<212> TYPE: PRT
<213> ORGANISM: Clostridium botulinum

<400> SEQUENCE: 4

Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
```

```
                35                  40                  45
Asp Thr Phe Thr Asn Pro Glu Glu Gly Asp Leu Asn Pro Pro Pro Glu
 50                  55                  60
Ala Lys Gln Val Pro Val Ser Tyr Tyr Asp Ser Thr Tyr Leu Ser Thr
 65                  70                  75                  80
Asp Asn Glu Lys Asp Asn Tyr Leu Lys Gly Val Thr Lys Leu Phe Glu
                 85                  90                  95
Arg Ile Tyr Ser Thr Asp Leu Gly Arg Met Leu Leu Thr Ser Ile Val
                100                 105                 110
Arg Gly Ile Pro Phe Trp Gly Gly Ser Thr Ile Asp Thr Glu Leu Lys
            115                 120                 125
Val Ile Asp Thr Asn Cys Ile Asn Val Ile Gln Pro Asp Gly Ser Tyr
        130                 135                 140
Arg Ser Glu Glu Leu Asn Leu Val Ile Ile Gly Pro Ser Ala Asp Ile
145                 150                 155                 160
Ile Gln Phe Glu Cys Lys Ser Phe Gly His Asp Val Leu Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Lys Phe Ala Thr Asp Pro Ala Val Thr Leu Ala His Glu
    210                 215                 220
Leu Ile His Ala Glu His Arg Leu Tyr Gly Ile Ala Ile Asn Pro Asn
225                 230                 235                 240
Arg Val Phe Lys Val Asn Thr Asn Ala Tyr Tyr Glu Met Ser Gly Leu
                245                 250                 255
Glu Val Ser Phe Glu Glu Leu Arg Thr Phe Gly Gly His Asp Ala Lys
            260                 265                 270
Phe Ile Asp Ser Leu Gln Glu Asn Glu Phe Arg Leu Tyr Tyr Tyr Asn
        275                 280                 285
Lys Phe Lys Asp Val Ala Ser Thr Leu Asn Lys Ala Lys Ser Ile Ile
    290                 295                 300
Gly Thr Thr Ala Ser Leu Gln Tyr Met Lys Asn Val Phe Lys Glu Lys
305                 310                 315                 320
Tyr Leu Leu Ser Glu Asp Thr Ser Gly Lys Phe Ser Val Asp Lys Leu
                325                 330                 335
Lys Phe Asp Lys Leu Tyr Lys Met Leu Thr Glu Ile Tyr Thr Glu Asp
            340                 345                 350
Asn Phe Val Asn Phe Phe Lys Val Ile Asn Arg Lys Thr Tyr Leu Asn
        355                 360                 365
Phe Asp Lys Ala Val Phe Arg Ile Asn Ile Val Pro Asp Glu Asn Tyr
    370                 375                 380
Thr Ile Lys Asp Gly Phe Asn Leu Lys Gly Ala Asn Leu Ser Thr Asn
385                 390                 395                 400
Phe Asn Gly Gln Asn Thr Glu Ile Asn Ser Arg Asn Phe Thr Arg Leu
                405                 410                 415
Lys Asn Phe Thr Gly Leu Phe Glu Phe Tyr Lys Leu Leu Cys Val Arg
            420                 425                 430
Gly Ile Ile Pro Phe Lys Thr Lys Ser Leu Asp Glu Gly Tyr Asn Lys
        435                 440                 445

<210> SEQ ID NO 5
<211> LENGTH: 1335
```

<212> TYPE: DNA
<213> ORGANISM: Clostridium botulinum

<400> SEQUENCE: 5

```
atgccgtttg tgaacaaacc gtttaactat cgcgatccgg caacggcgt ggatattgcg      60
tatattaaaa ttccgaacgc gggccagatg cagccggtga aagcgtttaa aattcatgaa    120
ggcgtgtggg tgattccgga acgcgatacc tttaccaacc cggaagaagg cgatctgaac    180
ccgccgccgg aagcgaaaca ggtgccggtg agctattatg atagcaccta tctgagcacc    240
gataacgaaa aagataacta tctgaaaggc gtgattaaac tgtttgatcg catttatagc    300
accggcctgg gccgcatgct gctgagcttt attgtgaaag cattccgtt ttggggcggc     360
agcaccattg ataccgaact gaaagtgatt gataccaact gcattaacgt gattgaaccg    420
ggcggcagct atcgcagcga agaactgaac ctggtgatta ccggcccgag cgcggatatt    480
attcagtttg aatgcaaaag ctttggccat gatgtgttta acctgacccg caacggctat    540
ggcagcaccc agtatattcg ctttagcccg gattttacct ttggctttga agaaagcctg    600
gaagtggata ccaacccgct gctgggcgcg gcacctttg cgaccgatcc ggcggtgacc     660
ctggcgcatg aactgattca tgcggcgcat cgcctgtatg cattgcgat taacccgaac    720
cgcgtgctga agtgaaaac caacgcgtat tatgaaatga gcggcctgga agtgagcttt    780
gaagaactgc gcacctttgg cggcaacgat accaacttta ttgatagcct gtggcagaaa    840
aaatttagcc gcgatgcgta tgataacctg cagaacattg cgcgcattct gaacgaagcg    900
aaaaccattg tggcaccac caccccgctg cagtatatga aaacattttt tattcgcaaa    960
tattttctga gcgaagatgc gagcggcaaa attagcgtga caaagcggc gtttaaagaa   1020
ttttatcgcg tgctgacccg cggctttacc gaactggaat tgtgaaccc gtttaaagtg    1080
attaaccgca aacctatctg aactttgat aaagcggtgt tcgcattaa cattgtgccg     1140
gatgaaaact ataccattaa cgaaggcttt aacctggaag cgcgaacag caacggccag   1200
aacaccgaaa ttaacagccg caacttacc cgcctgaaaa actttaccgg cctgtttgaa    1260
ttttataaac tgctgtgcgt gcgcggcatt attccgttta aaaccaaaag cctggatgaa   1320
ggctataaca aatag                                                    1335
```

<210> SEQ ID NO 6
<211> LENGTH: 444
<212> TYPE: PRT
<213> ORGANISM: Clostridium botulinum

<400> SEQUENCE: 6

```
Met Pro Phe Val Asn Lys Pro Phe Asn Tyr Arg Asp Pro Gly Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Glu Gly Val Trp Val Ile Pro Glu Arg
        35                  40                  45

Asp Thr Phe Thr Asn Pro Glu Glu Gly Asp Leu Asn Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Ile Lys Leu Phe Asp
                85                  90                  95

Arg Ile Tyr Ser Thr Gly Leu Gly Arg Met Leu Leu Ser Phe Ile Val
            100                 105                 110
```

```
Lys Gly Ile Pro Phe Trp Gly Gly Ser Thr Ile Asp Thr Glu Leu Lys
            115                 120                 125
Val Ile Asp Thr Asn Cys Ile Asn Val Ile Glu Pro Gly Gly Ser Tyr
        130                 135                 140
Arg Ser Glu Glu Leu Asn Leu Val Ile Thr Gly Pro Ser Ala Asp Ile
145                 150                 155                 160
Ile Gln Phe Glu Cys Lys Ser Phe Gly His Asp Val Phe Asn Leu Thr
                165                 170                 175
Arg Asn Gly Tyr Gly Ser Thr Gln Tyr Ile Arg Phe Ser Pro Asp Phe
            180                 185                 190
Thr Phe Gly Phe Glu Glu Ser Leu Glu Val Asp Thr Asn Pro Leu Leu
        195                 200                 205
Gly Ala Gly Thr Phe Ala Thr Asp Pro Ala Val Thr Leu Ala His Glu
    210                 215                 220
Leu Ile His Ala Ala His Arg Leu Tyr Gly Ile Ala Ile Asn Pro Asn
225                 230                 235                 240
Arg Val Leu Lys Val Lys Thr Asn Ala Tyr Tyr Glu Met Ser Gly Leu
                245                 250                 255
Glu Val Ser Phe Glu Glu Leu Arg Thr Phe Gly Gly Asn Asp Thr Asn
            260                 265                 270
Phe Ile Asp Ser Leu Trp Gln Lys Lys Phe Ser Arg Asp Ala Tyr Asp
        275                 280                 285
Asn Leu Gln Asn Ile Ala Arg Ile Leu Asn Glu Ala Lys Thr Ile Val
    290                 295                 300
Gly Thr Thr Thr Pro Leu Gln Tyr Met Lys Asn Ile Phe Ile Arg Lys
305                 310                 315                 320
Tyr Phe Leu Ser Glu Asp Ala Ser Gly Lys Ile Ser Val Asn Lys Ala
                325                 330                 335
Ala Phe Lys Glu Phe Tyr Arg Val Leu Thr Arg Gly Phe Thr Glu Leu
            340                 345                 350
Glu Phe Val Asn Pro Phe Lys Val Ile Asn Arg Lys Thr Tyr Leu Asn
        355                 360                 365
Phe Asp Lys Ala Val Phe Arg Ile Asn Ile Val Pro Asp Glu Asn Tyr
    370                 375                 380
Thr Ile Asn Glu Gly Phe Asn Leu Glu Gly Ala Asn Ser Asn Gly Gln
385                 390                 395                 400
Asn Thr Glu Ile Asn Ser Arg Asn Phe Thr Arg Leu Lys Asn Phe Thr
                405                 410                 415
Gly Leu Phe Glu Phe Tyr Lys Leu Leu Cys Val Arg Gly Ile Ile Pro
            420                 425                 430
Phe Lys Thr Lys Ser Leu Asp Glu Gly Tyr Asn Lys
        435                 440

<210> SEQ ID NO 7
<211> LENGTH: 1326
<212> TYPE: DNA
<213> ORGANISM: Clostridium botulinum

<400> SEQUENCE: 7
atgccggtga ccattaacaa ctttaactat aacgatccga ttgataacaa caacattatt        60
atgatggaac cgccgtttgc gcgcggcacc ggcgctatt ataaagcgtt taaaattacc       120
gatcgcattt ggattattcc ggaacgctat acctttggct ataaaccgga agattttaac       180
aaaagcagcg gcattttaa ccgcgatgtg tgcgaatatt atgatccgga ttatctgaac       240
accaacgata aaaaaaacat ttttctgcag accatgatta aactgtttaa ccgcattaaa       300
```

```
agcaaaccgc tgggcgaaaa actgctggaa atgattatta acggcattcc gtatctgggc    360
gatcgccgcg tgccgctgga agaatttaac accaacattg cgagcgtgac cgtgaacaaa    420
ctgattagca acccgggcga agtggaacgc aaaaaaggca ttttgcgaa cctgattatt     480 tttggcccgg gcccggtgct gaacgaaaac gaaaccattg atattggcat tcagaaccat    540
tttgcgagcc gcgaaggctt tggcggcatt atgcagatga atttttgccc ggaatatgtg    600
agcgtgttta caacgtgca ggaaaacaaa ggcgcgagca ttttaaccg ccgcggctat      660 tttagcgatc cggcgctgat tctgatgcat gaactgattc atgtgctgca tggcctgtat    720
ggcattaaag tggatgatct gccgattgtg ccgaacgaaa aaaattttt tatgcagagc     780 accgatgcga ttcaggcgga agaactgtat acctttggcg ccaggatcc gagcattatt     840 accccgagca ccgataaaag catttatgat aaagtgctgc agaactttcg cggcattgtg    900
gatcgcctga caaagtgct ggtgtgcatt agcgatccga acattaacat taacatttat     960
aaaaacaaat ttaaagataa atataaattt gtggaagata gcgaaggcaa atatagcatt   1020
gatgtggaaa gctttgataa actgtataaa agcctgatgt ttggctttac gaaaccaac   1080 attgcggaaa actataaaat taaaacccgc gcgagctatt ttagcgatag cctgccgccg   1140
gtgaaaatta aaacctgctg ggataacgaa atttatacca ttgaagaagg ctttaacatt   1200
agcgataaag atatggaaaa agaatatcgc ggccagaaca aagcgattaa caaacaggcg   1260
tatgaagaaa ttagcaaaga acatctggcg gtgtataaaa ttcagatgtg caaaagcgtg   1320
aaatag                                                              1326

<210> SEQ ID NO 8
<211> LENGTH: 441
<212> TYPE: PRT
<213> ORGANISM: Clostridium botulinum

<400> SEQUENCE: 8

Met Pro Val Thr Ile Asn Asn Phe Asn Tyr Asn Asp Pro Ile Asp Asn
1               5                  10                  15

Asn Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190
```

```
Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
        210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
                260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
                340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
        370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
                420                 425                 430

Lys Ile Gln Met Cys Lys Ser Val Lys
        435                 440

<210> SEQ ID NO 9
<211> LENGTH: 1323
<212> TYPE: DNA
<213> ORGANISM: Clostridium botulinum

<400> SEQUENCE: 9
atgccggtga ccattaacaa ctttaactat aacgatccga ttgataacga taacattatt      60
atgatggaac cgccgtttgc gcgcggcacc ggccgctatt ataaagcgtt taaaattacc     120
gatcgcattt ggattattcc ggaacgctat acctttggct ataaaccgga agattttaac     180
aaaagcagcg gcattttaa ccgcgatgtg tgcgaatatt atgatccgga ttatctgaac     240
accaacgata aaaaaaacat ttttctgcag accatgatta aactgtttaa ccgcattaaa     300
agcaaaccgc tgggcgaaaa actgctggaa atgattatta cggcattcc gtatctgggc     360 gatcgccgcg tgccgctgga agaatttaac ccaacattg cgagcgtgac cgtgaacaaa     420
ctgattagca acccgggcga gtggaacag aaaaaaggca ttttgcgaa cctgattatt     480 tttgccccgg gccggtgct gaacgaaaac gaaaccattg atattggcat tcagaaccat     540
tttgcgagcc gcgaaggctt tggcggcatt atgcagatga attttgccc ggaatatgtg     600 agcgtgttta caacgtgca ggaaaacaaa ggcgcgagca tttttaaccg ccgcggctat     660
tttagcgatc cggcgctgat tctgatgcat gaactgattc atgtgctgca tggcctgtat     720
```

```
ggcattaaag tggatgatct gccgattgtg ccgaacgaaa aaaaattttt tatgcagagc    780
accgatacca ttcaggcgga agaactgtat acctttggcg gccaggatcc gagcattatt    840
agcccgagca ccgataaaag catttatgat aaagtgctgc agaactttcg cggcattgtg    900
gatcgcctga caaagtgct ggtgtgcatt agcgatccga cattaacat taacatttat    960 aaaaacaaat ttaagataa atataaattt gtggaagata gcgaaggcaa atatagcatt   1020
gatgtggaaa gctttaacaa actgtataaa agcctgatgt ttggctttac cgaaattaac   1080
attgcggaaa actataaaat taaaacccgc gcgagctatt ttagcgatag cctgccgccg   1140
gtgaaaatta aaacctgct ggataacgaa atttatacca ttgaagaagg ctttaacatt   1200
agcgataaaa acatgggcaa agaatatcgc ggccagaaca aagcgattaa caaacaggcg   1260
tatgaagaaa ttagcaaaga acatctggcg gtgtataaaa ttcagatgtg caaaagcgtg   1320
tag                                                                1323
```

<210> SEQ ID NO 10
<211> LENGTH: 440
<212> TYPE: PRT
<213> ORGANISM: Clostridium botulinum

<400> SEQUENCE: 10

```
Met Pro Val Thr Ile Asn Asn Phe Asn Tyr Asn Asp Pro Ile Asp Asn
1               5                   10                  15

Asp Asn Ile Ile Met Met Glu Pro Pro Phe Ala Arg Gly Thr Gly Arg
            20                  25                  30

Tyr Tyr Lys Ala Phe Lys Ile Thr Asp Arg Ile Trp Ile Ile Pro Glu
        35                  40                  45

Arg Tyr Thr Phe Gly Tyr Lys Pro Glu Asp Phe Asn Lys Ser Ser Gly
    50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Gln Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Thr Ile Gln Ala Glu Glu Leu Tyr Thr Phe
```

```
                     260                 265                 270
Gly Gly Gln Asp Pro Ser Ile Ile Ser Pro Ser Thr Asp Lys Ser Ile
            275                 280                 285

Tyr Asp Lys Val Leu Gln Asn Phe Arg Gly Ile Val Asp Arg Leu Asn
            290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
            325                 330                 335

Lys Tyr Ser Ile Asp Val Glu Ser Phe Asn Lys Leu Tyr Lys Ser Leu
            340                 345                 350

Met Phe Gly Phe Thr Glu Ile Asn Ile Ala Glu Asn Tyr Lys Ile Lys
            355                 360                 365

Thr Arg Ala Ser Tyr Phe Ser Asp Ser Leu Pro Pro Val Lys Ile Lys
            370                 375                 380

Asn Leu Leu Asp Asn Glu Ile Tyr Thr Ile Glu Glu Gly Phe Asn Ile
385                 390                 395                 400

Ser Asp Lys Asn Met Gly Lys Glu Tyr Arg Gly Gln Asn Lys Ala Ile
            405                 410                 415

Asn Lys Gln Ala Tyr Glu Glu Ile Ser Lys Glu His Leu Ala Val Tyr
            420                 425                 430

Lys Ile Gln Met Cys Lys Ser Val
            435                 440

<210> SEQ ID NO 11
<211> LENGTH: 1350
<212> TYPE: DNA
<213> ORGANISM: Clostridium botulinum

<400> SEQUENCE: 11
atgccgatta ccattaacaa ctttaactat agcgatccgg tggataacaa aaacattctg      60
tatctggata cccatctgaa caccctggcg aacgaaccgg aaaaagcgtt tcgcattacc     120
ggcaacattt gggtgattcc ggatcgcttt agccgcaaca gcaacccgaa cctgaacaaa     180
ccgccgcgcg tgaccagccc gaaaagcggc tattatgatc gaactatctc gagcaccgat     240
agcgataaag atccgtttct gaaagaaatt attaaactgt ttaaacgcat taacagccgc     300
gaaattggcg aagaactgat ttatcgcctg agcaccgata ttccgtttcc gggcaacaac     360 aacacccccga ttaacacctt tgattttgat gtggatttta cagcgtggga tgtgaaaacc     420
cgccagggca caactgggt gaaaaccggc agcattaacc gagcgtgat tattaccggc     480 ccgcgcgaaa acattattga tccggaaacc agcacccttta aactgaccaa caacaccttt     540
gcggcgcagg aaggctttgg cgcgctgagc attattagca ttagcccgcg ctttatgctg     600
acctatagca cgcgaccaa cgatgtgggc gaaggccgct ttagcaaaag cgaattttgc     660
atggatccga ttctgattct gatgcatgaa ctgaaccatg cgatgcataa cctgtatggc     720
attgcgattc cgaacgatca gaccattagc agcgtgacca gcaacatttt ttatagccag     780
tataacgtga aactggaata tgcggaaatt tatgcgtttg cggcccccgac cattgatctg     840 attccgaaaa gcgcgcgcaa atatttttgaa gaaaaagcgc tggattatta tcgcagcatt     900
gcgaaacgcc tgaacagcat taccaccgcg aacccgagcg ctttaacaa atatattggc     960 gaatataaac agaaactgat tcgcaaatat cgctttgtgg tggaaagcag cggcgaagtg    1020
accgtgaacc gcaacaaatt tgtggaactg tataacgaac tgacccagat ttttaccgaa    1080
tttaactatg cgaaaattta taacgtgcag aaccgcaaaa tttatctgag caacgtgtat    1140
```
accccggtga ccgcgaacat tctggatgat aacgtgtatg atattcagaa cggctttaac 1200
attccgaaaa gcaacctgaa cgtgctgttt atgggccaga acctgagccg caacccggcg 1260
ctgcgcaaag tgaacccgga aaacatgctg tatctgttta ccaaattttg ccataaagcg 1320
attgatggcc gcagcctgta taacaaatag 1350

<210> SEQ ID NO 12
<211> LENGTH: 449
<212> TYPE: PRT
<213> ORGANISM: Clostridium botulinum

<400> SEQUENCE: 12

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asp
        195                 200                 205

Val Gly Glu Gly Arg Phe Ser Lys Ser Glu Phe Cys Met Asp Pro Ile
    210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
            260                 265                 270

Phe Gly Gly Pro Thr Ile Asp Leu Ile Pro Lys Ser Ala Arg Lys Tyr
        275                 280                 285

Phe Glu Glu Lys Ala Leu Asp Tyr Tyr Arg Ser Ile Ala Lys Arg Leu
    290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

```
Ser Gly Glu Val Thr Val Asn Arg Asn Lys Phe Val Glu Leu Tyr Asn
            340                 345                 350

Glu Leu Thr Gln Ile Phe Thr Glu Phe Asn Tyr Ala Lys Ile Tyr Asn
            355                 360                 365

Val Gln Asn Arg Lys Ile Tyr Leu Ser Asn Val Tyr Thr Pro Val Thr
            370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430

Phe Thr Lys Phe Cys His Lys Ala Ile Asp Gly Arg Ser Leu Tyr Asn
                435                 440                 445

Lys

<210> SEQ ID NO 13
<211> LENGTH: 1329
<212> TYPE: DNA
<213> ORGANISM: Clostridium botulinum

<400> SEQUENCE: 13
atgacctggc cggtgaaaga ttttaactat agcgatccgg tgaacgataa cgatattctg      60
tatctgcgca ttccgcagaa caaactgatt accaccccgg tgaaagcgtt tatgattacc     120
cagaacattt gggtgattcc ggaacgcttt agcagcgata ccaacccgag cctgagcaaa     180
ccgccgcgcc cgaccagcaa atatcagagc tattatgatc gagctatctg agcaccgat      240 gaacagaaag atacctttct gaaaggcatt attaaactgt taaacgcat taacgaacgc     300 gatattggca aaaaactgat taactatctg gtggtgggca gcccgtttat gggcgatagc     360
agcaccccgg aagataccct tgatttttac cgccatacca ccaacattgc ggtgaaaaa     420 tttgaaaacg gcagctggaa agtgaccaac attattaccc gagcgtgct gattttttggc    480 ccgctgccga cattctgga ttataccgcg agcctgaccc tgcagggcca gcagagcaac     540
ccgagctttg aaggctttgg caccctgagc attctgaaag tggcgccgga atttctgctg    600
acctttagcg atgtgaccag caaccagagc agcgcggtgc tgggcaaaag cattttttgc   660
atggatccgg tgattgcgct gatgcatgaa ctgacccata gcctgcatca gctgtatggc    720
attaacattc cgagcgataa acgcattcgc cgcaggtga gcgaaggctt ttttagccag    780
gatggcccga acgtgcagtt tgaagaactg tataccttg gcggcctgga tgtggaaatt     840
attccgcaga ttaacgcag ccagctgcgc gaaaaagcgc tgggccatta taaagatatt     900
gcgaaacgcc tgaacaacat taacaaaacc attccgagca gctggattag caacattgat     960
aaatataaaa aaattttttag cgaaaaatat aactttgata agataacac cggcaacttt    1020 gtggtgaaca ttgataaatt taacagcctg tatagcgatc tgaccaacgt gatgagcgaa    1080
gtggtgtata gcagccagta taacgtgaaa aaccgcaccc attattttag ccgccattat    1140
ctgccggtgt ttgcgaacat tctggatgat aacatttata ccattcgcga tggctttaac    1200
ctgaccaaca aaggctttaa cattgaaaac agcggccaga acattgaacg caacccggcg    1260
ctgcagaaac tgagcagcga aagcgtggtg atctgttta ccaaagtgtg cctgcgcctg    1320
accaaatag                                                            1329

<210> SEQ ID NO 14
<211> LENGTH: 442
```

-continued

```
<212> TYPE: PRT
<213> ORGANISM: Clostridium botulinum

<400> SEQUENCE: 14

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Arg His Tyr Leu Pro Val Phe
    370                 375                 380

Ala Asn Ile Leu Asp Asp Asn Ile Tyr Thr Ile Arg Asp Gly Phe Asn
385                 390                 395                 400
```

```
Leu Thr Asn Lys Gly Phe Asn Ile Glu Asn Ser Gly Gln Asn Ile Glu
            405                 410                 415

Arg Asn Pro Ala Leu Gln Lys Leu Ser Ser Glu Ser Val Val Asp Leu
        420                 425                 430

Phe Thr Lys Val Cys Leu Arg Leu Thr Lys
        435                 440
```

<210> SEQ ID NO 15
<211> LENGTH: 1269
<212> TYPE: DNA
<213> ORGANISM: Clostridium botulinum

<400> SEQUENCE: 15

```
atgccgaaaa ttaacagctt taactataac gatccggtga acgatcgcac cattctgtat      60
attaaaccgg gcggctgcca ggaatttat aaaagcttta acattatgaa aacatttgg       120
attattccgg aacgcaacgt gattggcacc accccgcagg attttcatcc gccgaccagc     180
ctgaaaaacg gcgatagcag ctattatgat ccgaactatc tgcagagcga tgaagaaaaa     240
gatcgctttc tgaaaattgt gaccaaaatt tttaaccgca ttaacaacaa cctgagcggc     300
ggcattctgc tggaagaact gagcaaagcg aacccgtatc tgggcaacga taacaccccg     360
gataaccagt tcatattgg cgatgcgagc gcggtggaaa ttaaatttag caacggcagc     420
caggatattc tgctgccgaa cgtgattatt atgggcgcgg aaccggatct gtttgaaacc     480
aacagcagca acattagcct gcgcaacaac tatatgccga gcaaccatcg ctttggcagc     540
attgcgattg tgacctttag cccggaatat agctttcgct ttaacgataa ctgcatgaac     600
gaatttattc aggatccggc gctgaccctg atgcatgaac tgattcatag cctgcatggc     660
ctgtatggcg cgaaaggcat taccaccaaa tataccatta cccagaaaca gaacccgctg     720
attaccaaca ttcgcggcac caacattgaa gaatttctga cctttggcgg caccgatctg     780
aacattatta ccagcgcgca gagcaacgat atttatacca acctgctggc cggattataaa     840
aaaattgcga gcaaactgag caaagtgcag gtgagcaacc cgctgctgaa cccgtataaa     900
gatgtgtttg aagcgaaata tggcctggat aaagatgcga gcggcattta tagcgtgaac     960
attaacaaat ttacgatat ttttaaaaaa ctgtatagct ttaccgaatt tgatctggcg    1020
accaaatttc aggtgaaatg ccgccagacc tatattggcc agtataaata ttttaaactg    1080
agcaacctgc tgaacgatag catttataac attagcgaag gctataacat taacaacctg    1140
aaagtgaact tcgcggcca aacgcgaac ctgaacccgc gcattattac cccgattacc    1200
ggccgcggcc tggtgaaaaa aattattcgc ttttgcaaaa acattgtgag cgtgaaaggc    1260
attcgctag                                                            1269
```

<210> SEQ ID NO 16
<211> LENGTH: 422
<212> TYPE: PRT
<213> ORGANISM: Clostridium botulinum

<400> SEQUENCE: 16

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60
```

```
Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
             85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg
            420
```

<210> SEQ ID NO 17
<211> LENGTH: 1311
<212> TYPE: DNA
<213> ORGANISM: Clostridium botulinum

<400> SEQUENCE: 17
atgccggtgg cgattaacag ctttaactat aacgatccgg tgaacgatga taccattctg    60

```
tatatgcaga ttccgtatga agaaaaaagc aaaaaatatt ataaagcgtt tgaaattatg    120
cgcaacgtgt ggattattcc ggaacgcaac accattggca ccaacccgag cgattttgat    180
ccgccggcga gcctgaaaaa cggcagcagc gcgtattatg atccgaacta tctgaccacc    240
gatgcgaaaa aagatcgcta tctgaaaacc accattaaac tgtttaaacg cattaacagc    300
aacccggcgg gcaaagtgct gctgcaggaa attagctatg cgaaaccgta tctgggcaac    360
gatcataccc cgattgatga atttagcccg gtgacccgca ccaccagcgt gaacattaaa    420
ctgagcacca acgtggaaag cagcatgctg ctgaacctgc tggtgctggg cgcgggcccg    480 gatattttg aaagctgctg ctatccggtc gcaaactga ttgatccgga tgtggtgtat     540
gatccgagca actatggctt tggcagcatt aacattgtga cctttagccc ggaatatgaa    600
tatacctttt acgatattag cggcggccat aacagcagca ccgaaagctt tattgcggat    660
ccggcgatta gcctggcgca tgaactgatt catgcgctgc atggcctgta tggcgcgcgc    720
ggcgtgacct atgaagaaac cattgaagtg aaacaggcgc cgctgatgat tgcggaaaaa    780
ccgattcgcc tggaagaatt tctgaccttt ggcggccagg atctgaacat tattaccagc    840
gcgatgaaag aaaaaattta taacaacctg ctggcgaact atgaaaaaat gcgacccgc    900 ctgagcgaag tgaacagcgc gccgccggaa tatgatatta cgaatataa agattatttt    960 cagtggaaat atggcctgga taaaaacgcg gatggcagct ataccgtgaa cgaaaacaaa   1020
tttaacgaaa tttataaaaa actgtatagc tttaccgaaa gcgatctggc gaacaaattt   1080
aaagtgaaat gccgcaacac ctatttatt aaatatgaat ttctgaaagt gccgaacctg   1140
ctggatgatg atatttatac cgtgagcgaa ggctttaaca ttggcaacct ggcggtgaac   1200
aaccgcggcc agagcattaa actgaacccg aaaattattg atagcattcc ggataaaggc   1260
ctggtggaaa aaattgtgaa attttgcaaa agcgtgattc cgcgcaaata g           1311
```

<210> SEQ ID NO 18
<211> LENGTH: 436
<212> TYPE: PRT
<213> ORGANISM: Clostridium botulinum

<400> SEQUENCE: 18

```
Met Pro Val Ala Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110

Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
    130                 135                 140

Val Glu Ser Ser Met Leu Leu Asn Leu Leu Val Leu Gly Ala Gly Pro
145                 150                 155                 160
```

```
Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly His Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Glu Val
    290                 295                 300

Asn Ser Ala Pro Pro Glu Tyr Asp Ile Asn Glu Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ser Asp Leu Ala Asn Lys Phe Lys Val Lys Cys Arg Asn Thr Tyr
        355                 360                 365

Phe Ile Lys Tyr Glu Phe Leu Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
            420                 425                 430

Ile Pro Arg Lys
        435

<210> SEQ ID NO 19
<211> LENGTH: 1314
<212> TYPE: DNA
<213> ORGANISM: Clostridium barati
<400> SEQUENCE: 19
atgccggtga acattaacaa ctttaactat aacgatccga ttaacaacac caccattctg     60
tatatgaaaa tgccgtatta tgaagatagc aacaaatatt ataaagcgtt tgaaattatg    120
gataacgtgt ggattattcc ggaacgcaac attattggca aaaaaccgag cgatttttat    180
ccgccgatta gcctggatag cggcagcagc gcgtattatg atccgaacta tctgaccacc    240
gatgcggaaa aagatcgctt tctgaaaacc gtgattaaac tgtttaaccg cattaacagc    300
aacccggcgg gccaggtgct gctggaagaa attaaaaacg gcaaaccgta tctgggcaac    360
gatcataccg cggtgaacga attttgcgcg aacaaccgca gcaccagcgt ggaaattaaa    420
gaaagcaacg gcaccaccga tagcatgctg ctgaacctgg tgattctggg cccgggcccg    480
aacattctgg aatgcagcac ctttccggtg cgcatttttc cgaacaacat tgcgtatgat    540
```

```
ccgagcgaaa aaggctttgg cagcattcag ctgatgagct ttagcaccga atatgaatat    600
gcgtttaacg ataacaccga tctgtttatt gcggatccgg cgattagcct ggcgcatgaa    660
ctgattcatg tgctgcatgg cctgtatggc gcgaaaggcg tgaccaacaa aaaagtgatt    720
gaagtggatc agggcgcgct gatggcggcg gaaaaagata ttaaaattga agaatttatt    780
acctttggcg gccaggatct gaacattatt ccaacagca ccaaccagaa aatttatgtg    840
attctgctga gcaactatac cgcgattgcg agccgcctga gccaggtgaa ccgcaacaac    900
agcgcgctga acaccaccta ttataaaaac ttttttcagt ggaaatatgg cctggatcag    960
gatagcaacg gcaactatac cgtgaacatt agcaaattta cgcgattta taaaaaactg    1020 tttagcttta ccgaatgcga tctggcgcag aaatttcagg tgaaaaaccg cagcaactat   1080
ctgtttcatt ttaaaccgtt tcgcctgctg gatctgctgg atgataacat ttatagcatt   1140
agcgaaggct ttaacattgg cagcctgcgc gtgaacaaca acggcagaa cattaacctg    1200 aacagccgca ttgtgggccc gattccggat aacggcctgg tggaacgctt tgtgggcctg   1260
tgcaaaagca ttgtgagcaa aaaaggcacc aaaaacagcc tgtgcattaa atag         1314
```

<210> SEQ ID NO 20
<211> LENGTH: 437
<212> TYPE: PRT
<213> ORGANISM: Clostridium barati

<400> SEQUENCE: 20

```
Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205

Phe Ile Ala Asp Pro Ala Ile Ser Leu Ala His Glu Leu Ile His Val
    210                 215                 220

Leu His Gly Leu Tyr Gly Ala Lys Gly Val Thr Asn Lys Lys Val Ile
225                 230                 235                 240

Glu Val Asp Gln Gly Ala Leu Met Ala Ala Glu Lys Asp Ile Lys Ile
```

```
                 245                 250                 255
Glu Glu Phe Ile Thr Phe Gly Gly Gln Asp Leu Asn Ile Ile Thr Asn
                260                 265                 270

Ser Thr Asn Gln Lys Ile Tyr Val Ile Leu Leu Ser Asn Tyr Thr Ala
            275                 280                 285

Ile Ala Ser Arg Leu Ser Gln Val Asn Arg Asn Asn Ser Ala Leu Asn
        290                 295                 300

Thr Thr Tyr Tyr Lys Asn Phe Phe Gln Trp Lys Tyr Gly Leu Asp Gln
305                 310                 315                 320

Asp Ser Asn Gly Asn Tyr Thr Val Asn Ile Ser Lys Phe Asn Ala Ile
                325                 330                 335

Tyr Lys Lys Leu Phe Ser Phe Thr Glu Cys Asp Leu Ala Gln Lys Phe
            340                 345                 350

Gln Val Lys Asn Arg Ser Asn Tyr Leu Phe His Phe Lys Pro Phe Arg
        355                 360                 365

Leu Leu Asp Leu Leu Asp Asp Asn Ile Tyr Ser Ile Ser Glu Gly Phe
    370                 375                 380

Asn Ile Gly Ser Leu Arg Val Asn Asn Asn Gly Gln Asn Ile Asn Leu
385                 390                 395                 400

Asn Ser Arg Ile Val Gly Pro Ile Pro Asp Asn Gly Leu Val Glu Arg
                405                 410                 415

Phe Val Gly Leu Cys Lys Ser Ile Val Ser Lys Lys Gly Thr Lys Asn
            420                 425                 430

Ser Leu Cys Ile Lys
            435

<210> SEQ ID NO 21
<211> LENGTH: 1311
<212> TYPE: DNA
<213> ORGANISM: Clostridium botulinum

<400> SEQUENCE: 21
atgccggtga acattaaatt taactataac gatccgatta caacgatga tattattatg      60 atggaaccgt taacgatcc gggcccgggc acctattata aagcgtttcg cattattgat     120
cgcatttgga ttgtgccgga cgctttacc tatggctttc agccggatca gtttaacgcg     180
agcaccggcg tgtttagcaa agatgtgtat gaatatattg atccgaccta tctgaaaacc    240
gatgcggaaa agataaaatt tctgaaaacc atgattaaac tgtttaaccg cattaacagc    300
aaaccgagcg ccagcgcct gctggatatg attgtggatg cgattccgta tctgggcaac    360
gcgagcaccc cgccggataa atttgcggcg aacgtggcga acgtgagcat taacaaaaaa    420
attattcagc cggcgcgga agatcagatt aaaggcctga tgaccaaccct gattattttt    480 ggccccgggcc cggtgctgag cgataacttt accgatagca tgattatgaa cggccatagc    540
ccgattagcg aaggctttgg cgcgcgcatg atgattcgct tttgcccgag ctgcctgaac    600
gtgtttaaca acgtgcagga aaacaaagat accagcattt ttagccgccg cgcgtatttt    660
gcggatccgg cgctgaccct gatgcatgaa ctgattcatg tgctgcatgg cctgtatggc    720
attaaaatta gcaacctgcc gattaccccg aacaccaaag aattttttat gcagcatagc    780
gatccggtgc aggcggaaga actgtatacc tttggcggcc atgatccgag cgtgattagc    840
ccgagcaccg atatgaacat ttataacaaa gcgctgcaga actttcagga tattgcgaac    900
cgcctgaaca ttgtgagcag cgcgcagggc agcggcattg atattagcct gtataaacag    960
atttataaaa acaaatatga ttttgtggaa gatccgaacg gcaaatatag cgtggataaa   1020
```

```
gataaatttg ataaactgta taaagcgctg atgtttggct ttaccgaaac caacctggcg    1080
ggcgaatatg cattaaaac ccgctatagc tattttagcg aatatctgcc gccgattaaa    1140
accgaaaaac tgctggataa caccatttat acccagaacg aaggctttaa cattgcgagc    1200
aaaaacctga aaccgaatt taacggccag aacaaagcgg tgaacaaaga agcgtatgaa    1260
gaaattagcc tggaacatct ggtgattat cgcattgcga tgtgcaaata g            1311
```

<210> SEQ ID NO 22
<211> LENGTH: 437
<212> TYPE: PRT
<213> ORGANISM: Clostridium botulinum
<220> FEATURE:
<221> NAME/KEY: VARIANT
<222> LOCATION: (1)..(437)
<223> OTHER INFORMATION: Xaa=Any Amino Acid

<400> SEQUENCE: 22

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
```

-continued

```
            305                 310                 315                 320
        Gln Ile Tyr Lys Asn Lys Tyr Asp Phe Val Glu Asp Pro Asn Gly Lys
                        325                 330                 335
        Tyr Ser Val Asp Lys Asp Lys Phe Asp Lys Leu Tyr Lys Ala Leu Met
                        340                 345                 350
        Phe Gly Phe Thr Glu Thr Asn Leu Ala Gly Glu Tyr Gly Ile Lys Thr
                    355                 360                 365
        Arg Tyr Ser Tyr Phe Ser Glu Tyr Leu Pro Pro Ile Lys Thr Glu Lys
                370                 375                 380
        Leu Leu Asp Asn Thr Ile Tyr Thr Gln Asn Glu Gly Phe Asn Ile Ala
        385                 390                 395                 400
        Ser Lys Asn Leu Lys Thr Glu Phe Asn Gly Gln Asn Lys Ala Val Asn
                        405                 410                 415
        Lys Glu Ala Tyr Glu Glu Ile Ser Leu Glu His Leu Val Ile Tyr Arg
                    420                 425                 430
        Ile Ala Met Cys Lys
                    435
```